US012281076B2

(12) United States Patent
Babij et al.

(10) Patent No.: US 12,281,076 B2
(45) Date of Patent: Apr. 22, 2025

(54) PROCESS FOR SYNTHESIS OF PICOLINAMIDES

(71) Applicant: CORTEVA AGRISCIENCE LLC, Indianapolis, IN (US)

(72) Inventors: Nicholas R. Babij, Carmel, IN (US); Elizabeth O. McCusker, Carmel, IN (US); Gregory T. Whiteker, Carmel, IN (US); Neeraj Sane, Carmel, IN (US); Siyu Tu, Midland, MI (US); Xiaoyong Li, Zionsville, IN (US); Daniel W. Klosowski, Indianapolis, IN (US); Patrick T. McGough, Zionsville, IN (US); Meng Guo, Carmel, IN (US); Matthew Robinson, Indianapolis, IN (US); Jeffrey Scott Nissen, Indianapolis, IN (US); Tyler Davis, Carmel, IN (US); Yan Hao, Zionsville, IN (US)

(73) Assignee: CORTEVA AGRISCIENCE LLC, IN (US)

( * ) Notice: Subject to any disclaimer, the term of this patent is extended or adjusted under 35 U.S.C. 154(b) by 597 days.

(21) Appl. No.: 17/754,977

(22) PCT Filed: Oct. 15, 2020

(86) PCT No.: PCT/US2020/055658
§ 371 (c)(1),
(2) Date: Apr. 18, 2022

(87) PCT Pub. No.: WO2021/076681
PCT Pub. Date: Apr. 22, 2021

(65) Prior Publication Data

US 2022/0411375 A1 Dec. 29, 2022

Related U.S. Application Data

(60) Provisional application No. 62/923,235, filed on Oct. 18, 2019.

(51) Int. Cl.
*C07D 213/803* (2006.01)
*C07C 227/20* (2006.01)

(52) U.S. Cl.
CPC ........ *C07D 213/803* (2013.01); *C07C 227/20* (2013.01)

(58) Field of Classification Search
CPC ................................................ C07D 213/803
USPC ........................................................ 546/296
See application file for complete search history.

(56) References Cited

U.S. PATENT DOCUMENTS

| | | | |
|---|---|---|---|
| 4,051,173 | A | 9/1977 | Schacht |
| 4,588,735 | A | 5/1986 | Spatz |
| 5,342,835 | A | 8/1994 | Pepin et al. |
| 5,401,871 | A | 3/1995 | Talley |
| 5,475,132 | A | 12/1995 | Pepin et al. |
| 5,563,165 | A | 10/1996 | Talley |
| 5,665,351 | A | 9/1997 | Nair et al. |
| 5,760,068 | A | 6/1998 | Talley et al. |
| 5,852,042 | A | 12/1998 | Jakobi |
| 6,355,660 | B1 | 3/2002 | Ricks |
| 6,410,572 | B1 | 6/2002 | Schelberger |
| 6,436,421 | B1 | 8/2002 | Schindler |
| 6,521,622 | B1 | 2/2003 | Ricks |
| 6,706,740 | B2 | 3/2004 | Ricks |
| 6,812,237 | B2 | 11/2004 | Cowen et al. |
| 6,812,238 | B1 | 11/2004 | Fukuda et al. |
| 6,861,390 | B2 | 3/2005 | Meyer |
| 6,903,219 | B2 | 6/2005 | Niyaz |
| 6,916,932 | B2 | 7/2005 | Meyer |
| 6,927,225 | B2 | 8/2005 | Ricks |
| 6,953,807 | B2 | 10/2005 | Hutin et al. |
| 7,034,035 | B2 | 4/2006 | Ricks |
| 7,183,278 | B1 | 2/2007 | Imamura |
| 7,241,804 | B1 | 7/2007 | Hockenberry |
| 7,250,389 | B1 | 7/2007 | Sakanaka |
| RE39,991 | E | 1/2008 | Ricks |
| 7,442,672 | B2 | 10/2008 | Muller |
| 7,459,581 | B2 | 12/2008 | Derrer |
| 7,560,565 | B2 | 7/2009 | Bacque |
| 7,927,617 | B2 | 4/2011 | Koltzenburg |
| 8,008,231 | B2 | 8/2011 | Leatherman |
| 8,153,819 | B2 | 4/2012 | Dietz |
| 8,236,962 | B2 | 8/2012 | Hoekstra |
| 8,349,877 | B2 | 1/2013 | Brix |
| 8,415,274 | B2 | 4/2013 | Wachendorff-Neumann |
| 8,465,562 | B2 | 6/2013 | Chen |

(Continued)

FOREIGN PATENT DOCUMENTS

| | | |
|---|---|---|
| CL | 2015001862 | 10/2015 |
| CN | 101530104 | 9/2009 |

(Continued)

OTHER PUBLICATIONS

Anonymous, Synergistic Fungicidal Composition of Heterocyclic Aromatic Amides and Triazoles, ip.com Journal, ip.com, Electronic Publication, West Henrietta, NY, US, Jul. 2004, 11 pages.
Backman, P., Fungicide Formulation: Relationship to Biological Activity, Ann. Rev. Phytopathol, 1978, 16, pp. 211-237.
BASF New Fungicide Xemium Got Full Approval in EU, Agronews, Jul. 18, 2012 [retrieved on Apr. 2, 2014]. Retrieved from the Internet: ,URL:http://news.agropages.com/News/NewsDetail---7386.htm, 1 page.

(Continued)

*Primary Examiner* — Taofiq A Solola

(57) ABSTRACT

The present technology relates to processes, mixtures and intermediates useful for making picolinamide fungicides. The picolinamide compounds are prepared by processes that include coupling together a 4-methoxy-3-acyloxypicolinic acid with key 2-amino-L-alaninate esters derived from substituted 2-phenylethanols.

13 Claims, No Drawings

(56) References Cited

U.S. PATENT DOCUMENTS

| | | | |
|---|---|---|---|
| 8,470,840 | B2 | 6/2013 | Klittich |
| 8,476,193 | B2 | 7/2013 | Keeney |
| 8,580,959 | B2 | 11/2013 | Devasthale |
| 8,586,550 | B2 | 11/2013 | Lee et al. |
| 8,604,215 | B2 | 12/2013 | Phiasivongsa |
| 8,785,479 | B2 | 7/2014 | Meyer |
| 8,835,462 | B2 | 9/2014 | Meyer |
| 8,883,811 | B2 | 11/2014 | Owen |
| 8,916,579 | B2 | 12/2014 | Boebel |
| 9,006,259 | B2 | 4/2015 | Boebel |
| 9,084,418 | B2 | 7/2015 | Ehr |
| 9,131,690 | B2 | 9/2015 | Meyer |
| 9,144,239 | B2 | 9/2015 | Meyer |
| 9,155,305 | B2 | 10/2015 | Gary |
| 9,156,816 | B2 | 10/2015 | Ito |
| 9,179,674 | B2 | 11/2015 | Martin |
| 9,185,911 | B2 | 11/2015 | Inami |
| 9,198,419 | B2 | 12/2015 | Owen |
| 9,247,741 | B2 | 2/2016 | DeLorbe |
| 9,265,253 | B2 | 2/2016 | Li |
| 9,265,255 | B2 | 2/2016 | Funke |
| 9,271,496 | B2 | 3/2016 | Kemmitt |
| 9,271,497 | B2 | 3/2016 | Lorsbach |
| 9,414,596 | B2 | 8/2016 | Hakura et al. |
| 9,439,422 | B2 | 9/2016 | Martin |
| 9,482,661 | B2 | 11/2016 | Ross |
| 9,526,245 | B2 | 12/2016 | Owen et al. |
| 9,549,555 | B2 | 1/2017 | DeLorbe |
| 9,549,556 | B2 | 1/2017 | DeKorver |
| 9,629,365 | B2 | 4/2017 | Li |
| 9,681,664 | B2 | 6/2017 | Lalonde |
| 9,686,984 | B2 | 6/2017 | DeKorver |
| 9,700,047 | B2 | 7/2017 | Lu |
| 9,730,445 | B2 | 8/2017 | Yerkes |
| 9,750,248 | B2 | 9/2017 | Ouimette |
| 9,828,408 | B2 | 11/2017 | Kalayanov et al. |
| 9,840,475 | B2 | 12/2017 | Lorsbach |
| 9,936,697 | B2 | 4/2018 | Hopkins |
| 9,955,690 | B2 | 5/2018 | Owen |
| 9,955,691 | B2 | 5/2018 | Boebel |
| 9,974,301 | B2 | 5/2018 | Quiroz et al. |
| 9,974,304 | B2 | 5/2018 | DeKorver |
| 10,015,964 | B2 | 7/2018 | Ogawa et al. |
| 10,015,966 | B2 | 7/2018 | Taggi et al. |
| 10,040,764 | B2 | 8/2018 | Whiteker et al. |
| 10,111,432 | B2 | 10/2018 | Rigoli |
| 10,172,354 | B2 | 1/2019 | Ouimette et al. |
| 10,173,971 | B2 | 1/2019 | Yao |
| 10,173,981 | B2 | 1/2019 | Buchan |
| 10,182,568 | B2 | 1/2019 | Bravo-Altamirano |
| 10,188,109 | B2 | 1/2019 | Yao |
| 10,252,989 | B2 | 4/2019 | Yao |
| 10,433,555 | B2 | 10/2019 | Bravo-Altamirano et al. |
| 2002/0119979 | A1 | 8/2002 | Degenhardt |
| 2002/0177578 | A1 | 11/2002 | Ricks |
| 2003/0018052 | A1 | 1/2003 | Ricks |
| 2003/0022902 | A1 | 1/2003 | Ricks |
| 2003/0022903 | A1 | 1/2003 | Ricks |
| 2005/0239873 | A1 | 10/2005 | Hockenberry |
| 2006/0167281 | A1 | 7/2006 | Meijer |
| 2007/0010401 | A1 | 1/2007 | Noon |
| 2007/0066629 | A1 | 3/2007 | Tormo i Blasco |
| 2009/0203770 | A1 | 8/2009 | Hockenberry |
| 2009/0306142 | A1 | 12/2009 | Carson |
| 2010/0016163 | A1 | 1/2010 | Keiper |
| 2011/0070278 | A1 | 3/2011 | Lopez |
| 2011/0082162 | A1 | 4/2011 | Lorsbach |
| 2012/0245031 | A1 | 9/2012 | Gewehr |
| 2013/0296372 | A1 | 11/2013 | Owen |
| 2014/0051678 | A1 | 2/2014 | Clement-Schatlo |
| 2014/0357713 | A1 | 12/2014 | Damaj |
| 2015/0289508 | A1 | 10/2015 | Meyer |
| 2015/0322051 | A1 | 11/2015 | Lu |
| 2016/0037774 | A1 | 2/2016 | Schulz |
| 2016/0183526 | A1 | 6/2016 | Hopkins |
| 2016/0183527 | A1 | 6/2016 | Hopkins |
| 2017/0183324 | A1 | 6/2017 | Li |
| 2017/0273303 | A1 | 9/2017 | DeKorver |
| 2017/0273306 | A1 | 9/2017 | Lalonde |
| 2017/0290333 | A1 | 10/2017 | Bravo-Altamirano |
| 2018/0000084 | A1 | 1/2018 | Yao |
| 2018/0000085 | A1 | 1/2018 | Bravo-Altamirano et al. |
| 2018/0002288 | A1 | 1/2018 | Buchan |
| 2018/0002319 | A1 | 1/2018 | Wilmot |
| 2018/0002320 | A1 | 1/2018 | Wilmot |
| 2020/0255400 | A1 | 8/2020 | Lamberth et al. |

FOREIGN PATENT DOCUMENTS

| | | | |
|---|---|---|---|
| EP | 0002940 | | 7/1979 |
| FR | 2649699 | | 1/1991 |
| JP | 19940026884 | | 9/1995 |
| JP | 1998053583 | | 2/1998 |
| JP | H10-045747 | | 2/1998 |
| RU | 2613451 | | 3/2017 |
| WO | 1996010016 | | 4/1996 |
| WO | 199637472 | | 11/1996 |
| WO | 199741103 | | 6/1997 |
| WO | 1997019908 | | 6/1997 |
| WO | 1998018751 | | 5/1998 |
| WO | 1999011127 | | 11/1999 |
| WO | 2000076979 | | 12/2000 |
| WO | 200114339 | | 3/2001 |
| WO | 2005121069 | | 12/2005 |
| WO | 2008079387 | | 7/2008 |
| WO | 2011044213 | | 4/2011 |
| WO | 2012020777 | | 8/2011 |
| WO | 2012016989 | | 2/2012 |
| WO | 2016109301 | | 12/2012 |
| WO | 2013136275 | A1 | 9/2013 |
| WO | 2014106259 | | 7/2014 |
| WO | 2016007525 | | 7/2015 |
| WO | 2016109288 | | 12/2015 |
| WO | 2016109289 | | 12/2015 |
| WO | 2016109290 | | 12/2015 |
| WO | 2016109291 | | 12/2015 |
| WO | 2016109300 | | 12/2015 |
| WO | 2016109302 | | 12/2015 |
| WO | 2016109303 | | 12/2015 |
| WO | 2016109304 | | 12/2015 |
| WO | 2016109305 | | 12/2015 |
| WO | 2016106138 | A1 | 6/2016 |
| WO | 2016109257 | A1 | 7/2016 |
| WO | 2016122802 | A1 | 8/2016 |
| WO | 2016187201 | A2 | 11/2016 |
| WO | 2015005355 | | 3/2017 |
| WO | 2018098218 | A1 | 5/2018 |
| WO | 2018204435 | | 11/2018 |
| WO | 2018204437 | | 11/2018 |
| WO | 2019173665 | A1 | 9/2019 |
| WO | 2017061483 | | 9/2020 |

OTHER PUBLICATIONS

Bolton, M. et al., "Wheat leaf rust caused by Puccinia triticina," Molecular Plant Pathology, vol. 9, No. 5, 2008, pp. 563-575 [online] [retrieved on Feb. 3, 2016]. Retrieved from the Internet URL: https://www.researchgate.net/profile/Melvin_Bolton/publication/23483068_Wheat_leaf_rust_caused_by_Puccinia_triticina/links/0046352d94b8d5f2c9000000.pdf.

Davari, M. et al. "Quantum Chemical Investigation of Intramolecular Thione-Thiol Tautomerism of 1, 2, 4-triazole-3-thione and its disubstituted derivatives," Journal of Molecular Modeling, Sep. 2009, 16(5), pp. 841-855.

Cantacuzene, D., "Optimization of the papain catalyzed esterification of amino acids by alcohols and diols," Tetrahedron 45, 3 (1989): 741-748.

FRAC Code List: Fungicides Sorted by Mode of Action (including FRAC Code numbering), Fungicide Resistance Action Committee, Dec. 2008, 10 pages.

Fungicidal Mixtures, IP.com Prior Art Database Technical Disclosure, (Jul. 5, 2005), XP055073888, DOI: http://ip.com/pdf/ipcompad/IPCOM000126160D.pdf, 12 pages.

(56) References Cited

OTHER PUBLICATIONS

Gisi, U., "Synergistic Interaction of Fungicides in Mixtures," The American Phytopathology Society, vol. 86, No. 11, 1996, pp. 1273-1279.
Guseynov et al: "Study of the reaction of aminoacetic acid with dihydric alcohols and production of epoxy esters" Chemical Problems, 2009 (1), pp. 188-190.
Hu, Z. et al., "Synthesis of Novel Analogues of Antimycin A3," Tetrahedron Letters 49 (2008), pp. 5192-5195.
Huang, C. et al., "Synergistic Interactions between Chitinase ChiCW and Fungicides Against Plant Fungal Pathogens," J. Microbiol. Biotechnol., 2008, 18(4), pp. 784-787.
Kissling, E., "Crop Protection Pipeline Value Jumps to Euro 2.4 Billion," BASF SE, Mar. 10, 2011 [retrieved on Apr. 2, 2014], Retrieved from the internet: ,URL:http://agro.basf.com/agri/AP-Internet/en/content/news_room/news/basf-crop-protection-pipeline-value, 4 pages.
Koyanagi, T. et al., "Bioisoterism in Agrochemicals," Synthesis and Chemistry of Agrochemicals IV; Baker, D. et al., ACS Symposium Series; American Chemical Society: Washington, D.C., 1995, pp. 15-24.
Latin, R., et al, "Re-Examining Fungicide Synergism for Dollar Spot Control," GCM, Juky 2008, pp. 84-87.
Ueki, M., et al., "UK-2A, B, C, and D, Novel Antifungal Antibiotics from *Streptomyces* sp. 517-02 I. Fermentation, Isolation, and Biological Properties," The Journal of Antibiotics, vol. 49, No. 7, Jul. 1996, pp. 639-34.
O'Sullivan, E., et al., "Fungicide Resistance—an Increasing Problem," Proceedings of National Tillage Conference 2007, Published by Crop Research Centre, Oak Park, Carlow, Jan. 31, 2007, pp. 43-56.
Parker, J.E., et al., "Mechanism of Binding of Prothioconazole to Mycosphaerella graminicola CYP51 Differs from That of Other Azole Antifungals," Applied and Environmental Microbiology, vol. 77, No. 4, Feb. 2011, pp. 1460-1465.
PubChem: Open Chemistry Database, Substance Record for SID 74383515. Deposit Date Jun. 11, 2009 [retrieved on May 25, 2016] Retrieved from internet. <URL:https://pubchem.ncbi.nlm.nih.gov/substance/74383515#/section=Top>, 5 pages.
Science for a Better Life, Bayer CropScience "Positioned for Growth", Jun. 2008, 22 pages.
Calcium Dodecyl Benzene Sulfonate, CAS 26264-06-2, (http://www.hichem.com/product/showproduct.php?id=334639) Mar. 28, 2013, 6 pages.
Tani, K. et al., "UK2A, B, C, and D, Novel Antifungal Antibiotics—from *Streptomyces* sp. 517-02.," The Journal of Antibiotics, vol. 55, No. 3, Mar. 2002, pp. 315-321.
The Merck Index, Twelfth Edition, S. Budavari, Ed., Merck and Co., Inc., Whitehouse Station, NJ, 1996, pp. 2220, 3666, 7937 and 7946.
Usuki, Y., et al., "Semi-synthesis and biological evaluation of analogues of UK-2A, a novel antifungal antibiotic from *Streptomyces* sp. 517-02," Bioorganic & Medicinal Chemistry Letters, vol. 15, No. 8, 2005, pp. 2011-2014.
Usuki, Y. et al., "UK-2A, B, C, and D, Novel Antifungal Antibiotics from *Streptomyces* sp. 517-02 VI (2). Structure-activity Relationships of UK-2A," Journal of Antibiotics, vol. 55, No. 6, Jun. 2002, pp. 607-610.
Webster's New World Dictionary, Second College Edition, Guralnik, D, Ed., The World Publishing Co., New York, p. 1127 (1972).
Wilson, C.L. et al. "Fruit Volatiles Inhibitory to Monilinia Fruiticola and Botrytis cinerea," 1987, Plant Disease, vol. 71, No. 4, pp. 316-319.
Goellner et al. "Phakopsora pachyrhizi, the causal agent of Asian soybean rust." Molecular Plant Pathology, vol. 11, No. 2, pp. 169-177 (2010).
Fujita T, Ed. "Quantitative structure-activity analysis and database-aided bioisosteric structural transformation procedure as methodologies of agrochemical design"; Classical and Three Dimensional QSAR in Agrochemistry, ACS Symposium Series Washington, D.C. vol. 606, pp. 13-34 (1995).
Patani et al. Biosterism: A rational approach in drug design. Chemical Reviews, vol. 96, No. 8, pp. 3147-3176 (1996).
Kendall, S. et al. "Changes in sensitivity to DMI fungicides in Rhynchosporium secalis". Crop Protection, vol. 12, No. 5, pp. 357-362 (1993).
Cooke et al. "The effect of fungicide programmes based on epoxiconazole on the control and DMI sensitivity of Rhynchosporium secalis in winter barley." Crop Protection, vol. 23, No. 5, pp. 393-406 (2004).
Shimano et al. "Total synthesis of the antifungal dilactones UK-2A and UK-3a: The determination of their relative and absolute configurations, analog synthesis and antifungal activities". Tetrahedron, vol. 54, pp. 12745-12774 (1998).
Lippard, S. "Chemical Synthesis: The Art of Chemistry". Nature, vol. 416, p. 587 (2002).
Washburn, W.N., "Identification of a nonbasic melanin hormone receptor 1 antagonist as an antiobesity clinical candidate." Journal of medicinal chemistry 57, 18 (Aug. 28, 2014): 7509-7522.
Amiri et al. "Sensitivity of Botrytis cinerea field isolates to the novel succinate dehydrogenase inhibitors fluopyram, penthiopyrad, and fluxapuroxad". Annual Meeting of the American Phytopathological Society, Phytopathology, vol. 102 (2012).
Chitwood, D. "Nematicides". Encyclopedia of Agrochemicals (3), pp. 1104-1115, John Wiley & Sons, New York, NY, http://naldc.nal.usda.gov/download/43874/PDF (2003).
Hanafi et al. "UK2A, B, C, and D, Novel Antifungal Antibiotics from *Streptomyces* sp 517-02 II. Structural Elucidation." The Journal of Antibiotics, vol. 49, Issue 12, pp. 1226-1231 (1996).
Shibata et al. "UK1, A Novel Cytotoxic Metabolite from *Streptomyces* sp. 517-02 II. Structural Elucidation." The Journal of Antibiotics, vol. 46, Issue 7, pp. 1095-1100 (1993).
Shimano et al. "Enantioselective Total Synthesis of the Antifungal Dilactone, UK-2A: The Determination of the Relative and Absolute Configurations". Tetrahedron Letters, vol. 39, pp. 4363-4366 (1998).
Stephenson, G., et al. "Glossary of terms relating to pesticides". Pure and Applied Chemistry, vol. 78, No. 11, pp. 2075-2154, International Union of Pure and Applied Chemistry (2006).
Ueki, M., et al., "UK-1, A Novel Cytotoxic Metabolite from *Streptomyces* sp. 517-02 I. Taxonomy, Fermentation, Isolation, Physico-chemical and Biological Properties." The Journal of Antibiotics, vol. 46, No. 7, pp. 1089-1094 (1993).
Ueki et al. "UK-3A, A Novel Antifungal Antibiotic from *Streptomyces* sp. 517-02: Fermentation, Isolation, Structural Elucidation and Biological Properties". The Journal of Antibiotics, vol. 50, Issue 7, pp. 551-555 (1997).
Ueki et al. "The mode of action of UK-2A and UK-3A, Novel antifungal antibiotics from *Streptomyces* sp. 517-02". The Journal of Antibiotics, vol. 50, Issue 12, pp. 1052-1057 (1997).
International Searching Authority, International Search Report and Written Opinion for PCT/US14/58061 dated Dec. 15, 2014, 9 pages.
International Searching Authority, International Search Report and Written Opinion for PCT/US1458065 dated Dec. 22, 2014, 9 pages.
International Searching Authority, International Search Report and Written Opinion for PCT/US1528407 dated Aug. 5, 2015, 8 pages.
International Searching Authority, International Search Report and Written Opinion for PCT/Us1539407 dated Sep. 30, 2015, 9 pages.
International Searching Authority, International Search Report and Written Opinion for PCT/US1539409 dated Oct. 5, 2015, 10 pages.
International Searching Authority, International Search Report and Written Opinion for PCT/US1544383 dated Mar. 16, 2016, 11 pages.
International Searching Authority, International Search Report and Written Opinion for PCT/US2019/021263 dated May 10, 2019, 15 pages.
International Searching Authority, International Search Report and Written Opinion for PCT/US18/030561 dated Jun. 27, 2019, 5 pages.
International Searching Authority, International Search Report and Written Opinion for PCT/US18/30559 dated Jun. 27, 2018, 8 pages.

(56) References Cited

OTHER PUBLICATIONS

Gaylor, J. L., "Membrane-bound enzymes of cholesterol synthesis from lanosterol." Biochemical and biophysical research communications. 2002, 292.5 pp. 1139-1146.
Umetsu, Noriharu et al. "Development of novel pesticides in the 21st century" Journal of Pesticide Science. Mar. 2020, vol. 45, Issue 2, pp. 54-74.
International Searching Authority, International Search Report and Written Opinion for PCT/US20/055658 dated Feb. 9, 2021, 9 pages.

PROCESS FOR SYNTHESIS OF PICOLINAMIDES

1. CROSS REFERENCE TO RELATED APPLICATIONS

This application claims the benefit of U.S. Provisional Patent Application Ser. No. 62/923,235 filed Oct. 18, 2019, which is expressly incorporated by reference herein.

2. BACKGROUND

Particular small molecules of the picolinamide structure are of interest as being effective against ascomycetes, basidiomycetes, deuteromycetes and oomycetes and are useful as fungicides for agricultural uses as described in WO Patent Application 2019173665 and U.S. patent application Ser. No. 16/296,324, both of which are expressly incorporated by reference herein.

Chiral compounds such as these picolinamides can often be a challenge to manufacture on an industrial scale due to the need to control the absolute and relative stereochemistry of the product and intermediates. Moreover, the costs involved in multi-step syntheses at scale may significantly increase costs for each additional step required. Thus, operationally simple and limited-step processes to manufacture biologically active compounds at scale are highly desirable.

Accordingly, there is a need in the field for better processes to synthesize optically active picolinamide compounds, especially those at scale. Such processes are advantageous in that they will improve the active ingredient impurity profile, lower commercial manufacturing costs and improve efficiency and atom economy.

3. SUMMARY

The structure of picolinamides of interest to this application follows the generic Formula A:

A

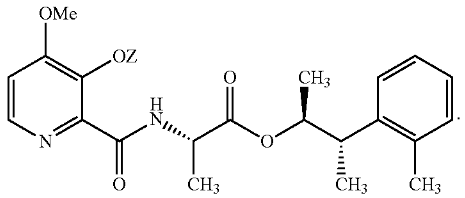

wherein Z is $CH_3CO$, $CH_3CH_2CO$ or $(CH_3)_2CHCO$.

These compounds may be made by coupling a compound of Formula B

B

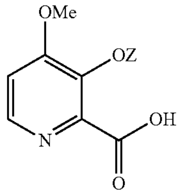

wherein Z is $CH_3CO$, $CH_3CH_2CO$ or $(CH_3)_2CHCO$; with at least one of the compounds of Formula C and Formula C1

C

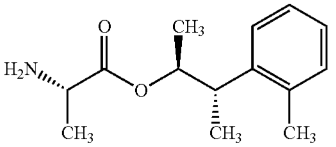

C1

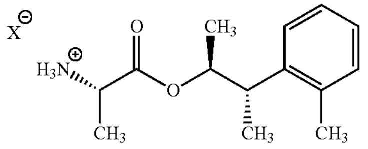

wherein X is Cl, Br, I, $HSO_4$, $H_2PO_4$, $CF_3COO$, or $CH_3SO_3$.

Another aspect of the present disclosure provides a process for the preparation of a compound of Formula B

B

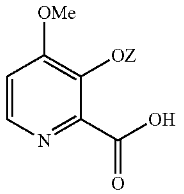

wherein Z is $CH_3CH_2CO$ comprising the steps of a) reacting a compound of Formula B, wherein Z is H with an acylating reagent, and a base; and b) isolating the compound of Formula B, wherein Z is $CH_3CH_2CO$ from the mixture. In some aspects, the disclosure provides a process wherein suitable acylating reagents may be selected from one of propionyl chloride and propionic anhydride, or mixtures thereof.

Another aspect of the present disclosure provides a process for the preparation of the compound of Formula C1:

C1

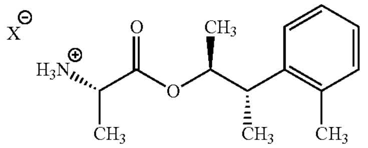

comprising the steps of a) creating a first mixture containing the compound of Formula G2 as predominantly a single enantiomer

G2

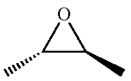

o-tolylmagnesium halide, and a copper catalyst;

b) isolating the compound D2

D2

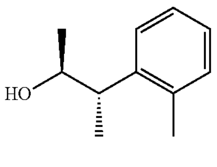

from the first mixture;

c) creating a second mixture containing the compound of Formula D2,

D2

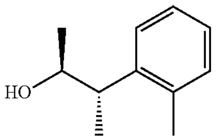

N-(tert-butoxycarbonyl)-L-alanine, an acylating agent, a catalyst and optionally a base;

d) isolating the compound of Formula F

F

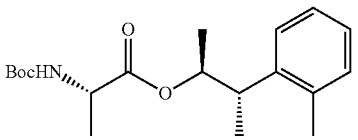

from the second mixture;

e) creating a third mixture containing the compound of Formula F and a strong acid;

wherein the strong acid is HCl, HBr, HI, $H_2SO_4$, $H_3PO_4$, $CF_3COOH$, or $CH_3SO_3H$; and f) isolating the compound of Formula C1 from the third mixture.

Another aspect of the present disclosure is the intermediate produced in the present process, viz., the compound:

B

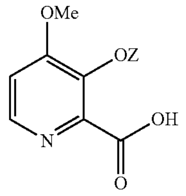

wherein Z is $CH_3CH_2CO$.

In one aspect, the resultant enantiomeric and/or diastereomeric enriched compounds are provided. In some aspects, processes that make enantiomeric and/or diastereomeric enriched Formula A and intermediates thereof are provided.

In some aspects, compounds or mixtures disclosed herein are enantiomeric and/or diastereomeric enriched synthetic intermediates of Formula A and/or are protected forms or intermediates of Formula A; that is the compound is masked with a protecting organic functional group that when exposed to the appropriate conditions will cleave the covalent bond from the protecting group to produce Formula A.

In further aspects, the processes described herein make a compound that is a useful intermediate. In further aspects, mixtures are made that comprise a high percentage of enantiomeric and/or diastereomeric enriched Formula A or intermediates thereof. In some aspects, the processes described herein provide very low concentrations of undesired enantiomeric and/or diastereomeric compounds. These organic compounds are impurities, i.e. side-products from addition reactions and/or are cumulative, meaning these compounds (impurities) are present because one or more impure intermediates were carried forward in steps for the total synthesis of the picolinamide.

In one aspect, the processes described herein provide a total synthesis for making enantiomeric and/or diastereomeric enriched Formula A. In some aspects, the disclosure provides enantiomeric and/or diastereomeric enriched protected forms of Formula A or intermediates thereof.

In some aspects, mixtures comprising one or more compounds or salts thereof disclosed herein are provided.

In various aspects, the disclosure herein provides a compound that is selected from among certain specific compounds disclosed herein. In some aspects, the compound is any one of the compounds that is reduced to practice in the Examples section of this disclosure.

In a still further aspect, methods of manufacture are provided.

4. DESCRIPTION

4.1. Definitions

Various terms used in the specification and claims herein are defined as set forth below, unless otherwise specifically defined in this disclosure. All technical and scientific terms not defined herein have the meaning commonly understood by a person skilled in the art to which this invention belongs.

"Enantiomeric and/or diastereomeric enriched" refers to the amount (mol %) of a particular desired compound in a mixture of organic compounds disclosed herein. The other, undesired organic compounds in the mixture may be the enantiomer or the diastereomer of the desired compound, and as such these enantiomers and/or diastereomers are impurities. Otherwise, the impurity or impurities may be any one or more of the organic compounds disclosed herein.

"Substantially pure or free" refers to a mixture in which one organic compound of interest far exceeds the amount of other small organic compounds in the mixture as impurities, and is at least 90%, at least 95%, at least 96%, at least 97%, at least 98%, at least 99%, at least 99.5%, at least 99.7%, at least 99.9%, by mol, of the desired compound.

"Pg or protecting group" refers to any organic functional group which is a mask or as is traditional known in the art, is a group that "protects" a certain organic functional group with the ability to form that certain functional group upon bond cleavage. Examples include, but are not limited to: TMS, TBDMS, TBDPS, Ms, Ns, Tf, Fmoc, Boc, Cbz, Troc, Alloc, acetyl

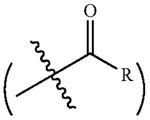

including acetamide where R=methyl or trifluoroacetamide where R=trifluouromethyl, hydroxylamine

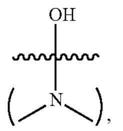

Tr or trityl (—$C(Ph)_3$), benzylidene

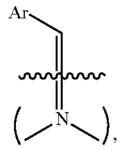

hydrazinyl

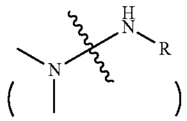

where R also can be C(O)R', benzoyl (—C(O)Ph), benzyl (—$CH_2Ph$), allyl, vinyl, $Bu^t$, and Piv. These groups, generally, are trivial to put on and there are many primary references in the literature to follow for the synthesis techniques, including the Wutz reference disclosed herein, which can assist the skilled artisan if they should need troubleshooting. Also, the skilled artisan will note that the groups referenced herein as "X" or "R" are a variety of organic functional groups that are selected from the group consisting of: alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein.

As used herein, the term "salt" refers to salts which are suitable for use in agriculture, i.e. they affect humans and lower animals without undue toxicity, irritation, allergic response and the like, and are commensurate with a reasonable benefit/risk ratio in agriculture. These salts are well known in the art. Salts of the compounds described herein include those derived from suitable inorganic and organic acids and bases. Examples of acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecyl sulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium salts. Representative alkali or alkaline earth metal salts include sodium, lithium, potassium, calcium, magnesium, and the like. Further acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

4.2. Additional Interpretational Conventions

Generally, reference to or depiction of a certain element such as hydrogen or H is meant to include all isotopes of that element. For example, if an R group is defined to include hydrogen or H, it also includes deuterium and tritium. Compounds comprising radioisotopes such as tritium and $^{14}C$ are thus within the scope of the present technology. Procedures for inserting such labels into the compounds of the present technology will be readily apparent to those skilled in the art based on the disclosure herein.

Unless the specific stereochemistry is expressly indicated, all chiral, diastereomeric, and racemic forms of a compound are intended. Thus, compounds described herein include enriched or resolved optical isomers at any or all asymmetric atoms as are apparent from the depictions. Racemic mixtures, and d or 1 enriched stereomeric mixtures, as well as the individual optical isomers can be isolated or synthesized so as to be substantially free of their enantiomeric or diastereomeric partners, and these stereoisomers are all within the scope of the present technology.

The compounds described herein may exist as solvates, especially hydrates, and unless otherwise specified, all such solvates and hydrates are intended. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates, among others. The identification and preparation of any particular solvate is within the skill of the ordinary artisan of synthetic organic or medicinal chemistry.

Throughout this application, the text refers to various aspects of the present compounds, compositions, and methods. The various aspects described are meant to provide a variety of illustrative examples and should not be construed as descriptions of alternative species. Rather, it should be noted that the descriptions of various aspects provided herein may be of overlapping scope. The aspects discussed herein are merely illustrative and are not meant to limit the scope of the present technology.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some aspects, ±100% in some aspects ±50%, in some aspects ±20%, in some aspects ±10%, in some aspects ±5%, in some aspects ±1%, in some aspects ±0.5%, and in some aspects ±0.1% from the specified amount, as such variations are appropriate to perform the disclosed methods or employ the disclosed compositions.

As used herein and in the appended claims, singular articles such as "a," "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g. "such as") provided herein, is intended merely to better illuminate the aspects and does not pose a limitation on the scope of the claims unless otherwise stated. No language in the specification should be construed as indicating any non-claimed element as essential.

4.3. Processes

In the processes described herein, the picolinamide of Formula A

A

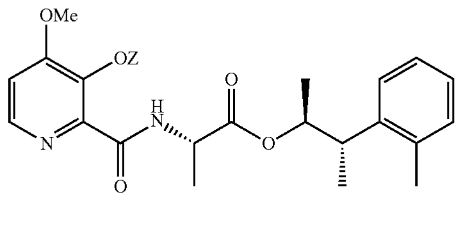

wherein Z is $CH_3CO$, $CH_3CH_2CO$ or $(CH_3)_2CHCO$, may be prepared by coupling a compound of Formula B

B

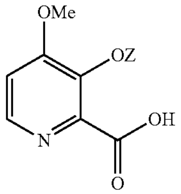

wherein Z is $CH_3CO$, $CH_3CH_2CO$ or $(CH_3)_2CHCO$; with at least one of the compounds of Formula C and Formula C1

C

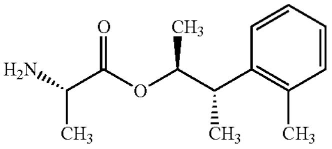

C1

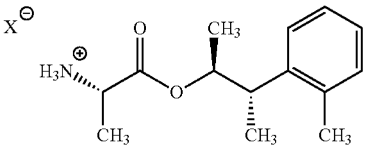

wherein X is Cl, Br, I, $HSO_4$, $H_2PO_4$, $CF_3COO$, or $CH_3SO_3$.

4.3.1. Preparation of Compound of Formula A

In a first aspect, the disclosure provides for a process for the preparation or manufacture of the compound of Formula A

A

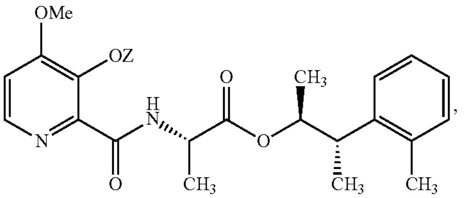

wherein Z is $CH_3CO$, $CH_3CH_2CO$ or $(CH_3)_2CHCO$, the process comprising contacting the following components:

a compound of Formula B:

B

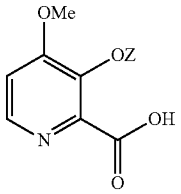

or a salt thereof, a compound of Formula C:

C

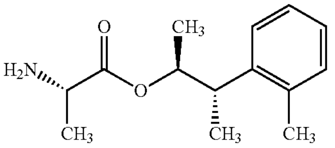

or a salt thereof, a coupling reagent, and a base.

In some aspects, the disclosure provides a process wherein the coupling reagent is pivaloyl chloride.

In some aspects, the disclosure provides for a process of manufacturing Formula A wherein the process comprises:

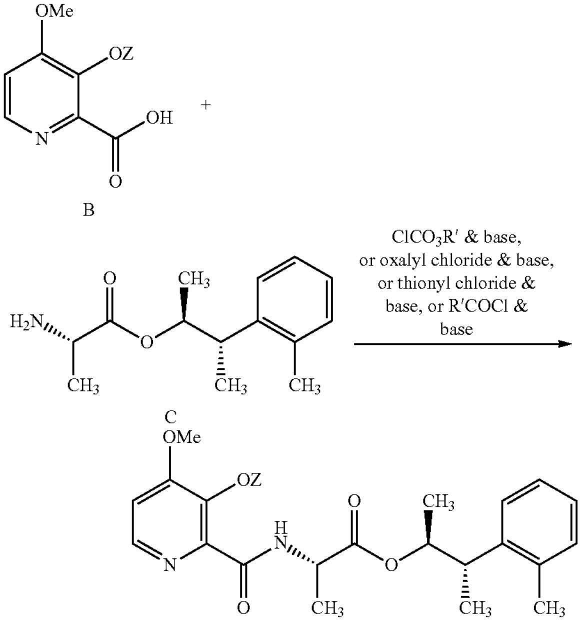

B

C

A wherein Z is $CH_3CO$, $CH_3CH_2CO$ or $(CH_3)_2CHCO$. Picolinic acid B is first activated for coupling by converting it into (a) the corresponding mixed anhydride using an alkyl, aryl or benzyl chloroformate and a base, or a carboxylic acid chloride and a base, or (b) the corresponding acid chloride using oxalyl chloride or thionyl chloride. The resulting derivative of picolinic acid B, in the form of a mixed anhydride or an acid chloride, can be treated with the amine salt of Formula C, wherein X is Cl, Br, I, $HSO_4$, $H_2PO_4$, $CF_3COO$, or $CH_3SO_3$, and a base to provide the desired picolinamide of Formula A, wherein Z is $CH_3CO$, $CH_3CH_2CO$ or $(CH_3)_2CHCO$. The compound of Formula A may be isolated by employing standard isolation and purification techniques. Suitable solvents for this process may include one or more of dichloromethane (DCM), 1,2-dichloroethane (DCE), acetonitrile. Suitable chloroformate esters (i.e., $ClCO_2R'$) for use in the process may include those wherein R' is a $C_1$-$C_4$ alkyl; an aryl or a benzyl group. Suitable acid chlorides (i.e., R'COCl) for use in the process may include those wherein R' is a $C_1$-$C_4$ alkyl.

In some aspects, the salt of a compound of Formula C:

C

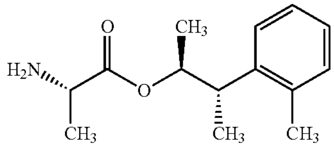

is a salt where the structure is a compound of Formula C1

C1

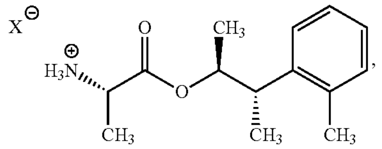

wherein X is Cl, Br, I, $HSO_4$, $H_2PO_4$, $CF_3COO$ or $CH_3SO_3$.

In some aspects, the disclosure provides a process wherein the organic amine is triethylamine. In some aspects, the disclosure provides a process wherein the organic amine is (1,4-diazabicyclo[2.2.2]octane) (DABCO). In some aspects, the disclosure provides a process wherein the organic amine is N-methylimidazole (NMI). In some aspects, the disclosure provides a process wherein the organic amine is imidazole. In some aspects, the disclosure provides a process wherein organic amine is 4-pyrrolidinopyridine (PPY). In some aspects, the disclosure provides a process wherein the organic amine is Quinidine, or an analog thereof. In some aspects, the disclosure provides a process wherein the organic amine is diisopropylethylamine (DIPEA), aromatic amines such as pyridine, metal carbonates such as potassium carbonate, and mixtures thereof.

In some aspects, the disclosure provides a process wherein the organic amine is selected from the group consisting of: DMAP, PPY, Quinidine diisopropylethylamine (DIPEA), pyridine, potassium carbonate, NMI, and mixtures thereof.

In various aspects, the disclosure provides for a method of manufacture of a compound according to any one of the aspects disclosed herein. In various aspects, the disclosure provides for a method of manufacture of a compound wherein the process for the manufacture is any one of the process aspects described herein.

4.3.2. Preparation of Compound of Formula B

In some aspects, the disclosure provides a process wherein the compound of Formula B, wherein Z is CH3CO, CH3CH2CO or (CH3)2CHCO, may be prepared by acylation of the compound of Formula B, wherein Z is H, with an acylating reagent, base and optionally a catalyst.

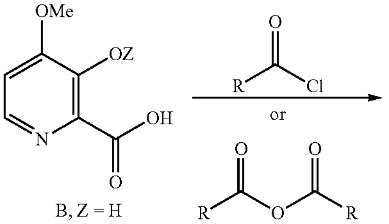

B, Z = H

-continued

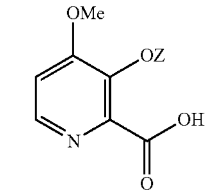

B, Z = $CH_3CO$, $CH_3CH_2CO$, $(CH_3)_2CHCO$

In some aspects, the disclosure provides a process wherein suitable acylating reagents may include those wherein R is a C1-C3 alkyl, including acetyl chloride, acetic anhydride, propionyl chloride, propionic anhydride, isobutyryl chloride and isobutyric anhydride. Bases may be selected from pyridine, alkyl substituted pyridines, and trialkylamines, such as triethylamine. Suitable catalysts for this process include, but are not limited to, DMAP (4-(dimethylamino)pyridine) and NMI (N-methyl imidazole). Suitable solvents for this transformation may include DCM, THF, MeTHF, CPME, heptanes, hexanes, toluene and mixtures thereof. The compound of Formula B may be isolated by employing standard isolation and purification techniques.

4.3.3. Preparation of Compounds of Formula C and C1

In some aspects, the disclosure provides a process wherein the compound of Formula C1, wherein X is Cl, Br, I, HSO4, H2PO4, CF3COO, or CH3SO3, may be prepared in a process that comprises the following steps:

a) creating a first mixture containing the compound of Formula G2 as predominantly a single enantiomer

G2

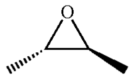

o-tolylmagnesium halide, and a copper catalyst;

b) isolating the compound of Formula D2

D2

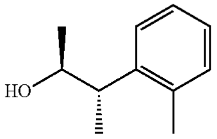

from the first mixture.

c) creating a second mixture containing the compound of Formula D2, N-(tert-butoxycarbonyl)-L-alanine, an acylating agent, a catalyst and optionally a base;

d) isolating the compound of Formula F

F

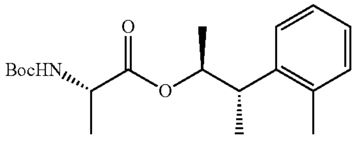

from the second mixture;

e) creating a third mixture containing the compound of Formula F and a strong acid;

wherein the strong acid is HCl, HBr, HI, $H_2SO_4$, $H_3PO_4$, $CF_3COOH$, or $CH_3SO_3H$; and f) isolating the compound of Formula C1 from the third mixture.

In some aspects, the disclosure provides a process to prepare a compound of Formula D2, wherein the o-tolylmagnesium halide is o-tolylmagnesium chloride, o-tolylmagnesium bromide and mixtures thereof. Suitable copper catalysts include, but are not limited to, copper salts such as copper (I) iodide, copper (I) bromide and copper (I) chloride. Suitable solvents for this transformation may include THF, MeTHF, CPME, MTBE, heptanes, hexanes, toluene and mixtures thereof.

In some aspects, the disclosure provides a process to prepare the o-tolylmagnesium halide from magnesium and 2-halotoluene derivatives, such as 2-chlorotoluene and 2-bromotoluene.

In some aspects, the disclosure provides a process to prepare a compound of Formula F, wherein suitable acylating agents include, but are not limited to, acid chlorides such as pivaloyl chloride and acid anhydrides such as pivalic anhydride. Suitable catalysts for this process include, but are not limited to, DMAP (4-(dimethylamino)pyridine) and NMI (N-methyl imidazole). Suitable bases may include, but are not limited to, trialkylamines such as triethylamine or diisopropylethylamine. Suitable solvents for this transformation may include, but are not limited to, DCM, THF, MeTHF, CPME, MTBE, ethyl acetate, heptanes, heptane, hexanes, toluene and mixtures thereof.

In some aspects, the disclosure provides a process to prepare a compound of Formula C or a compound of Formula C1, wherein X is Cl, Br, I, HSO4, H2PO4, CF3COO, or CH3SO3. Suitable solvents for this transformation may include, but are not limited to, dioxane, CPME, heptanes, heptane hexanes, toluene, methanol, ethanol, isopropanol and mixtures thereof.

The compound of Formula C1, may be prepared in an alternative process that comprises the following steps:

a) creating a first mixture containing the compounds of Formula G1 and G2 as a racemic mixture of (R,R)- and (S,S)-enantiomers, b)

G1

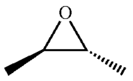

and

G2

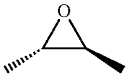

o-tolylmagnesium halide, and a copper catalyst;

c) isolating a second mixture containing the compounds of Formula D1 and D2 as a racemic mixture of (R,R)- and (S,S)-enantiomers

D1

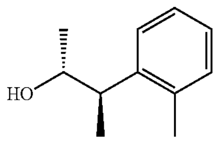

and

-continued

D2

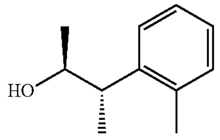

d) creating a third mixture containing the compounds D1 and D2 as a racemic mixture of (R,R)- and (S,S)-enantiomers, a lipase enzyme, and an acyl donor;

e) isolating the compound of Formula D2 as a fourth mixture containing the compound of Formula E1

D2

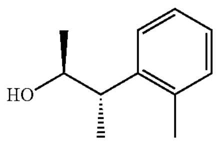

and

E1

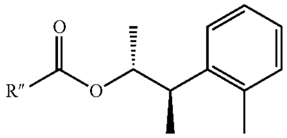

wherein R" is $C_1$-$C_{18}$ alkyl;

f) creating a fifth mixture containing the compound of Formula D2, the compound of Formula E1, wherein R" is $C_1$-$C_{18}$ alkyl; N-(tert-butoxycarbonyl)-L-alanine, an acylating agent, a catalyst and optionally a base;

g) isolating the compound of Formula F as a sixth mixture containing the compound of Formula E1, wherein R" is $C_1$-$C_{18}$ alkyl;

F

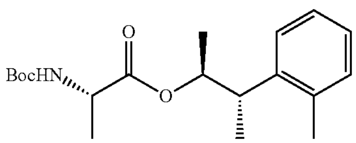

and

E1

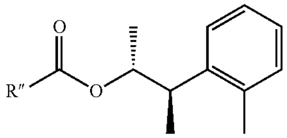

from the fifth mixture;

h) creating a seventh mixture containing the compound of Formula F, the compound of Formula E1, wherein R" is $C_1$-$C_{18}$ alkyl; and a strong acid;

wherein the strong acid is HCl, HBr, HI, $H_2SO_4$, $H_3PO_4$, $CF_3COOH$, or $CH_3SO_3H$; and i) isolating the compound of Formula C1 from the seventh mixture.

In some aspects, the disclosure provides a process to prepare a mixture containing the compounds D1 and D2 as a racemic mixture of (R,R)- and (S,S)-enantiomers, wherein the o-tolylmagnesium halide is o-tolylmagnesium chloride, o-tolylmagnesium bromide and mixtures thereof. Suitable copper catalysts include, but are not limited to, copper salts such as copper (I) iodide, copper (I) bromide, and copper (I) chloride. Suitable solvents for this transformation may include THF, MeTHF, CPME, heptanes, hexanes, toluene and mixtures thereof.

In some aspects, the disclosure provides a process to prepare the o-tolylmagnesium halide from magnesium and 2-halotoluene derivatives, such as 2-chlorotoluene and 2-bromotoluene.

In some aspects, the disclosure provides a process to prepare a compound of Formula D2, wherein suitable lipase enzymes include, but are not limited to, *Candida antarctica* Lipase B, *Burkholderia cepacia, Candida rugosa, Pseudomonas cepacia, Thermomyces lanuginosus, Rhizomucor miehei, Rhizopus oryzae*. The lipase enzymes could be free or immobilized such as different preparations of immobilized Cal B (Novozym® 435, Cal B Immo Plus™, etc). Suitable acyl donors may include, but are not limited to, isopropenyl acetate and unbranched $C_1$-$C_{18}$ vinyl acetates including vinyl acetate. Suitable solvents for this transformation may include, but are not limited to, toluene, heptane, heptanes, hexane, hexanes, MTBE (methyl tert-butyl ether), CPME (cyclopentyl methyl ether), THF, Me-THF and mixtures thereof.

In some aspects, the disclosure provides a process to prepare a compound of Formula F, wherein suitable acylating agents include, but are not limited to, acid chlorides such as pivaloyl chloride or acid anhydrides such as pivalic anhydride. Suitable catalysts for this process include, but are not limited to, DMAP (4-(dimethylamino)pyridine) and NMI (N-methyl imidazole). Suitable bases may include, but are not limited to, trialkylamines such as triethylamine or diisopropylethylamine. Suitable solvents for this transformation may include, but are not limited to, DCM, THF, MeTHF, CPME, MTBE, ethyl acetate, heptanes, heptane, hexanes, toluene and mixtures thereof.

In some aspects, the disclosure provides a process to prepare a compound of Formula C or a compound of Formula C1, wherein X is Cl, Br, I, HSO4, H2PO4, CF3COO, or CH3SO3. Suitable solvents for this transformation may include, but are not limited to, dioxane, CPME, heptanes, heptane hexanes, toluene, methanol, ethanol, isopropanol and mixtures thereof.

In some aspects, the disclosure above provides a process wherein the compound of Formula C

C

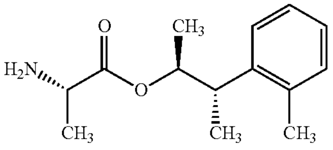

may be prepared.

In some aspects, the disclosure provides a process wherein the mixture of compounds of Formula D2 and Formula E1,

E1

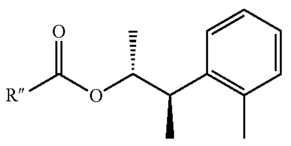

and

-continued

D2

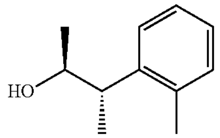

wherein R" is $C_1$-$C_{18}$ alkyl, may be used without purification. In another aspect, the disclosure provides a process wherein the compound of Formula D2 may be isolated by employing standard isolation and purification techniques.

In some aspects, the disclosure provides a process wherein the mixture of compounds of Formula F and Formula E1

E1

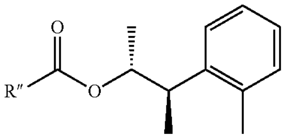

and

F

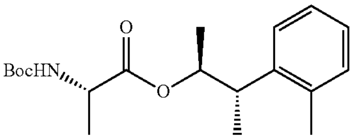

may be used without purification. In another aspect, the disclosure provides a process wherein the compound of Formula F may be isolated by employing standard isolation and purification techniques.

4.3.4. Preparation of Compound of Formula G

In some aspects, the disclosure provides a process to prepare a compound of Formula G (trans-2,3-epoxybutane) from meso-2,3-butanediol:

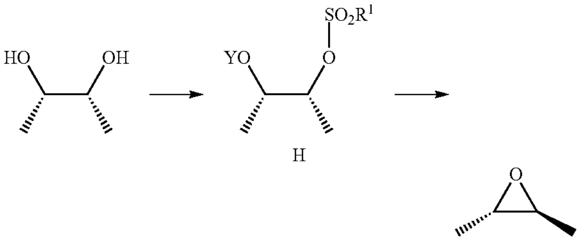

H

G wherein $R^1$ is alkyl, alkoxy or aryl, and Y is H or CO2R'", wherein R'" is alkyl or aryl. meso-2,3-Butanediol is first converted into a sulfate or sulfonic ester (H). Depending on the conditions used, these transformations can be accomplished to afford racemic or enantioenriched sulfonic ester products of Formula G. The sulfate or sulfonic esters H are treated with base to give (racemic or enantioenriched) trans-2,3-epoxybutane (G).

In some aspects, the disclosure provides a process in which a compound of Formula H, wherein $R^1$ is alkyl, alkoxy or aryl, and Y is H, is prepared by sulfonylation of meso-2,3-butanediol with a copper catalyst, a bisoxazoline ligand, a sulfonyl halide and a base. Suitable copper catalysts for this process include, but are not limited to, copper salts such as copper (II) chloride, copper (II) bromide, copper (II) triflate and copper (II) acetate. Suitable bisoxazoline ligands for this process include a compound of Formula I,

I

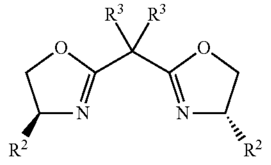

wherein $R^2$ is $C_1$-$C_{18}$ alkyl or aryl, and $R^3$ is H or $C_1$-$C_4$ alkyl. Suitable sulfonyl halides include, but are not limited to, methanesulfonyl chloride, benzenesulfonyl chloride and toluenesulfonyl chloride. Suitable bases include, but are not limited to, an inorganic base such as sodium hydride, ammonium hydroxide, sodium hydroxide, potassium hydroxide, lithium hydroxide, sodium carbonate, potasium carbonate, cesium carbonate, potassium phosphate, sodium phosphate, or an organic base such as triethyl amine, trimethyl amine, diisopropyl ethyl amine (DIEA), pyridine, picoline, 1,8-Diazabicyclo(5.4.0)undec-7-ene (DBU). Suitable solvents for this transformation include, but are not limited to, DCM, dichloroethane, chloroform, chlorobenzene, THF, MeTHF, CPME, heptanes, hexanes, toluene, tert-amyl alcohol, tert-butanol and mixtures thereof. Other methods to prepare a compound of Formula H, wherein $R^1$ is alkyl, alkoxy or aryl, and Y is H, may include methods disclosed in: (1) *Tetrahedron Lett.* 2007, 48, 7605-7609, and (2) JP5108383.

In some aspects, the disclosure provides a process wherein the compound of Formula H, wherein $R^1$ is alkyl, alkoxy or aryl, and Y is H, may be used without purification. In another aspect, the disclosure provides a process wherein the compound of Formula H, wherein $R^1$ is alkyl, alkoxy or aryl, and Y is H, may be isolated by employing standard isolation and purification techniques.

In some aspects, the disclosure provides a process wherein the compound of Formula G is prepared from a compound of Formula H, wherein $R^1$ is alkyl, alkoxy or aryl, and Y is H, with a base. Suitable bases include, but are not limited to, an inorganic base such as sodium hydride, ammonium hydroxide, sodium hydroxide, potassium hydroxide, lithium hydroxide, sodium carbonate, potassium carbonate, cesium carbonate, potassium phosphate, sodium phosphate, or an organic base such as triethyl amine, trimethyl amine, diisopropyl ethyl amine (DIEA), pyridine, picoline, 1,8-Diazabicyclo(5.4.0)undec-7-ene (DBU).

In some aspects, the disclosure provides a process wherein the compound of Formula G, may be used without purification. In another aspect, the disclosure provides a process wherein the compound of Formula G, may be isolated by employing standard isolation and purification techniques.

4.3.5. Preparation of Compound of Formula I

In some aspects, the disclosure provides a process to prepare a compound of Formula I

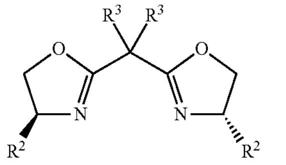

I wherein $R^2$ is C1-C18 alkyl or aryl, and $R^3$ is H or C1-C4 alkyl. In some aspects, the disclosure provides a process to prepare a compound of Formula I from malononitrile:

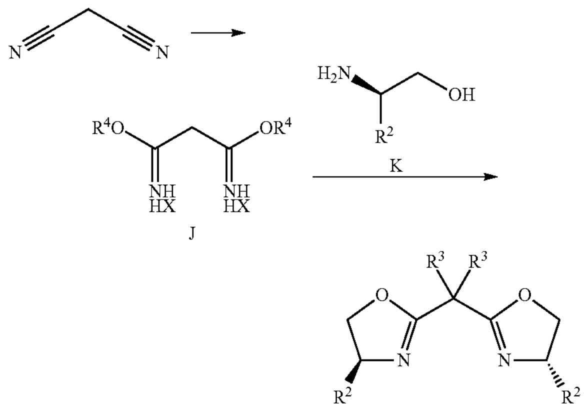

J

I wherein $R^2$ is C1-C18 alkyl or aryl, and $R^3$ is H. Malononitrile is first converted into a compound of Formula J, wherein $R^4$ is C1-C4 alkyl, and X is Cl, Br, I, HSO4, H2PO4, CF3COO, CH3COO or CH3SO3. The compound of Formula J, wherein $R^4$ is C1-C4 alkyl, and X is Cl, Br, I, HSO4, H2PO4, CF3COO, CH3COO or CH3SO3, is treated with a compound of Formula K, wherein $R^2$ is C1-C18 alkyl or aryl, to give a compound of Formula I, wherein $R^2$ is C1-C18 alkyl or aryl, and $R^3$ is H.

In some aspects, the disclosure provides a process in which a compound of Formula J, wherein $R^4$ is C1-C4 alkyl, and X is Cl, Br, I, HSO4, H2PO4, CF3COO, CH3COO or CH3SO3, is prepared from malononitrile with an acid and alcohol. Suitable acids for this process include, but are not limited to, HCl, HBr, HI, $H_2SO_4$, $H_3PO_4$, $CF_3COOH$, or $CH_3SO_3H$. Suitable forms of HCl may include HCl in solvent, HCl gas and HCl generated in-situ from acetyl chloride. Suitable alcohols include, but are not limited to, methanol, ethanol, propanol and butanol. Suitable solvents for this transformation include, but are not limited to, DCM, dichloroethane, chloroform, chlorobenzene, THF, MeTHF, CPME, dioxane, heptanes, hexanes, toluene, benzene, tert-amyl alcohol, tert-butanol, ethanol, and mixtures thereof. Other methods to prepare a compound of Formula J, wherein $R^4$ is C1-C4 alkyl, and X is Cl, Br, I, HSO4, H2PO4, CF3COO, CH3COO or CH3SO3, may include methods disclosed in: (1) Org. Lett. 2018, 20, 154, (2) Chem. Eur. J. 2013, 19, 8136, (3) Nature Chem. 2017, 9, 970, (4) Inorganic Chem., 2003, 42, 2950, (5) Archiv der Pharmazie, 1988, 321, 863.

In some aspects, the disclosure provides a process wherein the compound of Formula J, wherein $R^4$ is C1-C4 alkyl, and X is Cl, Br, I, HSO4, H2PO4, CF3COO, CH3COO or CH3SO3, may be used without purification. In another aspect, the disclosure provides a process wherein the compound of Formula J, wherein $R^4$ is C1-C4 alkyl, and X is Cl, Br, I, HSO4, H2PO4, CF3COO, CH3COO or CH3SO3, may be isolated by employing standard isolation and purification techniques.

In some aspects, the disclosure provides a process in which a compound of Formula I, wherein $R^2$ is C1-C18 alkyl or aryl, and $R^3$ is H, is prepared from a compound of Formula J, wherein $R^4$ is C1-C4 alkyl, and X is Cl, Br, I, HSO4, H2PO4, CF3COO, CH3COO or CH3SO3, and a compound of Formula K, wherein $R^2$ is C1-C18 alkyl or aryl. Suitable solvents for this transformation include, but are not limited to, DCM, dichloroethane, chloroform, chlorobenzene, THF, MeTHF, CPME, dioxane, heptanes, hexanes, toluene, benzene and mixtures thereof. Other methods to prepare a compound of Formula I, wherein $R^2$ is C1-C18 alkyl or aryl, and $R^3$ is H, may include methods disclosed in: (1) Org. Lett. 2018, 20, 154, (2) Organometallics, 2019, 38, 3852.

In some aspects, the disclosure provides a process wherein the compound of Formula I, wherein $R^2$ is C1-C18 alkyl or aryl, and $R^3$ is H, may be used without purification. In another aspect, the disclosure provides a process wherein the compound of Formula I, wherein $R^2$ is C1-C18 alkyl or aryl, and $R^3$ is H, may be isolated by employing standard isolation and purification techniques.

4.3.6. Reaction Conditions for Processes

In some aspects, the disclosure provides a process wherein organic solvent is used and the organic solvent is aprotic.

In some aspects, the process uses organic solvent that is heptanes, dichloromethane, hexanes, cyclohexane, toluene, acetonitrile, tetrahydrofuran, 2-methylhydrofuran, ethyl acetate, dichloromethane (DCM), dichloroethane (DCE), dichlorobenzene, trifluorotoluene or methylcyclohexane tetrahydrofuran (THF), 2-tetrahydrofuran (2-MeTHF), DME, or dioxane or mixtures thereof.

In some aspects, the process uses organic solvent that is a mixture that contains an aprotic organic solvent selected from the group consisting of: hepantes, THF (tetrahydrofuran), diethyl ether and mixtures thereof.

In some aspects, the disclosure provides a process wherein the process includes one or more organic co-solvents. In some aspects, the disclosure provides a process wherein the mixture contains dimethylformamide (DMF) as a solvent. In some aspects, the disclosure provides a process wherein the mixture contains dimethylformamide (DMF) as a solvent and a co-solvent. In some aspects, the disclosure provides a process wherein the mixture contains heptanes as a solvent and a co-solvent. In some aspects, the disclosure provides a process wherein the mixture contains heptanes as a solvent and THF co-solvent. In some aspects, the disclosure provides a process wherein the mixture contains heptanes as a solvent and DCM co-solvent.

In some aspects, a process is provided wherein the process further comprises heating of the mixture. In some aspects, the heating is performed to no more than 25° C., 26° C., 27° C., 28° C., 29° C., 30° C., 40° C., 50° C., 60° C., 70° C., 80° C., 90° C., 100° C., 110° C., or 120° C.

In some aspects, a process is provided wherein the process further comprises cooling of the mixture. In some aspects, the cooling is performed to no more than −20° C., −10° C., −5° C., 0° C., 5° C., 10° C., 15° C., 20° C., or 22° C.

The starting materials for the following reactions are generally known compounds or can be prepared by known procedures or obvious modifications thereof. For example, many of the starting materials are available from commercial suppliers such as Aldrich Chemical Co. (Milwaukee, Wisconsin, USA), Bachem (Torrance, California, USA), Emka-Chemce or Sigma (St. Louis, Missouri, USA), CombiChem (San Diego, CA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

It will also be appreciated that where typical process conditions (i.e. reaction temperatures, times, mole ratios of reactants, solvents, pressures, etc.) are given to make these compounds, minor modifications to these process conditions can also be used unless otherwise stated. Optimum reaction conditions may vary with the particular reactant or solvent used, but such conditions can be determined by one skilled in the art by routine optimization procedures as long as the reagents stay the same. In some aspects, the process can be performed in a packed bed reactor in a continuous flow mode or recirculation mode. In some aspects, the process can also be performed in a continuous stirred-tank reactor in a recirculation mode.

Additionally, as will be apparent to those skilled in the art, conventional protecting groups may be necessary to prevent certain functional groups from undergoing undesired reactions. Herein it is understood that amino, keto, thio, hydroxyl, and any other necessary protecting groups and their methods of deprotection are known in the art, such as those described in T. W. Greene and P. G. M. Wutz, Protecting Groups in Organic Synthesis, Third Edition, Wiley, New York, 1999, which is incorporated in its entirety along with the references cited therein.

If the compounds described herein contain one or more chiral centers, such compounds can be prepared or isolated as pure stereoisomers, i.e. as individual enantiomers or d(1) stereoisomers, or as stereoisomer-enriched mixtures. All such stereoisomers (and enriched mixtures) are included within the scope of the present technology, unless otherwise indicated. Pure stereoisomers (or enriched mixtures) may be prepared using, for example, optically active starting materials or stereoselective reagents well known in the art. Alternatively, racemic mixtures of such compounds can be separated using, for example, chiral column chromatography, chiral resolving agents and the like.

In some aspects, compound mixtures are provided that comprise at least two or more compounds as described herein and are enantiomerically and/or diastereomerically enriched with a compound of formula A with an impurity from 0.01% to: no more than 0.1 mol %, no more than 0.5 mol %, no more than 1 mol %, no more than 2 mol %, no more than 3 mol %, no more than 4 mol %, no more than 5%, no more than 10%, or no more than 15%. In some aspects, mixtures are enriched by about 85%, 90%, 95%, 96%, 97%, 98%, 99%, 99.5%, 99.7% or 99.9% enantiomeric excess (ee). In some aspects, mixtures are enriched by about 85%, 90%, 95%, 96%, 97%, 98%, 99%, 99.5%, 99.7% or 99.9% diastereomeric excess (de).

In certain aspects, the compound mixture comprises one or more compounds as described herein, and FORMULA A or salt thereof.

The skilled artisan will appreciate that these percentages for purity are based and calculated from the desired compound. Such determinations are routine in the field and examples can be found in syntheses and descriptions in the texts and references that have been cited herein.

5. EXAMPLES

The following synthetic examples are offered to illustrate this the present technology and are not to be construed in any way as limiting the scope of this the present technology. Unless otherwise stated, all temperatures are in degrees Celsius.

The examples are offered for illustrative purposes only and are not intended to limit the scope of the present invention in any way. Efforts have been made to ensure accuracy with respect to numbers used (e.g. amounts, temperatures, etc.), but some experimental error and deviation should, of course, be allowed for.

The practice of the present invention will employ, unless otherwise indicated, conventional methods of synthetic organic chemistry, protein chemistry and biochemistry and agriculture are within the skill of the art. Such techniques are explained fully in the literature. See, e.g. T. E. Creighton, Proteins: Structures and Molecular Properties (W. H. Freeman and Company, 1993); A. L. Lehninger, Biochemistry (Worth Publishers, Inc., current addition); Methods In Enzymology (S. Colowick and N. Kaplan eds., Academic Press, Inc.); Remington's Agricultural Sciences, 18th Edition (Easton, Pennsylvania: Mack Publishing Company, 1990); Carey and Sundberg Advanced Organic Chemistry 3rd Ed. (Plenum Press) Vols A and B(1992), and Organic Reactions, Volumes 1-40 (John Wiley, and Sons, 1991).

The present technology is further understood by reference to the following examples, which are intended to be purely exemplary of the present technology. The present technology is not limited in scope by the exemplified aspects, which are intended as illustrations of single aspects of the present technology only. Any methods that are functionally equivalent are within the scope of the present technology. Various modifications of the present technology in addition to those described herein will become apparent to those skilled in the art from the foregoing description and accompanying figures. Such modifications fall within the scope of the appended claims.

In the examples below, the following abbreviations have the following meanings. If an abbreviation is not defined, it has its generally accepted meaning.

aq. =aqueous
LC-MS=liquid chromatography-mass spectrometry
MS=mass spectrometry
THF=tetrahydrofuran
$NaHCO_3$=sodium bicarbonate
DIEA=diisopropylethylamine
MS=mass spectrometry
NaH=sodium hydride
o/n=overnight
HATU=1-[Bis(dimethylamino)methylene]-1H-1,2,3-trIzolo[4,5-b]pyridinium 3-oxid hexafluorophosphate
r. t.=room temperature
LAH=lithium aluminum hydride
DCM=dichloromethane
DMF=dimethylformamide
DMSO=dimethyl sulfoxide equiv.=equivalent
EtOAc=ethyl acetate
EtOH=ethanol
g=gram
h=hours
HCl=hydrochloric acid
HPLC=high-performance liquid chromatography
HOAc=acetic acid
M=molar
MeOH=methanol
mg=milligrams
mL=milliliters
mmol=millimols
mp=melting point
m/z=mass to charge ratio
NaCl=sodium chloride
$Na_2CO_3$=sodium carbonate
NMR=nuclear magnetic resonance
NaOH=sodium hydroxide
$Na_2SO_4$=sodium sulfate
TLC=thin layer chromatography
tAmOH=tert-amyl alcohol
Bs=benzene sulfonate
Ts=4-toluenesulfonate
UV=ultraviolet
wt %=weight percent
PM=micromolar

5.1. Example 1: Synthesis of Formula A

General Experimental Details:

Final compounds were confirmed by HPLC/MS analysis and determined to be ≥90%. $^1$H and $^{13}$C NMR spectra were recorded in $CDCl_3$ (residual internal standard $CHCl_3$=δ 7.26), DMSO-$d_6$ (residual internal standard $CD_3SOCD_2H$=δ 2.50), methanol-$d_4$ (residual internal standard $CD_2HOD$=δ 3.20), or acetone-$d_6$ (residual internal standard $CD_3COCD_2H$=δ 2.05). The chemical shifts (6) reported are given in parts per million (ppm) and the coupling constants (J) are in Hertz (Hz). The spin multiplicities are reported as s=singlet, bs=broad singlet, bm=broad multiplet, d=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

Compound Characterization

Synthetic Transformations

Example A1.1 (2S,3S)-3-(o-tolyl)butan-2-yl (3-acetoxy-4-methoxypicolinoyl)-L-alaninate

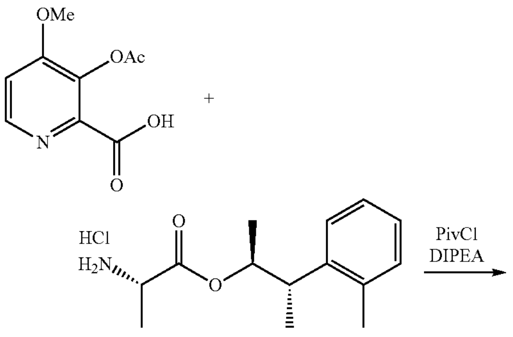

-continued

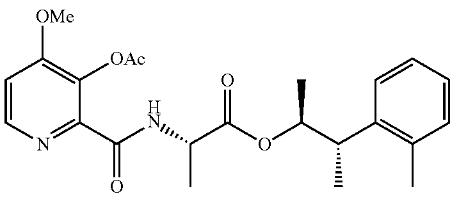

A 1 L three-neck flask equipped with a temperature probe, nitrogen inlet, and mechanical stirrer was charged with 3-acetoxy-4-methoxypicolinic acid (21.2 g, 100 mmol) and DCM (250 mL). The suspension was cooled to 0° C. and triethylamine (29.2 mL, 210 mmol) was slowly added via syringe. This suspension was mixed for 30 min until the suspension became a homogeneous solution. Pivaloyl chloride (11.75 mL, 95 mmol) was then added slowly via syringe. This mixture was allowed to stir for 30 minutes. A solution of (2S,3S)-3-(o-tolyl)butan-2-yl L-alaninate hydrochloride (22.45 g, 95 mmol) in DCM (212 mL) was added dropwise. The reaction was stirred at 0° C. for 60 minutes.

The crude reaction mixture was quenched with saturated aqueous sodium bicarbonate and stirred for 10 minutes. The layers were separated and the organic layer was washed with a 1:1 mixture of brine: 1 N HCl. The layers were separated and the organic layer was dried over anhydrous sodium sulfate, filtered and concentrated to a dark brown oil. The crude material was purified via silica gel chromatography (gradient ethyl acetate in hexanes) to afford the title compound (31.5 g, 77% yield) as an off-white semi-solid.

1H NMR (500 MHz, Chloroform-d) δ 8.66-8.47 (m, 1H), 8.33 (d, J=5.4 Hz, 1H), 7.21-7.05 (m, 4H), 7.00 (d, J=5.5 Hz, 1H), 5.14 (dq, J=8.4, 6.2 Hz, 1H), 4.73 (p, J=7.3 Hz, 1H), 3.89 (s, 3H), 3.19 (dq, J=8.4, 6.9 Hz, 1H), 2.40 (s, 3H), 2.35 (s, 3H), 1.51 (d, J=7.2 Hz, 3H), 1.25 (d, J=6.9 Hz, 3H), 1.12 (d, J=6.3 Hz, 3H); 13C NMR (126 MHz, Chloroform-d) δ 170.5, 167.1, 160.5, 157.6, 144.9, 139.9, 139.6, 135.6, 133.6, 128.6, 124.5, 124.4, 108.0, 74.4, 54.4, 46.3, 37.9, 18.9, 18.1, 16.9, 16.6, 15.6 [one signal missing due to incidental equivalence]; HRMS-ESI (m/z) $[M+H]^+$ calcd for C23H28N2O6, 429.2020. found, 429.2017.

Example A1.2 (2S,3S)-3-(o-tolyl)butan-2-yl (4-methoxy-3-(propionyloxy)picolinoyl)-L-alaninate

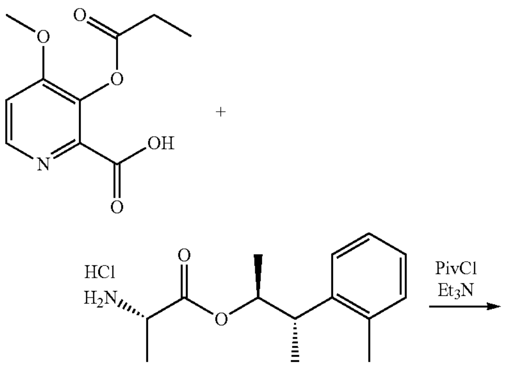

-continued

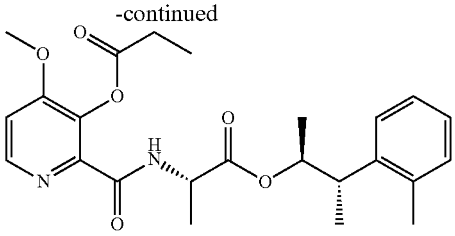

A 250 mL round bottom flask equipped with an overhead stirrer, nitrogen inlet, and temperature probe was charged with 4-methoxy-3-(propionyloxy)picolinic acid (18.1 g, 58.0 mmol, 50.3 wt % solid along with Et3N·HCl salt and NMI·HCl salt) and DCM (53 mL). The suspension was cooled to −10° C. and then triethylamine (5.6 mL, 4.1 g, 41 mmol) was added slowly. The reaction was stirred for 15 minutes, after which pivaloyl chloride (2.4 mL, 2.3 g, 19.3 mmol) was added slowly, maintaining the reaction temperature below 0° C. The reaction was stirred at −10° C. for 10 minutes. A solution of (2S,3S)-3-(o-tolyl)butan-2-yl L-alaninate hydrochloride (5.53 g, 18.4 mmol, 90.5 wt % with 9 wt % heptane and 0.5 wt % CPME) in DCM (20 mL) was added. The reaction was stirred at 0° C. for 1 h and was then quenched with saturated aqueous NaHCO3 (75 mL). The biphasic mixture was stirred for 15 minutes and then the layers were separated. The organic layer was returned to the reaction vessel and 1 M HCl (75 mL) was added. The mixture was stirred for 15 minutes and then the layers were separated. The organic layer was concentrated under reduced pressure to give an orange oil. The crude material was dissolved in isopropanol (30 mL) and then concentrated under reduced pressure to remove residual DCM and water. The crude oil was suspended in isopropanol (20 mL) and heated to 50° C. until a homogenous solution formed. The mixture was stirred at room temperature for 3 h and then cooled to 0° C. for 1 h. The crystallized product was isolated via vacuum filtration and washed with heptane (3×10 mL) to give 4.73 g (58%) of the title compound as an off-white solid.

1H NMR (500 MHz, CDCl3) δ 8.54 (s, 1H), 8.34 (d, J=5.4 Hz, 1H), 7.20-7.07 (m, 4H), 7.00 (d, J=5.5 Hz, 1H), 5.13 (dq, J=8.3, 6.2 Hz, 1H), 4.73 (pd, J=7.2, 0.4 Hz, 1H), 3.90 (s, 3H), 3.26-3.11 (m, 1H), 2.74 (q, J=7.6 Hz, 2H), 2.35 (s, 3H), 1.51 (d, J=7.2 Hz, 3H), 1.28 (t, J=7.5 Hz, 3H), 1.25 (d, J=6.9 Hz, 3H), 1.12 (d, J=6.2 Hz, 3H). 13C NMR (151 MHz, CDCl3) δ 172.4, 172.3, 162.4, 159.5, 146.6, 141.8, 141.7, 137.6, 135.5, 130.5, 126.4, 126.3, 126.2, 109.7, 76.3, 56.3, 48.2, 39.8, 27.3, 20.0, 18.8, 18.5, 17.5, 8.8. HRMS-ESI (m/z) [M+H]+ calcd for C24H30N2O6, 443.2177. found, 443.2189.

Example A1.3 (2S,3S)-3-(o-tolyl)butan-2-yl (3-isobutyryloxy-4-methoxypicolinoyl)-L-alaninate

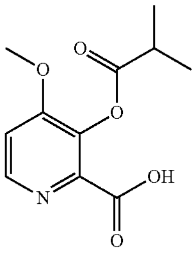

+

-continued

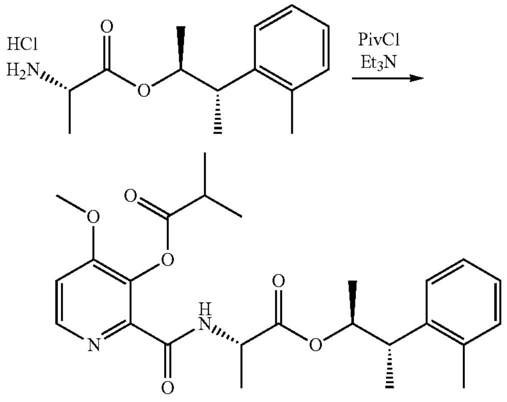

A 500 mL round bottom flask equipped with an overhead stirrer, nitrogen inlet, and temperature probe was charged with 4-methoxy-3-(isobutyryloxy)picolinic acid (10 g, 20.1 mmol, 48 wt % solid along with Et3N·HCl salt and NMI·HCl salt) and DCM (63 mL). The suspension was cooled to 0° C. and then triethylamine (8 mL, 5.8 g, 57 mmol) was added slowly. The reaction was stirred for 15 minutes, after which pivaloyl chloride (3.2 g, 26.8 mmol) was added slowly, maintaining the reaction temperature below 10° C. The reaction was stirred at 5° C. for 15 minutes. A solution of (2S,3S)-3-(o-tolyl)butan-2-yl L-alaninate hydrochloride (5.19 g, 19.1 mmol) was added. The reaction was stirred at 0° C. for 1 h and was then quenched with saturated aqueous NaHCO3 (100 mL) and water (50 mL). The biphasic mixture was stirred for 15 minutes and then the layers were separated. The organic layer was returned to the reaction vessel and 1 M HCl (100 mL) was added. The mixture was stirred for 15 minutes and then the layers were separated. The organic layer was concentrated under reduced pressure to give an oil. The crude material was purified via silica gel chromatography by eluting with an ethyl acetate/hexane gradient to afford to give 3.8 g (44%) of the title compound as a colorless oil. Analytical data matched that of Example A2.

Example A2. (2S,3S)-3-(o-tolyl)butan-2-yl (3-isobutyryloxy-4-methoxypicolinoyl)-L-alaninate

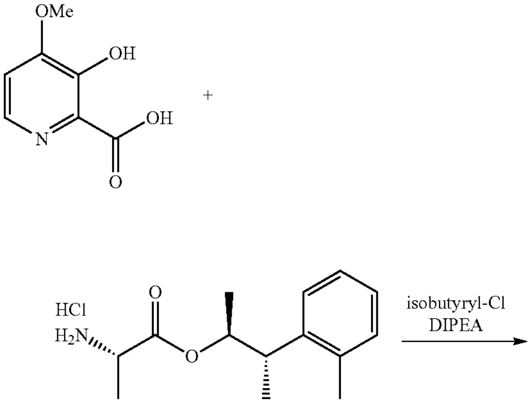

-continued

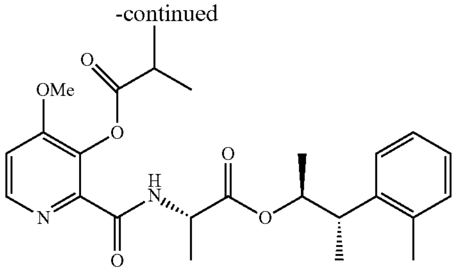

A 1 L four-neck flask equipped with a temperature probe, nitrogen inlet, and mechanical stirrer was charged with 3-hydroxy-4-methoxypicolinic acid (17.75 g, 105 mmol) and DCM (265 mL). The suspension was cooled to 0° C. and DIPEA (75 mL, 429 mmol) was slowly added. This reaction mixture was stirred until the suspension became primarily a homogeneous solution. The reaction was cooled to −20° C. and isobutyryl chloride (18.6 mL, 200 mmol) was then added slowly via syringe. This mixture was allowed to stir for 30 minutes. The reaction was cooled to −40° C. and a solution of (2S,3S)-3-(o-tolyl)butan-2-yl L-alaninate hydrochloride (22.45 g, 95 mmol) in DCM (200 mL) was added dropwise. The reaction was stirred for 1 h then the reaction was gradually warmed to RT.

The crude reaction mixture was quenched with saturated aqueous sodium bicarbonate and stirred for 10 minutes. The layers were separated and the organic layer was washed with a 1:1 mixture of brine: 1 N HCl. The layers were separated and the organic layer was dried over anhydrous sodium sulfate, filtered and concentrated to a dark brown oil. The crude material was purified via silica gel chromatography (gradient ethyl acetate in hexanes) to afford the title compound (35.5 g, 77% yield) as a yellow oil.

1H NMR (500 MHz, Chloroform-d) δ 8.63-8.40 (m, 1H), 8.33 (d, J=5.4 Hz, 1H), 7.22-7.05 (m, 4H), 6.99 (d, J=5.5 Hz, 1H), 5.13 (dq, J=8.4, 6.2 Hz, 1H), 4.79-4.67 (m, 1H), 3.88 (s, 3H), 3.24-3.13 (m, 1H), 2.95 (hept, J=7.0 Hz, 1H), 2.34 (s, 3H), 1.50 (d, J=7.2 Hz, 3H), 1.36 (d, J=7.0 Hz, 3H), 1.36 (d, J=7.0 Hz, 3H), 1.25 (d, J=6.9 Hz, 3H), 1.12 (d, J=6.3 Hz, 3H); 13C NMR (126 MHz, Chloroform-d) δ 174.7, 172.4, 162.3, 159.4, 146.6, 141.8, 141.8, 137.6, 135.5, 130.5, 126.3, 126.2, 109.6, 76.2, 56.3, 48.1, 39.7, 33.9, 20.0, 18.8, 18.7, 18.5, 17.4 [one signal missing due to incidental equivalence]; HRMS-ESI (m/z) [M+H]+ calcd for C25H32N2O6, 457.2333. found, 457.2322.

Example A3 Step 1 (2S,3S)-3-(o-tolyl)butan-2-yl (3-((ethoxycarbonyl)oxy)-4-methoxypicolinoyl)-L-alaninate

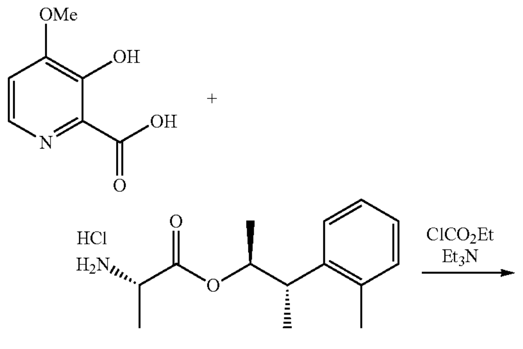

-continued

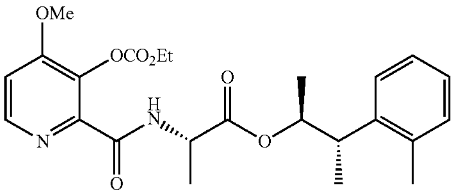

A 3-neck 100 mL flask equipped with a stir bar, temperature probe and nitrogen inlet was charged with 3-hydroxy-4-methoxypicolinic acid (1.63 g, 9.66 mmol) and DCM (46.0 mL). The suspension was cooled to 0° C. and triethylamine (5.8 mL, 41.4 mmol) was added dropwise via syringe resulting in a homogeneous solution after stirring for 10 min. The solution was cooled to −15° C. and ethyl chloroformate (1.8 mL, 18.9 mmol) was added dropwise via syringe. After stirring for 15 min, (25,35)-3-(o-tolyl)butan-2-yl L-alaninate hydrochloride (2.5 g, 9.20 mmol) was added to the flask in one portion.

After 30 min, the reaction was quenched with 50 mL of water and 10 mL of 2N HCl. The biphasic mixture was diluted with DCM and transferred to a separatory funnel. The layers were separated and the organic layer was dried with Na2SO4, filtered and concentrated to afford a pale yellow oil. The crude material was purified via silica gel chromatography by eluting with an ethyl acetate/hexane gradient to afford the title compound as an off-white solid (2.7 g, 61%):

1H NMR (400 MHz, Chloroform-d) δ 8.52 (d, J=8.1 Hz, 1H), 8.35 (d, J=5.4 Hz, 1H), 7.21-7.06 (m, 4H), 7.02 (d, J=5.5 Hz, 1H), 5.14 (dq, J=8.4, 6.2 Hz, 1H), 4.77 (p, J=7.3 Hz, 1H), 4.36 (q, J=7.1 Hz, 2H), 3.92 (s, 3H), 3.27-3.12 (m, 1H), 2.35 (s, 3H), 1.51 (d, J=7.1 Hz, 3H), 1.41 (t, J=7.1 Hz, 3H), 1.26 (d, J=6.9 Hz, 3H), 1.12 (d, J=6.2 Hz, 3H); 13C NMR (101 MHz, CDCl3) δ 172.4, 162.3, 159.4, 152.5, 146.9, 141.9, 141.8, 137.8, 135.5, 130.5, 126.4, 126.3, 126.3, 110.0, 76.3, 65.4, 56.4, 48.1, 39.8, 20.0, 18.8, 18.5, 17.4, 14.2; ESIMS m/z 459.2 ([M+H]+).

Example A3 Step 2. (2S,3S)-3-(o-tolyl)butan-2-yl (3-hydroxy-4-methoxypicolinoyl)-L-alaninate and (2S,3S)-3-(o-tolyl)butan-2-yl (S)-2-(8-methoxy-2,4-dioxo-2H-pyrido[2,3-e][1,3]oxazin-3(4H)-yl)propanoate

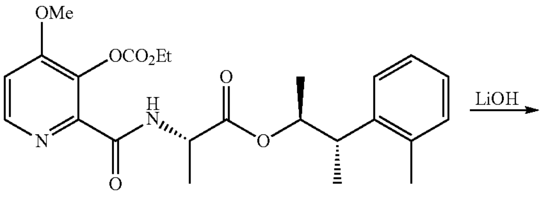

-continued

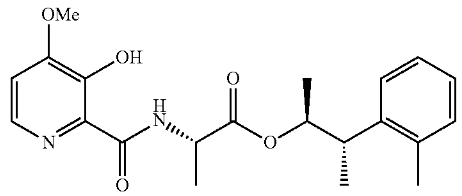

+

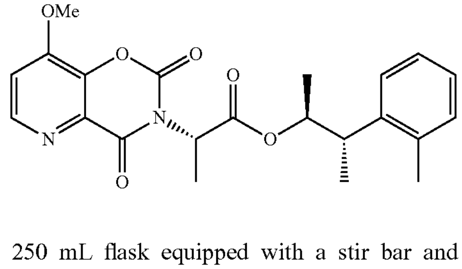

A 3-neck 250 mL flask equipped with a stir bar and nitrogen inlet was charged with (2S,3S)-3-(o-tolyl)butan-2-yl (3-((ethoxycarbonyl)oxy)-4-methoxypicolinoyl)-L-alaninate (1 g, 2.2 mmol) and THF (10.4 mL). Lithium hydroxide monohydrate (92 mg, 2.2 mmol) was placed in a separate vial, dissolved in water (5.2 mL) and added to the reaction flask. The reaction was allowed to stir for 3 h at RT. The reaction was acidified to pH=2 with 2N HCl and diluted with 50 mL of ethyl acetate. After stirring the mixture for 10 mins, it was transferred to the separation funnel and the layers were separated. The organic layer was dried with Na2SO4, filtered and concentrated to give a yellow oil. The crude material was purified via silica gel chromatography by eluting with an ethyl acetate/hexane gradient to afford the (2S,3S)-3-(o-tolyl)butan-2-yl (3-hydroxy-4-methoxypicolinoyl)-L-alaninate (300 mg, 34%) as a colorless oil and (2S,3S)-3-(o-tolyl)butan-2-yl (S)-2-(8-methoxy-2,4-dioxo-2H-pyrido[2,3-e][1,3]oxazin-3(4H)-yl)propanoate (100 mg, 11%) as a colorless oil.

(2S,3S)-3-(o-tolyl)butan-2-yl (3-hydroxy-4-methoxypicolinoyl)-L-alaninate: 1H NMR (400 MHz, Chloroform-d) δ 12.16 (s, 1H), 8.51 (d, J=7.9 Hz, 1H), 8.00 (d, J=5.2 Hz, 1H), 7.22-7.06 (m, 4H), 6.88 (d, J=5.2 Hz, 1H), 5.16 (dq, J=8.3, 6.3 Hz, 1H), 4.80-4.66 (m, 1H), 3.95 (s, 3H), 3.20 (dq, J=8.3, 6.9 Hz, 1H), 2.35 (s, 3H), 1.56 (d, J=7.2 Hz, 3H), 1.26 (d, J=6.9 Hz, 3H), 1.15 (d, J=6.3 Hz, 3H); 13C NMR (101 MHz, CDCl3) δ 171.9, 168.7, 155.4, 148.8, 141.7, 140.5, 135.5, 130.6, 126.4, 126.3, 126.3, 109.5, 76.6, 56.1, 48.2, 39.8, 20.0, 18.5, 18.4, 17.4 (one peak missing due to incidental equivalence); ESIMS m/z 387.2 ([M+H]+).

(2S,3S)-3-(o-tolyl)butan-2-yl (S)-2-(8-methoxy-2,4-dioxo-2H-pyrido[2,3-e][1,3]oxazin-3(4H)-yl)propanoate: 1H NMR (400 MHz, Chloroform-d) δ 8.60 (d, J=5.3 Hz, 1H), 7.18 (d, J=5.4 Hz, 1H), 7.16-7.12 (m, 2H), 7.07-6.99 (m, 2H), 5.60 (q, J=7.0 Hz, 1H), 5.18 (dq, J=8.2, 6.3 Hz, 1H), 4.06 (s, 3H), 3.13 (dt, J=8.4, 6.8 Hz, 1H), 2.29 (s, 3H), 1.71 (d, J=7.0 Hz, 3H), 1.22 (d, J=6.9 Hz, 3H), 1.07 (d, J=6.3 Hz, 3H); 13C NMR (101 MHz, CDCl3) δ 168.3, 158.7, 154.2, 149.1, 145.80, 141.7, 141.5, 135.5, 131.5, 130.3, 126.4, 126.2, 126.1, 111.5, 76.9, 56.8, 51.5, 39.6, 20.0, 17.8, 17.7, 14.0; ESIMS m/z 413.2 ([M+H]+).

Example A3 Step 2.1 (2S,3S)-3-(o-tolyl)butan-2-yl (3-acetoxy-4-methoxypicolinoyl)-L-alaninate

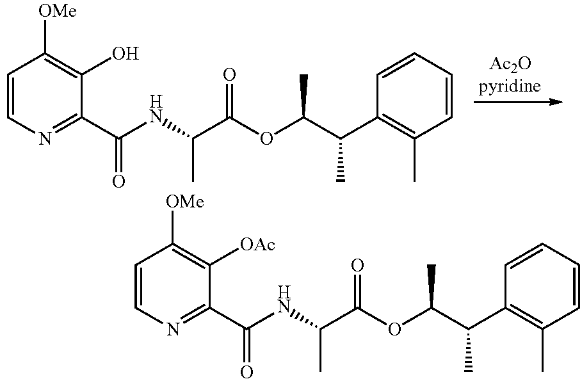

A 50 mL flask equipped with a stir bar was charged with (25,35)-3-(o-tolyl)butan-2-yl (3-hydroxy-4-methoxypicolinoyl)-L-alaninate (250 mg, 0.647 mmol), pyridine (1.3 mL) and acetic anhydride (0.18 mL, 1.94 mol). The reaction was stirred for 1 h at RT, heptane (20 mL) was added and the mixture was concentrated. The resulting oil was dissolved in MTBE (20 mL) and then concentrated to afford the title compound as a white solid (100 mg, 36% yield). No further purification was necessary. Analytical data matched that from Example A1.1.

Example A3 Step 2.2 (2S,3S)-3-(o-tolyl)butan-2-yl (4-methoxy-3-(propionyloxy)picolinoyl)-L-alaninate

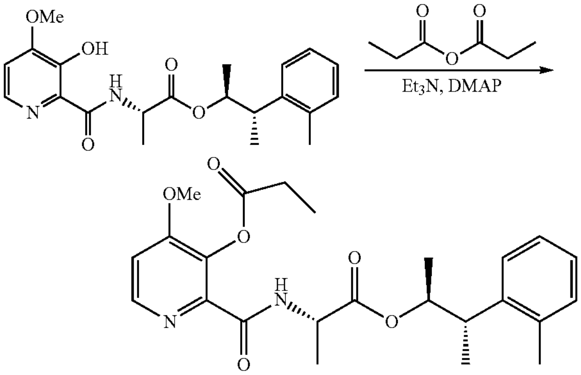

A 3 L reactor equipped with an overhead stirrer, nitrogen inlet, temperature probe, and a reflux condenser was charged with (25,35)-3-(o-tolyl)butan-2-yl (3-hydroxy-4-methoxypicolinoyl)-L-alaninate (200 g, 518 mmol) and DCM (1 L). The mixture was stirred and cooled to 0° C. and triethylamine (76 mL, 543 mmol) was added. The reaction was stirred for 1 h and then N,N-dimethylpyridin-4-amine (3.2 g, 25.9 mmol) was added. Propionic anhydride (79 mL, 621 mmol) was added slowly over 0.5 h and the reaction was monitored by HPLC for consumption of starting material. After 1.5 h, the reaction was quenched with saturated aqueous sodium bicarbonate (1 L) and the biphasic mixture was stirred for 15 minutes. The layers were separated and the organic layer was returned to the reaction vessel and 1N HCl (1 L) was added and the mixture was stirred for 15 minutes. The layers were separated and the organic layer was concentrated under reduced pressure. The crude material was taken up in isopropanol (~250 mL) and concentrated under reduced pressure to give an off-white solid. The crude solid was suspended in i-PrOH (700 mL) and warmed to 55° C. until the mixture was homogenous. The solution was allowed to slowly cool to room temperature overnight. The solid was collected via vacuum filtration and the flask was rinsed with cold isopropanol. The filter cake was then washed with heptane (500 mL) and allowed to dry for 3 h. The dried filter cake was collected to give 202 g of (25,35)-3-(o-tolyl)butan-2-yl (4-methoxy-3-(propionyloxy)picolinoyl)-L-alaninate (88%) as a white solid. Analytical data matched that from Example A1.2.

Example A3 Step 2.3 (2S,3S)-3-(o-tolyl)butan-2-yl (3-isobutyryloxy-4-methoxypicolinoyl)-L-alaninate

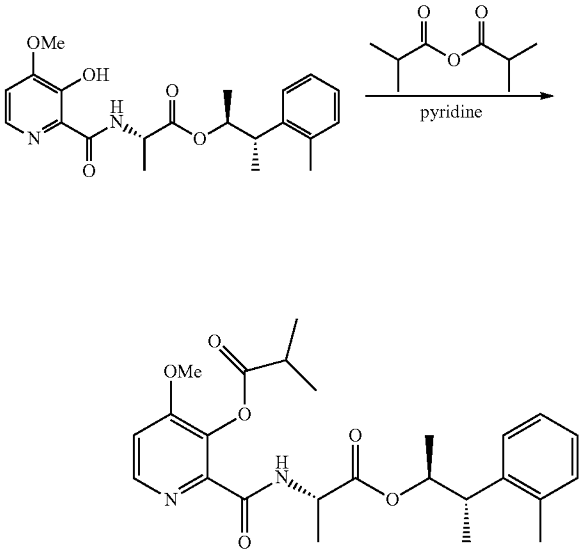

A 50 mL flask equipped with a stir bar was charged with (25,35)-3-(o-tolyl)butan-2-yl (3-hydroxy-4-methoxypicolinoyl)-L-alaninate (250 mg, 0.647 mmol), pyridine (1.3 mL) and isobutyric anhydride (0.16 mL, 0.970 mmol). The reaction was stirred for 1 h at RT. Additional isobutyric anhydride (0.16 mL, 0.970 mmol) was added to the mixture and the reaction was stirred overnight. The reaction material was directly loaded on a silica gel cartridge and purified via silica gel chromatography by eluting with an ethyl acetate/hexane gradient. The resulting oil was dissolved in ethyl acetate, transferred to a separatory funnel and washed with aqueous ammonium chloride (3x20 mL). The layers were separated and the organic layer was dried with anhydrous sodium sulfate, decanted and concentrated. MTBE was added and the resulting suspension was filtered to remove residual ammonium chloride. The filtrate was concentrated to afford the title compound (218 mg, 0.430 mmol, 66% yield) as a colorless oil. Analytical data matched that from Example A2.

Example B1.1 3-(Acetyloxy)-4-methoxypicolinic acid

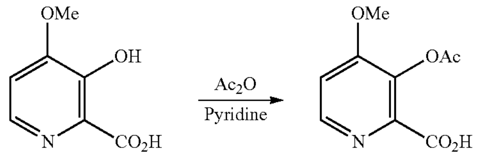 [SMILES: "Ac2O" ; COc1ccnc(C(=O)O)c1O ; COc1ccnc(C(=O)O)c1OC(C)=O]

3-Hydroxy-4-methoxypicolinic acid (5.0 g, 29.6 mmol) was slurried in 50 mL of pyridine and 50 mL of acetic anhydride at ambient temperature. After 1 h, a yellow solution had formed which was then stirred overnight. The solution was evaporated at 45° C. (2 mm Hg) to give 6.28 g of tan solid (99% yield, mp=132-134° C.). 1H NMR (400 MHz, DMSO-d6) δ 13.32 (s, 1H), 8.43 (d, J=5.5 Hz, 1H), 7.40 (d, J=5.5 Hz, 1H), 3.91 (s, 3H), 2.27 (s, 3H). 13C NMR (101 MHz, DMSO-d6) δ 167.95, 164.81, 158.34, 147.87, 142.77, 136.18, 110.87, 56.59, 20.27. HRMS (m/z) calcd for C9H9NO5 211.0478, found 211.0481 ([M]+).

Example B1.2 4-methoxy-3-(propionyloxy)picolinic acid

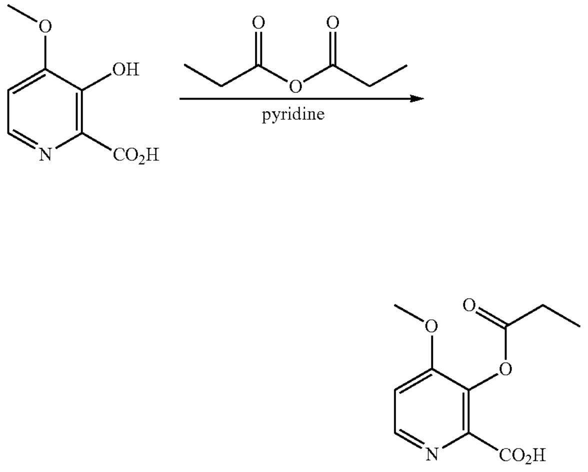

3-hydroxy-4-methoxypicolinic acid (25 g, 148 mmol) was slurried in 100 mL of pyridine and 57.1 mL of propionic anhydride at ambient temperature. The reaction was stirred for 3.5 days. The reaction mixture was then added to 650 mL heptane over ~30 min. The reaction mixture was cooled to 0° C. for ~30 minutes and then the solids were collected via vacuum filtration. The filter cake was washed with heptane (50 mL), ethyl acetate (75 mL) and heptane (50 mL) to give 4-methoxy-3-(propionyloxy)picolinic acid (27.92 g, 124 mmol, 84% yield).

1H NMR (500 MHz, (CD3)SO) δ 8.46 (d, J=5.6 Hz, 1H), 7.45 (d, J=5.7 Hz, 1H), 3.93 (s, 3H), 2.60 (q, J=7.5 Hz, 2H), 1.14 (t, J=7.5 Hz, 3H). 13C NMR (126 MHz, DMSO) δ 171.6, 163.2, 161.6, 152.5 146.5, 140.4, 112.0, 58.1, 27.1, 8.8. MS-ESI (m/z) [M+H]+ calcd for C10H11NO5 226.1. found, 226.0.

Example B1.3 4-methoxy-3-(propionyloxy)picolinic acid

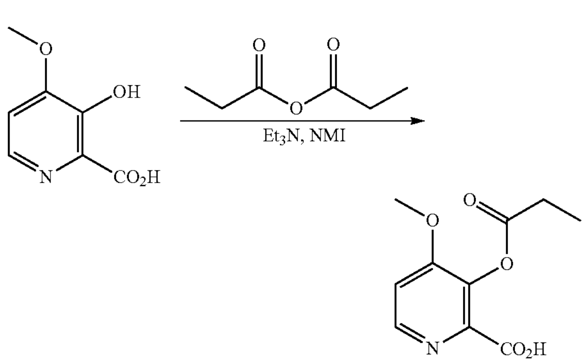

A 500 mL flask equipped with a stirbar, a nitrogen inlet, and a temperature probe was charged with 3-hydroxy-4-methoxypicolinic acid (25 g, 148 mmol), propionic anhydride (47 mL, 48.1 g, 370 mmol), and DCM (25 mL). Triethylamine (23 mL, 16.5 g, 65 mmol) and 1-methylimidazole (1.2 mL, 1.21 g, 5.9 mmol) were then added. The heterogeneous reaction mixture became a homogeneous solution after ca. 3 h and was stirred overnight at RT. After consumption of the starting material was observed by 1H NMR analysis, the reaction mixture was slowly added to a solution of HCl in CPME (75 mL, 3 M HCl in CPME, 222 mmol) and heptane (250 mL) at 0° C. The heterogeneous mixture was stirred for 0.5 h and then the solids were collected via vacuum filtration. The filter cake was washed with heptane and then dried to give the title compound (62.5 g total solids as heptane wetcake, 50 wt % active, 95% yield) along with the hydrochloride salts of triethylamine and NMI as a tan solid. Analytical data matched that of example B1.2.

Example B1.4 4-methoxy-3-(isobutyryloxy)picolinic acid

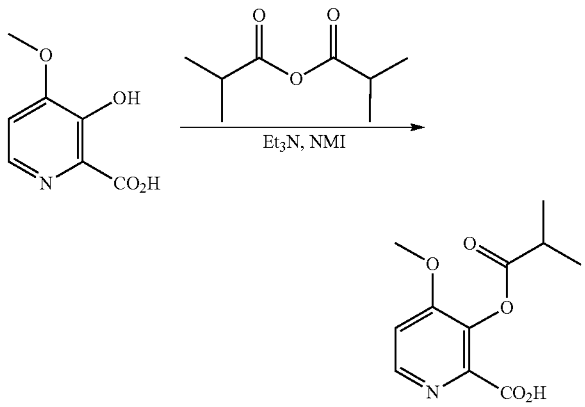

A 250 mL flask equipped with a stirbar, a nitrogen inlet, and a temperature probe was charged with 3-hydroxy-4-methoxypicolinic acid (5 g, 30 mmol), isobutyric anhydride (14 g, 88 mmol), and DCM (5 mL). Triethylamine (4.6 mL, 3.3 g, 33 mmol) and 1-methylimidazole (0.24 g, 3 mmol) were then added. The heterogeneous reaction mixture became a homogeneous solution after ca. 4 h and was stirred overnight at RT. After consumption of the starting material was observed by 1H NMR analysis, the reaction mixture was slowly added to a solution of HCl in CPME (15 mL, 3 M HCl in CPME, 44 mmol) and heptane (50 mL) at RT. The heterogeneous mixture was stirred for 0.5 h and then the solids were collected via vacuum filtration. The filter cake was washed successively with heptane (50 mL), ethyl acetate (50 mL), and heptane (50 mL) The wetcake was dried to give the title compound (10.5 g total, 48 wt % of the title compound, 71% yield) along with the hydrochloride salts of triethylamine and NMI as a tan solid.

1H NMR (500 MHz, (CD3)SO) 6 8.56 (d, J=5.9 Hz, 1H), 7.58 (d, J=5.9 Hz, 1H), 3.99 (s, 3H), 2.85 (h, J=7.0 Hz, 1H), 1.24 (d, J=7.0 Hz, 6H); 13C NMR (126 MHz, DMSO) δ 173.9, 163.7, 160.9, 152.6 147.0, 141.2, 111.8, 58.1, 33.6, 19.0. MS-ESI (m/z) [M+H]+ calcd for C11H13NO5 239.1. found, 240.2; IR (thin film): 3411, 2978, 2944, 2601, 2496, 1764, 1709, 1598, 1501, 1304, 1222, 1079, 1036, 831 cm-1.

Example C1.1 Step 1 (2S,3S)-3-(o-tolyl)butan-2-yl (tert-butoxycarbonyl)-L-alaninate

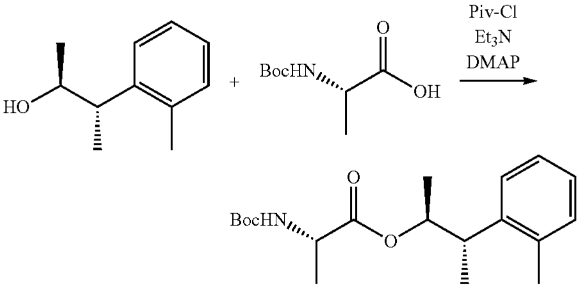

A 100 mL three-neck flask equipped with a stirbar, temperature probe, and nitrogen inlet was charged with (tert-butoxycarbonyl)-L-alanine (1.61 g, 8.5 mmol), and THF (10 mL). The solution was cooled to 0° C. and triethylamine (2.20 mL, 15.8 mmol) was added. The reaction was stirred for 15 minutes and pivaloyl chloride (1.05 mL, 8.52 mmol) was added. After stirring for about 15 min, (25,35)-3-(o-tolyl)butan-2-ol (1 g, 6.1 mmol) in THF (5 mL) was added followed by DMAP (74 mg, 0.609 mmol). The solution was stirred at 0° C. and gradually warmed to RT.

After stirring overnight, saturated aqueous ammonium chloride was added to the reaction followed by water. The organic layer was washed with saturated aqueous sodium bicarbonate (2×). The organic layer was dried with anhydrous sodium sulfate, decanted and concentrated to afford an oil. The crude material was taken up in heptane and washed with saturated aqueous sodium bicarbonate. The organic layer was concentrated to provide (2S,3S)-3-(o-tolyl)butan-2-yl (tert-butoxycarbonyl)-L-alaninate (1.9 g, 88% yield) as a colorless oil.

1H NMR (400 MHz, Chloroform-d) δ 7.21-7.06 (m, 4H), 5.19-5.01 (m, 2H), 4.42-4.23 (m, 1H), 3.17 (dq, J=8.6, 6.9 Hz, 1H), 2.35 (s, 3H), 1.45 (s, 9H), 1.40 (d, J=7.2 Hz, 3H), 1.24 (d, J=6.9 Hz, 3H), 1.10 (d, J=6.3 Hz, 3H); 13C NMR (126 MHz, Chloroform-d) δ 173.0, 155.0, 141.8, 135.5, 130.5, 126.3, 126.3, 126.3, 79.7, 76.2, 49.5, 39.8, 28.3, 20.0, 18.8, 18.5, 17.7; HRMS-ESI (m/z) [M+Na]+ calcd for C19H29NO4, 358.1989. found, 358.1990.

Example C1.1 Step 2 (2S,3S)-3-(o-tolyl)butan-2-yl L-alaninate hydrochloride

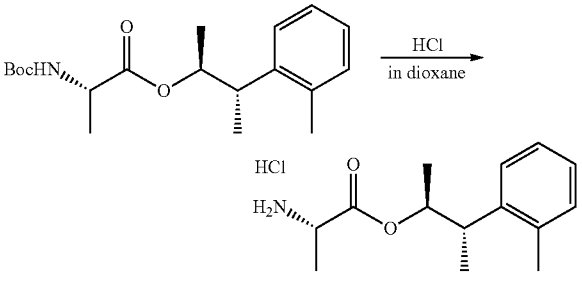

A 1 L flask equipped with a stirbar, condenser and nitrogen inlet was charged with (25,35)-3-(o-tolyl)butan-2-yl (tert-butoxycarbonyl)-L-alaninate (58.2 g, 174 mmol) and dioxane (50 mL). HCl (4 M in dioxane) (195 mL, 781 mmol) was slowly added to the reaction. After 2 h of stirring, the volatiles were removed on the rotovap. Acetonitrile was added and the mixture was concentrated resulting in a white solid. The solid was dried under vacuum overnight to afford (2S,3S)-3-(o-tolyl)butan-2-yl L-alaninate hydrochloride (46 g, mmol, 96% yield) as a white solid: mp=165-169° C.

1H NMR (500 MHz, DMSO-d6) δ 8.74 (s, 3H), 7.25-7.21 (m, 1H), 7.21-7.14 (m, 2H), 7.14-7.09 (m, 1H), 5.07 (dq, J=7.9, 6.3 Hz, 1H), 4.05 (q, J=7.2 Hz, 1H), 3.20 (p, J=7.0 Hz, 1H), 2.32 (s, 3H), 1.46 (d, J=7.2 Hz, 3H), 1.22 (d, J=6.9 Hz, 3H), 1.09 (d, J=6.3 Hz, 3H); 13C NMR (126 MHz, DMSO-d6) δ 169.5, 141.3, 135.1, 130.2, 126.2, 126.1, 126.1, 76.0, 47.9, 38.8, 19.4, 18.0, 16.9, 15.6; HRMS-ESI (m/z) [M+H]+ calcd for C14H21NO2, 236.1651. found, 236.1641.

Example C1.2 Step 1. (2S,3S)-3-(o-tolyl)butan-2-yl (tert-butoxycarbonyl)-L-alaninate

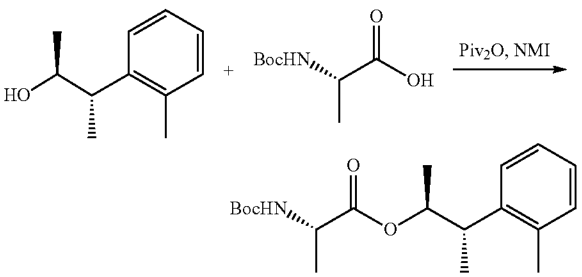

A 100 mL 3-neck round bottom flask equipped with a temperature probe, reflux condenser, and nitrogen inlet was charged with (tert-butoxycarbonyl)-L-alanine (4.15 g, 21.92 mmol), (25,35)-3-(o-tolyl)butan-2-ol (3.0 g, 18.27 mmol), and heptane (30 mL). Pivalic anhydride (5.23 mL, 25.6 mmol) was added and the mixture was heated to 50° C. 1-methyl-1H-imidazole (NMI, 0.12 mL, 1.46 mmol) was added. The reaction was stirred at 50° C. overnight with monitoring by HPLC analysis for consumption of alcohol. After stirring overnight, the reaction was allowed to cool to room temperature. Potassium carbonate (20 wt %, 50 mL, 72.4 mmol) was added, and the biphasic mixture was stirred for 10 minutes. The reaction was transferred to a separatory funnel. The layers were separated and the organic layer washed with water. The organic layer was dried over sodium sulfate, filtered and concentrated. The crude material was purified via silica gel chromatography (gradient ethyl acetate in hexanes) to afford (2S,3S)-3-(o-tolyl)butan-2-yl (tert-butoxycarbonyl)-L-alaninate (5.89 g, 17.6 mmol, 96% yield) as a colorless oil. Analytical data matched that from Example C1.1.

Example C1.2 Step 2 (2S,3S)-3-(o-tolyl)butan-2-yl L-alaninate hydrochloride

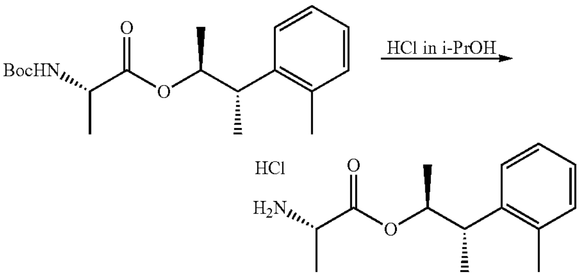

To a 100 mL round bottom flask equipped with a stir bar and nitrogen inlet containing (2S,3S)-3-(o-tolyl)butan-2-yl (tert-butoxycarbonyl)-L-alaninate (5.89 g, 17.6 mmol) and heptane (20 mL) was added 6 M HCl in i-PrOH (10 mL, 60.0 mmol) slowly. The reaction was stirred at room temperature overnight. The resulting solid was collected via vacuum filtration and washed with heptane. The solid was dried to afford (2S,3S)-3-(o-tolyl)butan-2-yl L-alaninate hydrochloride (3.63 g, 13.4 mmol, 76%) as a white solid. Analytical data matched that from Example C1.1.

Example C2.1 (2S,3S)-3-(o-tolyl)butan-2-yl L-alaninate hydrochloride

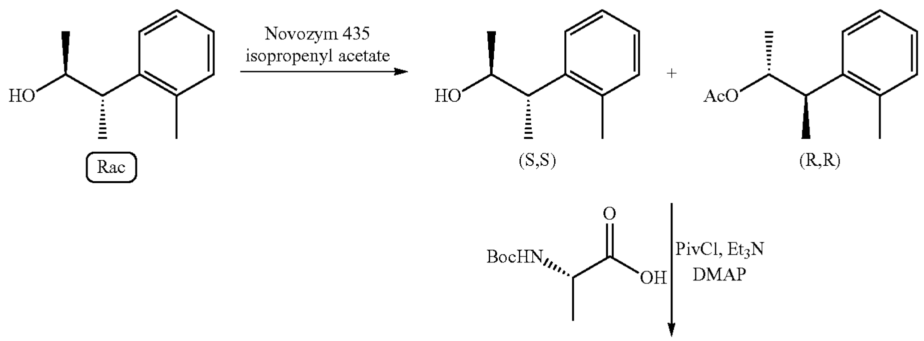

-continued

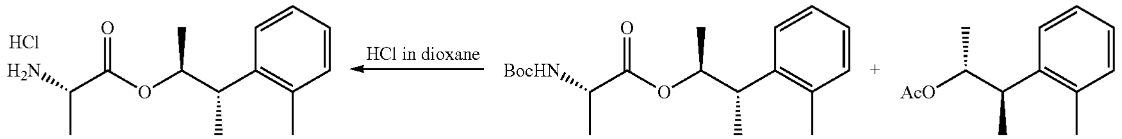

A 1 L jacketed reactor equipped with overhead stirring and temperature probe was charged with a racemic (Rac) mixture of (2S,3S)- and (2R,3R)-3-(o-tolyl)butan-2-ol (48 g, 292 mmol, 1:1 mixture of enantiomers), Me-THF (96 mL) and isopropenyl acetate (31.7 mL, 292 mmol). Novozym® 435 (immobilized CAL-B lipase) (4.8 g, 10 wt %) was added and the reaction was stirred at 45° C. for 28 h. The reaction mixture was cooled to RT and filtered to remove the immobilized enzyme. The immobilized enzyme was washed with Me-THF (about 100 mL) and the combined filtrate was concentrated to afford 89.2 g of a mixture of (2S,3S)-3-(o-tolyl)butan-2-ol and (2R,3R)-3-(o-tolyl)butan-2-yl acetate in Me-THF.

A 1 L jacketed reactor equipped with overhead stirring, temperature probe and nitrogen inlet was charged with (tert-butoxycarbonyl)-L-alanine (38.9 g, 204 mmol) and Me-THF (243 mL). The colorless solution was cooled to 0° C. and triethylamine (52.8 mL, 380 mmol) was added dropwise via syringe. The mixture was stirred for 30 min and then pivaloyl chloride (25.2 mL, 204 mmol) was added via syringe resulting in a very thick white suspension. More MeTHF (57 mL) was added to aid in stirring. After stirring for 1 h, an 86.4 g solution of (2S,3S)-3-(o-tolyl)butan-2-ol and (2R,3R)-3-(o-tolyl)butan-2-yl acetate in Me-THF was added followed by DMAP (1.78 g, 14.6 mmol). After stirring overnight at 0° C., water (200 mL) was slowly added to the reaction. After stirring for 60 min, the layers were separated. The organic layer was washed with aqueous ammonium chloride solution (about 200 mL) and then sodium carbonate (10%, 3×200 mL). The organic layer was then dried over anhydrous sodium sulfate, filtered and concentrated to afford a mixture of (2S,3S)-3-(o-tolyl)butan-2-yl (tert-butoxycarbonyl)-L-alaninate and (2R,3R)-3-(o-tolyl)butan-2-yl acetate.

HCl in dioxane (4M, 166 mL, 657 mmol, 4.5 equiv) was then added slowly in portions to the mixture of (2S,3S)-3-(o-tolyl)butan-2-yl (tert-butoxycarbonyl)-L-alaninate and (2R,3R)-3-(o-tolyl)butan-2-yl acetate in a 1 L single-neck flask equipped with a stir bar, nitrogen inlet, and gas outlet. The reaction was stirred at RT for 3 h. The reaction mixture was concentrated to about 90 mL volume. MTBE (150 mL) was added, followed by 0.01% seed of crystalline (2S,3S)-3-(o-tolyl)butan-2-yl L-alaninate hydrochloride and the resulting suspension was stirred overnight. The white solid was collected by vacuum filtration and washed with MTBE (50 mL, about 1 volume) to give the title compound (28.5 g, 105 mmol, 37% yield from the starting mixture of (2S,3S)- and (2R,3R)-3-(o-tolyl)butan-2-ol) as a white solid.: mp=165-169° C.

1H NMR (500 MHz, DMSO-d6) δ 8.74 (s, 3H), 7.25-7.21 (m, 1H), 7.21-7.14 (m, 2H), 7.14-7.09 (m, 1H), 5.07 (dq, J=7.9, 6.3 Hz, 1H), 4.05 (q, J=7.2 Hz, 1H), 3.20 (p, J=7.0 Hz, 1H), 2.32 (s, 3H), 1.46 (d, J=7.2 Hz, 3H), 1.22 (d, J=6.9 Hz, 3H), 1.09 (d, J=6.3 Hz, 3H); 13C NMR (126 MHz, DMSO-d6) δ 169.5, 141.3, 135.1, 130.2, 126.2, 126.1, 126.1, 76.0, 47.9, 38.8, 19.4, 18.0, 16.9, 15.6; HRMS-ESI (m/z) [M+H]+ calcd for C14H21NO2, 236.1651. found, 236.1641.

Example C2.2. (2S,3S)-3-(o-tolyl)butan-2-yl L-alaninate hydrochloride

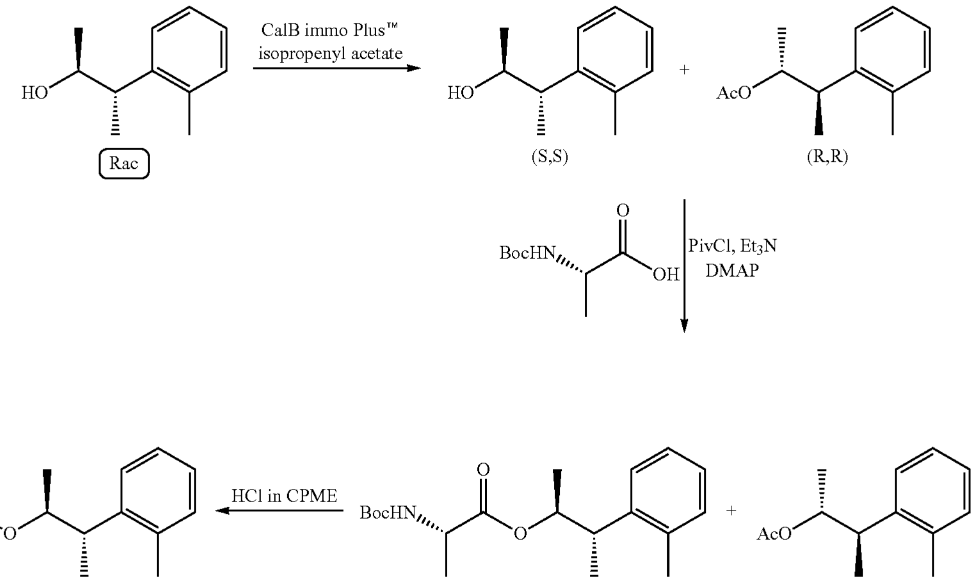

A 1 L jacketed reactor equipped with overhead stirring and temperature probe was charged with a racemic (Rac) mixture of (2S,3S)- and (2R,3R)-3-(o-tolyl)butan-2-ol (250 g, 1370 mmol, 1:1 mixture of enantiomers), CPME (500 mL) and isopropenyl acetate (134 mL, 1223 mmol). CAL B immo Plus™ (immobilized CAL-B lipase) (25 g, 10 wt %) was added and the reaction was stirred at 40° C. for 24 h.

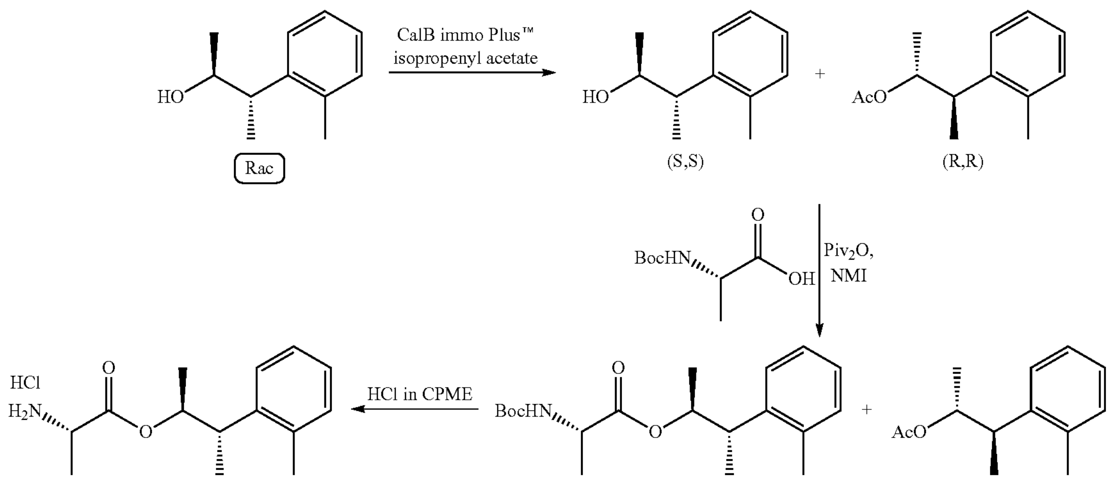

The reaction mixture was cooled to RT and filtered to remove the immobilized enzyme. The immobilized enzyme was washed with CPME (640 mL) and the filtrate was concentrated to afford 550 g of a mixture of (2S,3S)-3-(o-tolyl)butan-2-ol and (2R,3R)-3-(o-tolyl)butan-2-yl acetate in CPME.

A 5 L jacketed reactor equipped with overhead stirring, temperature probe and nitrogen inlet was charged with (tert-butoxycarbonyl)-L-alanine (183 g, 963 mmol) and CPME (1500 mL). The colorless solution was cooled to 0° C. and triethylamine (268 mL, 1926 mmol) was added dropwise via syringe. The mixture was stirred for 30 min and then pivaloyl chloride (119 mL, 963 mmol) was added via syringe resulting in a very thick white suspension. After stirring for 2 h, an 550 g solution of (2S,3S)-3-(o-tolyl) butan-2-ol and (2R,3R)-3-(o-tolyl)butan-2-yl acetate in CPME (assumed to be 685 mmol of (2S,3S)-3-(o-tolyl) butan-2-ol) was added followed by DMAP (8.41 g, 68.8 mmol). After stirring overnight at 0° C., water (1000 mL) was slowly added to the reaction. After stirring for 90 min, the layers were separated. The organic layer was washed with aqueous ammonium chloride solution and then sodium carbonate (10%, 500 mL). The organic layer was concentrated to afford 423 g of a mixture of (2S,3S)-3-(o-tolyl) butan-2-yl (tert-butoxycarbonyl)-L-alaninate and (2R,3R)-3-(o-tolyl)butan-2-yl acetate.

HCl in CPME (3M, 800 mL, 2410 mmol) was then added slowly to the mixture of (2S,3S)-3-(o-tolyl)butan-2-yl (tert-butoxycarbonyl)-L-alaninate and (2R,3R)-3-(o-tolyl)butan-2-yl acetate in a 5 L reactor equipped with a mechanical stirrer, gas outlet to base scrubber, nitrogen inlet, and temperature probe. The reaction was stirred at RT for 24 h. The reaction mixture was sparged with nitrogen gas and the resulting suspension was stirred overnight. The solid was collected by vacuum filtration and washed with CPME (1 L then 500 mL) to give the title compound (127 g, 34% yield from the starting mixture of (2S,3S)- and (2R,3R)-3-(o-tolyl)butan-2-ol) as a white solid after drying in a vacuum oven. Analytical data were identical to the compound isolated in Example C2.1.

Example C2.3. (2S,3S)-3-(o-tolyl)butan-2-yl L-alaninate hydrochloride

A 250 mL jacketed reactor equipped with overhead stirring and temperature probe was charged with CAL B immo Plus™ (immobilized CAL-B lipase) (5.25 g, 10.5 wt %) and CPME (69 g). The suspension was stirred and a 74.3 g solution of racemic (2S,3S)- and (2R,3R)-3-(o-tolyl)butan-2-ol (50 g, 304 mmol, 67.26 wt % solution, 1:1 mixture of enantiomers), in CPME was added followed by isopropenyl acetate (18.3 mL, 183 mmol). The reaction was heated to 40° C. and stirred for 18 h. The reaction mixture was cooled to RT and filtered to remove the immobilized enzyme. The immobilized enzyme was washed with CPME (100 mL). The filtrate (228 g) was analyzed concentrated to afford a mixture of (2S,3S)-3-(o-tolyl)butan-2-ol and (2R,3R)-3-(o-tolyl)butan-2-yl acetate in heptane. The filtrate was weighed (228 g) and assayed with an internal standard via GC analysis to afford a 9.99 wt % solution of (2S,3S)-3-(o-tolyl) butan-2-ol (46% in-pot yield).

A 50 mL three-neck flask equipped with a stirbar, temperature probe, reflux condenser and nitrogen inlet was charged with (tert-butoxycarbonyl)-L-alanine (2.08 g, 11 mmol). A 4.5 g solution of (2S,3S)-3-(o-tolyl)butan-2-ol and (2R,3R)-3-(o-tolyl)butan-2-yl acetate in CPME (calculated to be 10 mmol of (2S,3S)-3-(o-tolyl)butan-2-ol), and additional CPME (10 mL) was added. Pivalic anhydride (2.45 mL, 12 mmol) was added, the reaction was heated to 50° C. and 1-methyl-1H-imidazole (0.040 mL, 0.5 mmol) was added. The reaction was stirred at 50° C. for 25 h until the reaction was judged to be complete by HPLC analysis. A 10 wt % aqueous solution of potassium carbonate (30 mL) was added and the resulting biphasic mixture was stirred for 5 minutes. The biphasic mixture was transferred to a separatory funnel and the layers were separated. The organic layer was washed with water, dried over sodium sulfate, filtered, and concentrated in vacuo to give a mixture of (2S,3S)-3-(o-tolyl)butan-2-yl (tert-butoxycarbonyl)-L-alaninate and (2R,3R)-3-(o-tolyl)butan-2-yl acetate.

HCl in CPME (3M, 10 mL, 30 mmol) was then added slowly to the mixture of (2S,3S)-3-(o-tolyl)butan-2-yl (tert-butoxycarbonyl)-L-alaninate and (2R,3R)-3-(o-tolyl)butan-2-yl acetate in a 50 mL flask equipped with a stirbar and nitrogen inlet. The reaction was stirred at RT overnight. The solvent was removed, heptane was added and the resulting suspension was stirred. The solid was collected by vacuum filtration and washed with heptane and then a 1:1 mixture of heptane:MTBE to give the title compound (2.30 g, 67% yield from (2S,3S)-3-(o-tolyl)butan-2-ol) as a white solid after drying in a vacuum oven. Analytical data were identical to the compound isolated in Example C2.1.

Example C2.4. (2S,3S)-3-(o-tolyl)butan-2-yl L-alaninate hydrochloride

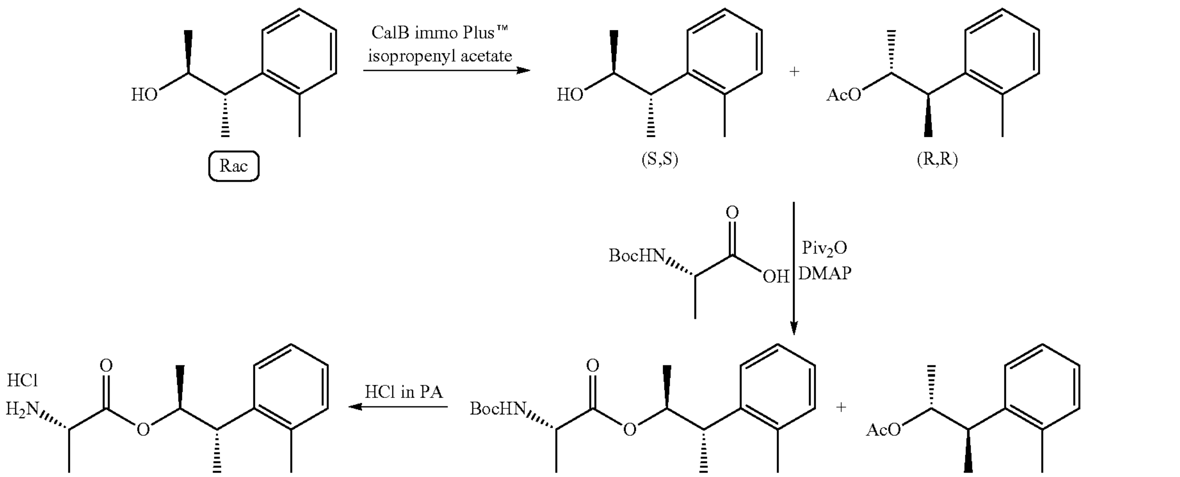

A 100 mL jacketed reactor equipped with overhead stirring and temperature probe was charged with a racemic (Rac) mixture of (2S,3S)- and (2R,3R)-3-(o-tolyl)butan-2-ol (12 g, 73.1 mmol, 1:1 mixture of enantiomers), heptane (24 mL) and isopropenyl acetate (6.98 mL, 64.3 mmol). The reaction was heated to 40° C. and CAL B immo Plus™ (immobilized CAL-B lipase) (1.2 g, 10 wt %) was added. The reaction mixture was stirred at 40° C. for 30 h, cooled to RT and filtered to remove the immobilized enzyme. The immobilized enzyme was washed with heptane and the filtrate was concentrated to afford a mixture of (2S,3S)-3-(o-tolyl)butan-2-ol and (2R,3R)-3-(o-tolyl)butan-2-yl acetate in heptane.

A 500 mL three-neck flask equipped with a stirbar, temperature probe, reflux condenser and nitrogen inlet was charged with a mixture of (2S,3S)-3-(o-tolyl)butan-2-ol and (2R,3R)-3-(o-tolyl)butan-2-yl acetate in heptane (assumed to be 36.5 mmol of (2S,3S)-3-(o-tolyl)butan-2-ol), (tert-butoxycarbonyl)-L-alanine (8.3 g, 43.8 mmol) and heptane (100 mL). DMAP (22 mg, 0.18 mmol) was added followed by pivalic anhydride (10.47 mL, 51.1 mmol) at ambient temperature to give a heterogeneous mixture. The temperature was increased to 50° C. Upon reaching 50° C., the reaction became homogeneous and was stirred at this temperature for 27 h. The reaction was cooled to RT then 0° C., at which time water (60 mL) was slowly added to the reaction. The biphasic mixture was allowed to warm to RT and stirred for 30 minutes. The biphasic mixture was transferred to a separatory funnel and the layers were separated. The organic layer washed with sat. sodium carbonate (2×60 mL) then brine (60 mL). The organic layer was dried over sodium sulfate, filtered, and concentrated in vacuo to give a mixture of (2S,3S)-3-(o-tolyl)butan-2-yl (tert-butoxycarbonyl)-L-alaninate and (2R,3R)-3-(o-tolyl)butan-2-yl acetate.

HCl in IPA (6M, 10 mL, 60 mmol) was then added slowly to the mixture of (2S,3S)-3-(o-tolyl)butan-2-yl (tert-butoxycarbonyl)-L-alaninate and (2R,3R)-3-(o-tolyl)butan-2-yl acetate in heptane (20 mL) in a 250 mL flask equipped with a stirbar and nitrogen inlet. The reaction was stirred at RT for 24 h. More heptane (20 mL) was added to the reaction mixture, followed by sparging with nitrogen gas. An additional 20 mL heptane was added to aid with stirring. The solid was collected by vacuum filtration and washed with heptane to give the title compound (5.85 g, 26% yield from the starting mixture of (2S,3S)- and (2R,3R)-3-(o-tolyl)butan-2-ol) as a white solid after drying in a vacuum oven. Analytical data were identical to the compound isolated in Example C2.1.

Example C2.5. (2S,3S)-3-(o-tolyl)butan-2-yl L-alaninate hydrochloride

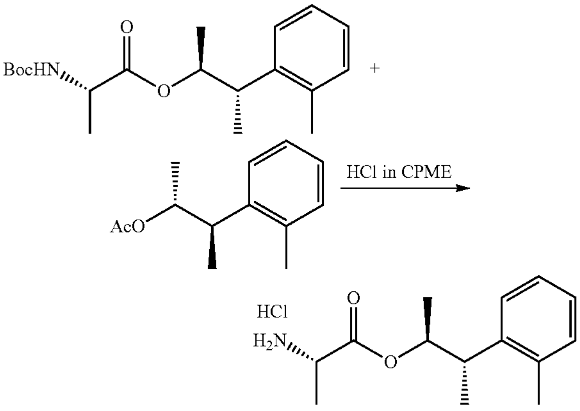

To a 250 mL jacket reactor equipped with mechanical agitator, thermoprobe, ¼" Teflon dip tube and reflux condenser was loaded (2S,3S)-3-(o-tolyl)butan-2-yl (tert-butoxycarbonyl)-L-alaninate crude product solution (57.1 g, 28.0 wt %, 47.7 mmol) containing (2R,3R)-3-(o-tolyl)butan-2-yl acetate (~50 mmol). HCl gas (6.2 g, 3.5 eq.) was slowly fed into the solution through ¼" Teflon dip tube subsurface over 2 h at 22° C. The solution was then stirred at 22° C. for 5 h. Heptanes (95 mL) was slowly added using a dropping funnel over 1 h at 19° C. The mixture was stirred for 2 h and the resultant was cooled down to 10° C. over 1 h. The slurry was drained and filtered through a filter crock under vacuum (~500 mmHg). The wet cake was washed with heptane (2×15 mL) and deliquored to afford crude product as off-white solid (9.67 g, 94.7 wt %, 70% yield). Analytical data matched that from Example C2.1.

Example D1.1 (2S,3S)- and (2R,3R)-3-(o-tolyl)butan-2-ol

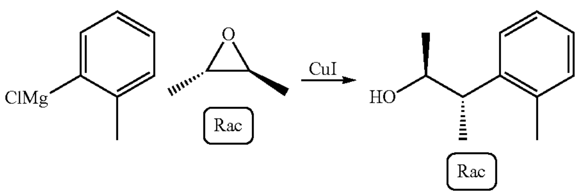

In a 3 L flask equipped with a mechanical stirrer, condenser, nitrogen inlet and temperature probe: copper(I) iodide (9.83 g, 51.1 mmol) was stirred in THF (304 mL). The mixture was cooled to −20° C. o-Tolylmagnesium chloride (613 mL, 613 mmol) was added over 30 minutes (T<−15° C.). After stirring for 10 minutes at −20° C., a solution of (2S,3S)- and (2R,3R)-2,3-dimethyloxirane (47.3 mL, 511 mmol, 1:1 mixture of enantiomers) in THF (304 mL) was added via cannula over 3 h. The mixture was stirred while the cold bath expired.

After stirring for 18 h (T=15° C.), saturated aqueous ammonium chloride was added to the suspension (361 mL, 2045 mmol). After stirring for 30 minutes, water (500 mL) and diethyl ether (1 L) was added. The organic layer was separated, washed with aqueous NH4OH (5%, 200 mL) and brine (400 mL). The organic layer was dried over Na2SO4, filtered and concentrated to provide a yellow oil (70.2 g, 95% purity, 79% yield). No further purification was necessary.

1H NMR (500 MHz, Chloroform-d) δ 7.19-7.12 (m, 3H), 7.12-7.05 (m, 1H), 3.88 (p, J=6.4 Hz, 1H), 2.99 (p, J=6.9 Hz, 1H), 2.33 (s, 3H), 1.47 (d, J=4.5 Hz, 1H), 1.29 (d, J=6.9 Hz, 3H), 1.10 (d, J=6.4 Hz, 3H); 13C NMR (126 MHz, CDCl3) δ 143.1, 135.6, 130.4, 126.3, 126.1, 125.9, 71.9, 41.8, 21.3, 20.0, 16.2; IR (thin film): 3355, 2966, 2930, 2872, 1490, 1455, 1079, 1004, 908, 757, 726 cm-1

Example D1.2 (2S,3S)- and (2R,3R)-3-(o-tolyl)butan-2-ol

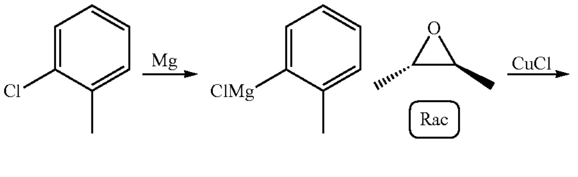

-continued

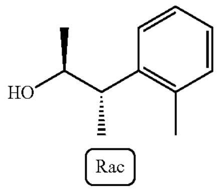

To a 1 L jacket reactor equipped with a thermal couple, condensor with nitrogen pad, Mg turnings (14.4 g, 1.33 eq.) was added, followed by HPLC grade THF (360 mL). The reaction mixture was heated to reflux (−65° C.). 2-chlorotoluene (70.2 g, 1.25 eq.) was added via syringe pump in 2 hr while refluxing. The reaction was heated for 16-18 hr till the 2-chlorotoluene conversion was greater than 99%. The reaction mixture was cooled to rt and agitation was stopped.

The freshly prepared Grignard reagent was cannulated into another 1 L jacket reactor, equipped with a thermal couple, condensor with nitrogen pad. The reagent was cooled to 0° C., then CuCl (2.2 g, 0.05 eq.) was added in one shot. The mixture was stirred for 1 hr at 10° C. before the addition of trans-2,3-epoxybutane (32 g, 1 eq.) via syringe pump in 3 hr. After the addition, the reaction was reacted at 10° C. for 2-16 hr before warming to rt, and the progress was monitored by GC method. After the completion the reaction was warmed to RT and 40% ammonium acetate (300 mL) was added to quench the reaction mixture. The mixture was stirred for 2 hr while oxygen was bubbled through the system. The aqueous phase was discarded and the organic phase was further washed with a 20% aqueous NaCl solution. The aqeuous NaCl solution was discarded. The remaining organic phase was weighed (351.4 g), assayed by GC method with internal standard, to afford a 19.67 wt % solution of the title compound (95% in-pot yield). The solution was used in the following step without further purification. Analytical data matched that from Example D1.1.

Example D1.3 (2S,3S)- and (2R,3R)-3-(o-tolyl)butan-2-ol

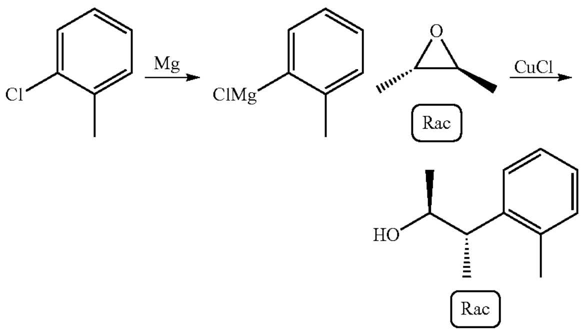

To a 250 mL jacket reactor equipped with a thermal couple, condensor with nitrogen pad, Mg turnings (7.2 g, 296 mmol) was added, followed by MeTHF (70 mL). The reaction mixture was heated to reflux and o-tolyl magnesium chloride in THF (1M, 15 mL) was added. The mixture was stirred at reflux for 30 minutes at which time a solution of 2-chlorotoluene (35.4 g, 280 mmol) in MeTHF (60 mL) was added via syringe pump in 2 hr. The reaction was heated overnight until the conversion was greater than 98% as judged by GC analysis. The reaction mixture was cooled to RT and agitation was stopped.

A portion of the Grignard reagent prepared in MeTHF (23.2 mmol, 1.2 equiv) was added to a reactor flask containing CuCl (0.19 g, 1.93 mmol, 0.1 eq.) and MeTHF (20 mL) at 0° C. over 2 hours. A solution of trans-2,3-epoxybutane (1.42 g, 19.3 mmol, 1 equiv) in MeTHF (4 mL) was added over 3 hr via syringe pump. After stirring overnight, the reaction was quenched with saturated aqueous ammonium chloride (20 mL) and water (20 mL). The layers were separated and the aqeuous phase was discarded. The remaining organic phase was collected (29.7 g), assayed by GC method with internal standard, to afford a 9.77 wt % solution of the title compound (91% in-pot yield). Analytical data matched that from Example D1.1.

Example D1.4 (2S,3S)- and (2R,3R)-3-(o-tolyl) butan-2-ol

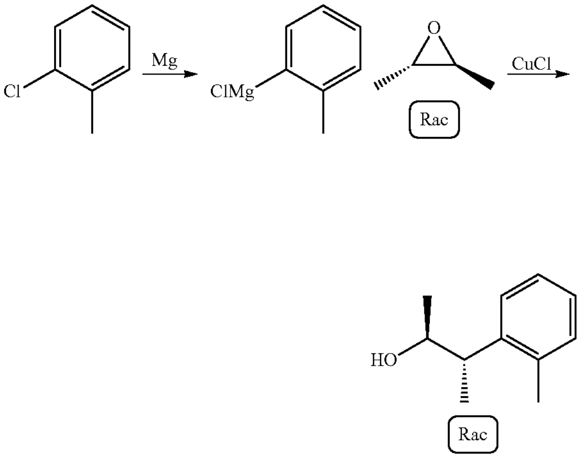

A flask equipped with a thermal couple, condensor with nitrogen pad was charged with o-tolyl magnesium chloride in MeTHF (2.5 M, 12 mL), Mg turnings (7.2 g, 296 mmol), and CPME (60 mL). The mixture was stirred at reflux for 10 minutes at which time a solution of 2-chlorotoluene (35.4 g, 280 mmol) in CPME (30 mL) was added via syringe pump in 2 hr. The reaction was heated for 2 days until the conversion was greater than 94% as judged by GC analysis. The reaction mixture was cooled to RT and agitation was stopped.

A portion of the Grignard reagent prepared in CPME (23 mmol, 1.2 equiv) was added to a reactor flask containing CuCl (0.19 g, 1.93 mmol, 0.1 eq.) and CPME (20 mL) at 0° C. A solution of trans-2,3-epoxybutane (1.42 g, 19.3 mmol, 1 equiv) in MeTHF (4 mL) was added over 3 hr via syringe pump. After stirring overnight, the reaction was quenched with saturated aqueous ammonium chloride (20 mL) and water (20 mL). The layers were separated and the aqeuous phase was discarded. The remaining organic phase was collected (30.7 g), assayed by GC method with internal standard, to afford a 9.35 wt % solution of the title compound (91% in-pot yield). Analytical data matched that from Example D1.1.

Example D2.1. (2S,3S)-3-(o-tolyl)butan-2-ol and (2R,3R)-3-(o-tolyl)butan-2-yl acetate

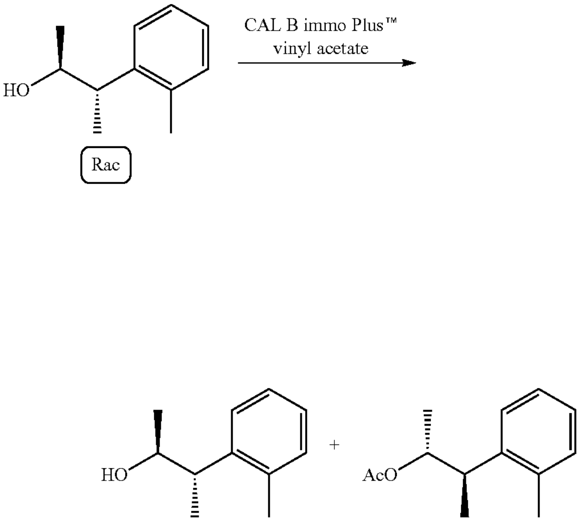

(S,S) (R,R)

A 100 mL flask equipped with a stirbar and temperature probe was charged with (2S,3S)- and (2R,3R)-3-(o-tolyl) butan-2-ol (10 g, 54.8 mmol, 1:1 mixture of enantiomers) and heptane (20 mL). Vinyl acetate (4.6 mL, 49.3 mmol) was added followed by CAL B immo Plus™ (immobilized CAL-B lipase) (1 g, 10 wt %) was added and the reaction was stirred at 45° C. overnight. The reaction mixture was cooled to RT and filtered to remove the immobilized enzyme. The immobilized enzyme was washed with heptane and the combined filtrate was concentrated. The crude material was purified via silica gel chromatography (gradient ethyl acetate in hexanes) to afford (2S,3S)-3-(o-tolyl) butan-2-ol (3.0 g, 17.4 mmol, 30% yield) as a pale yellow oil and (2R,3R)-3-(o-tolyl)butan-2-yl acetate (5.2 g, 24.0 mmol, 39% yield) as a pale yellow oil.

(2S,3S)-3-(o-tolyl)butan-2-ol: 1H NMR (400 MHz, Chloroform-d) δ 7.19-7.07 (m, 4H), 3.91 (p, J=6.4 Hz, 1H), 3.01 (p, J=6.9 Hz, 1H), 2.34 (s, 3H), 1.49 (s, 1H), 1.30 (d, J=7.0 Hz, 3H), 1.12 (d, J=6.3 Hz, 3H). 13C NMR (126 MHz, Chloroform-d) δ 143.1, 135.6, 130.4, 126.3, 126.1, 125.9, 71.9, 41.8, 21.3, 20.0, 16.2; IR (thin film): 3355, 2966, 2930, 2872, 1490, 1455, 1079, 1004, 908, 757, 726 cm-1. Chiral HPLC analysis was performed using a Chiralpak OD-H column (250×4.6 mm) with isocratic 97.5 hexanes and 2.5% isopropanol mobile phase (5 μL injected). Using a UV detector set to 210 nm, enantiomer #1 (major) eluted at 7.4 minutes and enantiomer #2 (minor) eluted at 7.9 minutes. The enantiopurity was determined to be 98:2 er.

(2R,3R)-3-(o-tolyl)butan-2-yl acetate: 1H NMR (400 MHz, Chloroform-d) δ 7.23-7.00 (m, 4H), 5.10 (dq, J=8.5, 6.3 Hz, 1H), 3.15 (dq, J=8.5, 6.9 Hz, 1H), 2.34 (s, 3H), 2.06 (s, 3H), 1.23 (d, J=6.9 Hz, 3H), 1.07 (d, J=6.3 Hz, 3H); 13C NMR (126 MHz, Chloroform-d) δ 170.8, 141.9, 135.6, 130.4, 126.4, 126.2, 126.1, 74.9, 39.7, 21.3, 20.0, 18.3, 17.8; IR (thin film): 2976, 1733, 1492, 1458, 1370, 1238, 1169, 1127, 1078, 1061, 1037, 1013, 969, 942, 870, 844, 759, 728.

Example D2.2. (2S,3S)-3-(o-tolyl)butan-2-ol and (2R,3R)-3-(o-tolyl)butan-2-yl dodecanoate

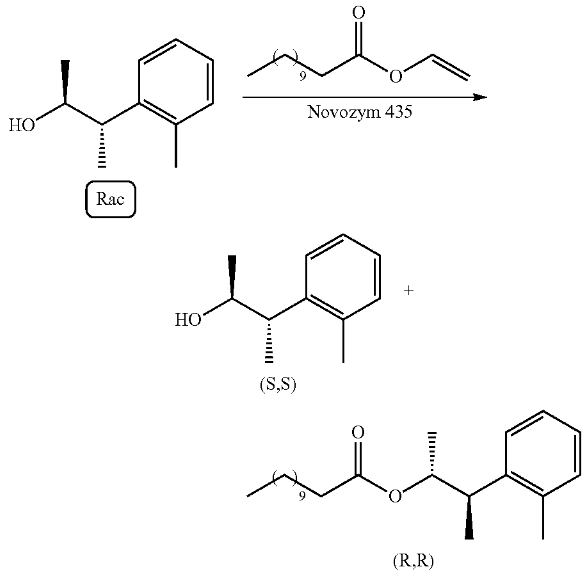

A 50 mL jacketed reactor equipped with overhead stirring and a temperature probe was charged with (2S,3S)- and (2R,3R)-3-(o-tolyl)butan-2-ol (5.0 g, 30.4 mmol, 1:1 mixture of enantiomers), MTBE (15 mL) and vinyl laurate (5.54 mL, 21.3 mol). Novozym® 435 (immobilized CAL-B lipase) (1.0 g, 20 wt %) was added and the reaction was stirred at 150 rpm and 40° C. overnight. The reaction mixture was cooled to RT and filtered to remove the immobilized enzyme. The immobilized enzyme was washed with MTBE and the combined filtrate was concentrated. The crude material was purified via silica gel chromatography (gradient 0-15% acetone in hexanes) to afford (2S,3S)-3-(o-tolyl)butan-2-ol (1.99 g, 12.13 mmol, 40% yield) as a pale yellow oil and (2R,3R)-3-(o-tolyl)butan-2-yl dodecanoate (1.72 g, 4.96 mmol, 16% yield) as a pale yellow oil.

Analytical data for (2S,3S)-3-(o-tolyl)butan-2-ol matched that of Example D2.1. Chiral HPLC analysis of D2 was performed using a Chiralpak IA column (250×4.6 mm) with isocratic 97.5% hexanes and 2.5% isopropanol mobile phase (5 μL injected). Using a UV detector set to 210 nm, enantiomer #1 (major) eluted at 7.4 minutes and enantiomer #2 (minor) eluted at 8.1 minutes. The enantiopurity was determined to be 99:1 er (enantiomeric ratio).

(2R,3R)-3-(o-tolyl)butan-2-yl dodecanoate: 1H NMR (500 MHz, Chloroform-d) δ 7.21-7.07 (m, 4H), 5.10 (dq, J=8.5, 6.2 Hz, 1H), 3.14 (dq, J=8.6, 6.9 Hz, 1H), 2.34 (s, 3H), 2.33-2.29 (m, 2H), 1.68-1.57 (m, 2H), 1.33-1.25 (m, 16H), 1.23 (d, J=6.9 Hz, 3H), 1.06 (d, J=6.2 Hz, 3H), 0.90-0.86 (m, 3H); 13C NMR (126 MHz, CDCl3) δ 173.5, 142.1, 135.5, 130.4, 126.4, 126.2, 126.1, 74.6, 39.9, 34.8, 31.9, 29.6, 29.5, 29.4, 29.3, 29.2, 25.1, 22.7, 20.0, 18.5, 17.8, 14.1; IR (thin film): 2923, 2853, 1732, 1492, 1457, 1375, 1249, 1167, 1078, 1035, 1009, 970, 939, 878, 758, 727 cm-1.

Example D2.3. (2S,3S)-3-(o-tolyl)butan-2-ol and (2R,3R)-3-(o-tolyl)butan-2-yl acetate

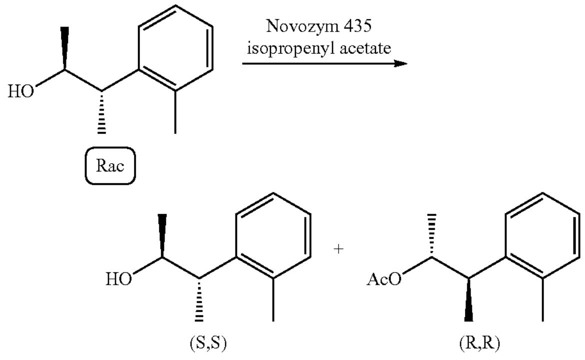

A 1 L jacketed reactor equipped with overhead stirring and temperature probe was charged with (2S,3S)- and (2R,3R)-3-(o-tolyl)butan-2-ol (54.1 g, 329 mmol, 1:1 mixture of enantiomers), and isopropenyl acetate (143 mL, 3.3 mol). Novozym® 435 (immobilized CAL-B lipase) (12.5 g, 25 wt %) was added and the reaction was stirred at 40° C. overnight. The reaction mixture was cooled to RT and filtered to remove the immobilized enzyme. The immobilized enzyme was washed with MTBE and the combined filtrate was concentrated. The crude material was purified via silica gel chromatography (gradient ethyl acetate in hexanes) to afford (2S,3S)-3-(o-tolyl)butan-2-ol (22 g, 127 mmol, 40% yield) as a pale yellow oil and (2R,3R)-3-(o-tolyl)butan-2-yl acetate (31.7 g, 151 mmol, 46% yield) as a colorless oil. 1H NMR (400 MHz, Chloroform-d) δ 7.19-7.07 (m, 4H), 3.91 (p, J=6.4 Hz, 1H), 3.01 (p, J=6.9 Hz, 1H), 2.34 (s, 3H), 1.30 (d, J=7.0 Hz, 3H), 1.12 (d, J=6.3 Hz, 3H).

Analytical data for (2S,3S)-3-(o-tolyl)butan-2-ol matched that of Example D2.1. Chiral HPLC analysis of D2 was performed using a Chiralpak IA column (250×4.6 mm) with isocratic 97.5 hexanes and 2.5% isopropanol mobile phase (5 μL injected). Using a UV detector set to 210 nm, enantiomer #1 (major) eluted at 7.4 minutes and enantiomer #2 (minor) eluted at 7.9 minutes. The enantiopurity was determined to be >99:1 er.

Example D3.1. (2S,3S)-3-(o-tolyl)butan-2-ol

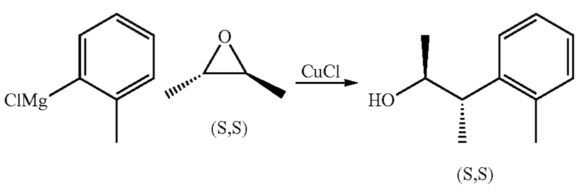

A 250 mL 3-neck round bottom flask equipped with a stirring bar, temperature probe, and nitrogen inlet was charged with o-tolylmagnesium chloride (1M in THF, 19.97 mL, 19.97 mmol). The reaction flask was cooled to 0° C., at which time solid copper (I) chloride (0.13 g, 1.33 mmol) was added to the flask. After stirring for 30 min, (2S,3S)-2,3-dimethyloxirane (0.960 g, 13.31 mmol) in toluene (30 mL) was added to the mixture via syringe. The reaction was stirred overnight and allowed to warm to room temperature.

After 21 h, the reaction was cooled to 0° C. and non-saturated ammonium chloride (6.14 mL, 18.41 mmol) was added via syringe. The reaction mixture was stirred for 1.5 hours. The contents were transferred to a separatory funnel and the organic layer was separated and washed with brine (50 mL). The organic layer was dried over sodium sulfate, filtered, and concentrated in vacuo. The crude material was dissolved in DCM and loaded onto a 40 g silica gel cartridge and purified via silica gel chromatography (EtOAc/hexanes gradient) to afford the title compound as a light yellow oil (0.6 g, 3.65 mmol, 27% yield). Analytical data matched that from Example D1.1; Enantiomeric ratio measured by Chiral HPLC (Chiralcel OD-H; 40° C.; 210 nm; isocratic 2.5% IPA/97.5% hexanes, 1.0 mL/min), er=>99:1.

Example D3.2. (2S,3S)-3-(o-tolyl)butan-2-ol

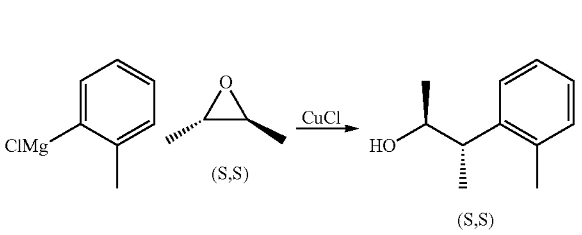

A 100 mL 3-neck round bottom flask equipped with a stirring bar, temperature probe, and nitrogen inlet was charged with o-tolylmagnesium chloride (1M in THF, 27.8 mL, 27.8 mmol). The reaction flask was cooled to 15° C., at which time solid copper (I) chloride (0.11 g, 1.11 mmol) was added to the flask. After stirring for 15 min, (2S,3S)-2,3-dimethyloxirane (2.7 g, 22.3 mmol, 60 wt % in toluene) was added to the mixture via syringe. Analysis showed starting material still present. More o-tolylmagnesium chloride (1M in THF, 22.3 mL, 22.3 mmol) was added. The reaction was cooled to 0° C. and aqeuous ammonium acetate (75 mL) was added via syringe. The reaction mixture was stirred for 30 min open to air. The contents were transferred to a separatory funnel and the organic layer was separated and washed with brine (40 mL). The organic layer was dried over sodium sulfate, filtered, and concentrated to afford the title compound as a colorless oil (2.9 g, 90% purity, 16.1 mmol, 72% yield). Analytical data matched that from Example D1.1; Enantiomeric ratio measured by Chiral HPLC (Chiralcel OD-H; 40° C.; 210 nm; isocratic 2.5% IPA/97.5% hexanes, 1.0 mL/min), er=95:5.

Example D3.3. (2S,3S)-3-(o-tolyl)butan-2-ol

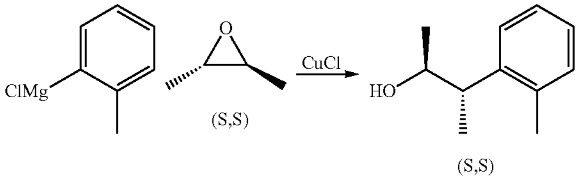

To a dry 50 mL 3 neck-flask equipped with a temperature probe, stir bar and a nitrogen inlet, was added solid copper(I) chloride (28 mg, 0.28 mmol) and THF (5 mL) followed by o-tolylmagnesium chloride (1 M in THF) (7 mL, 7.0 mmol) and the mixture was stirred at RT for 30 min. To this mixture was added (2S,3S)-2,3-dimethyloxirane (530 mg, 7.00 mmol) and the resulting mixture was stirred for 21 h. The mixture was quenched with saturated ammonium chloride (10 mL), stirred open to air for 30 min and the layers were separated. The dark blue aqueous layer was back extracted with EtOAc (2x20 mL). The combined organic layers were washed with 2N NaOH (10 mL), followed by brine (20 mL) then dried over magnesium sulfate and then concentrated under vacuum to provide (2S,3S)-3-(o-tolyl)butan-2-ol (675 mg, 59% yield) as a pale yellow oil. Analytical data matched that from Example D1.1; Enantiomeric ratio measured by Chiral HPLC (Chiralcel OD-H; 40° C.; 210 nm; isocratic 2.5% IPA/97.5% hexanes, 1.0 mL/min), er=98.5:1.5.

Example D4.1. (2S,3S)-3-(o-tolyl)butan-2-ol

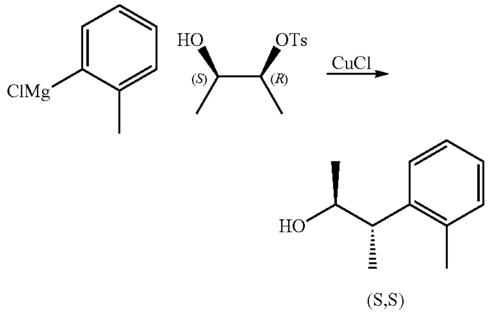

To a 10 mL flask under nitrogen was added copper(I) chloride (0.41 mg, 4.09 μmol) followed by o-tolylmagnesium chloride (1M in THF) (900 μL, 0.9 mmol) and the mixture was stirred at rt for 30 min. To this was added a solution of (2R,3S)-3-hydroxybutan-2-yl 4-methylbenzenesulfonate (100 mg, 0.41 mmol) in THF (0.5 mL) and the resulting mixture was stirred for 1 h. The mixture was continued to stir for 18 h at rt after which UPLC indicated completion. The mixture was quenched with 5% aq. acetic acid and extracted with MTBE. The combined MTBE extracts were washed with 1N NaOH, then dried over MgSO4, filtered and concentrated under vacuum. The resulting oil (~70 mg) was purified by column chromatography (4 g ISCO gold cartridge, 5-60% acetone/hexanes) to provide (2S,3S)-3-(o-tolyl)butan-2-ol as a colorless oil (12 mg, 16% yield). Enantiomeric ratio measured by Chiral HPLC analysis (AD-H column 4.6 mmΦx250 mm; 5 μm particle size; 40° C.; isocratic IPA/Hexanes 97.5/2.5, er 97:3.

Example D4.2. (2S,3S) and (2R,3R)-3-(o-tolyl)butan-2-ol

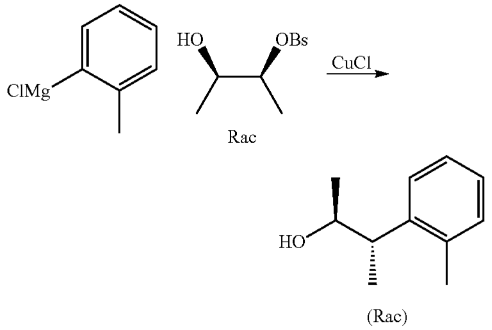

To a 10 mL flask equipped with a stir bar and a nitrogen inlet was added copper(I) chloride (5.16 mg, 0.052 mmol) followed by o-tolylmagnesium chloride (1 M in THF) (11.5 mL, 11.5 mmol) and the mixture was stirred at rt for 30 min. To this was added a solution of (2S,3R)- and (2R,3S)-3-hydroxybutan-2-yl benzenesulfonate (1.2 g, 5.21 mmol) in THF (0.5 mL) and the resulting mixture was stirred for 18 h. The mixture was quenched with saturated ammonium chloride (10 mL), stirred open to air for 30 min and the layers were separated. The dark blue aqueous layer was back extracted with EtOAc (2×20 mL). The combined organic layers were washed with 2N NaOH (10 mL), followed by brine (20 mL) then dried over magnesium sulfate and then concentrated under vacuum to provide a colorless oil. The crude product was purified by column chromatography (4 g ISCO gold, 5-60% acetone/hexanes) to provide (2S,3S)- and (2R,3R)-3-(o-tolyl)butan-2-ol (150 mg, 18% yield) as a colorless oil. Analytical data matched that from Example D1.1.

Example G1.1. (2S,3S)- and (2R,3R)-2,3-epoxybutane

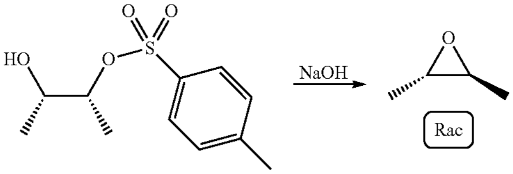

A 250 mL flask, was charged with rac-(2R,3S)-3-hydroxybutan-2-yl 4-methylbenzenesulfonate (50.1 g, 205 mmol) followed by toluene (50 mL). Aqueous NaOH (2M, 154 mL, 307.5 mmol) was added dropwise via an additional funnel. After 1 hour, 100 mL of 5% acetic acid was added to the reaction and the mixture was stirred for 30 mins. The layers were separated and the organic layer was washed with brine.

The distillation set-up involved a 250 mL, 3-neck round bottomed flask equipped with an internal temperature probe, a distillation head with an overhead thermocouple, an ice-water cooled condenser and nitrogen inlet. The flask was charged with 82.5 g of the toluene mixture obtained above. The flask was heated to 90° C. Two fractions of trans-2,3-epoxybutane were collected with a vapor temperature range of 58-80° C. Fraction 1: 6.1 g, 90% purity; Fraction 2: 3.7 g, 33% pure, thus resulting in a combined yield of 9.8 g (53% yield, 75% overall purity). 1H NMR (300 MHz, CDCl3) δ 2.78-2.66 (m, 1H), 1.29 (d, J=4.9 Hz, 2H). 13C NMR (75 MHz, CDCl3) δ 55.65, 17.56.

Example G1.2. (2S,3S)- and (2R,3R)-2,3-epoxybutane

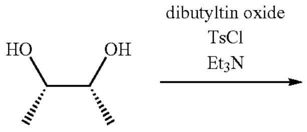

-continued

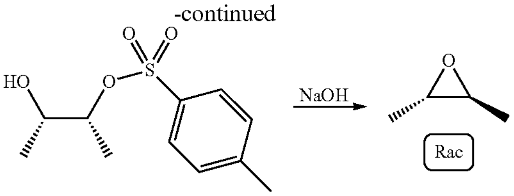

A 1 L reactor equipped with an overhead stirrer, pH probe, and thermocouple was charged with meso-butane-2,3-diol (25 g, 277 mmol) followed by CPME (200 mL). To this suspension was added p-toluenesulfonyl chloride (55.4 g, 291 mmol) and dibutyl tin oxide (0.132 g, 0.528 mmol), followed by the addition of triethylamine (47.9 mL, 343 mmol). After 20 h, the mixture was cooled to 15° C. and 1M HCl (80 mL) was added. The mixture was stirred for 30 min and the bottom layer was drained. The organic layer was washed with brine and the layers were separated. The organic layer containing the monotosylate was cooled to 10° C. and 2 M NaOH (200 mL) was added dropwise. After 2 hours, complete conversion to (2S,3S)- and (2R,3R)-2,3-dimethyloxirane was observed. The bottom aqueous layer was drained and the organic layer was first washed with 5% aqueous acetic acid, followed by brine.

The CPME/epoxide mixture was purified via simple distillation at ambient pressure and in-pot temperature of 90-110° C. Two fractions were collected: Fraction #1 (6.4 g) with a vapor temperature −53° C.; and #2 (12.4 g) with a vapor temperature in the range of 53-80° C. contained −50% CPME. In all, 18.8 g (64% yield, 65 wt % in CPME) of (2S,3S)- and (2R,3R)-2,3-epoxybutane was produced.

Example G1.3. (2S,3S)-2,3-epoxybutane

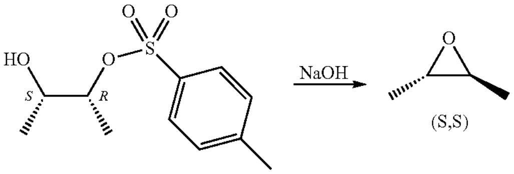

A 2-dram vial was charged with (2R,3S)-3-hydroxybutan-2-yl 4-methylbenzenesulfonate (50 mg, 0.205 mmol) followed by deuterated chloroform (1 ml) and the mixture was cooled to 10° C. 1N aqueous sodium hydroxide (246 µl, 0.246 mmol) was added dropwise and the mixture was stirred at rt for 30 mins. Stirring was stopped and the layers were separated. The CDCl3 layer was passed over magnesium sulfate and the clear solution was analyzed by NMR. 1H NMR (500 MHz, Chloroform-d) δ 2.77-2.67 (m, 2H), 1.29 (d, J=4.9 Hz, 6H). The enantiomeric excess was determined by NMR Chiral analysis:

1) Chiral epoxide was tested using both enantiomers of Perkle's reagent.
2) Samples were prepared at −20 mM epoxide, −80 mM Perkle's reagent, in CDCl3. Material was quantified using ERETIC NMR.
3) Analysis was performed at 0° C. on the Prodigy cryoprobe. Shimming was done with Topspin, followed by the "tune" macro for touchups.
4) Analysis was performed upon the epoxide protons at 2.99 ppm. The selective 1 D homonuclear decoupling routine was used to decouple the protons from the epoxide methyl groups, collapsing them into two singlets.

5) Lineshape modeling was performed using Mnova.

| Perkle Reagent isomer | Result (ee) | Comments |
|---|---|---|
| R(−) | 95.42498 | Avg of 5 measurements |
| S(+) | 95.79887 | Avg of 6 measurements |

Example G1.4. (2S,3S)-2,3-epoxybutane

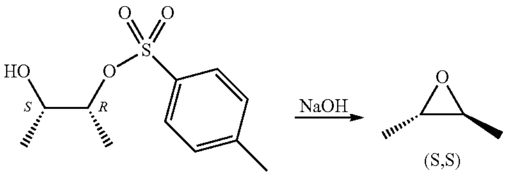

A 250 mL 3-neck round bottom flask equipped with a stir bar, temperature probe, and nitrogen inlet was charged with (2R,3S)-3-hydroxybutan-2-yl 4-methylbenzenesulfonate (14.3 g, 58.5 mmol) and toluene (30 mL). The toluene solution was treated with sodium hydroxide (43.9 mL, 88 mmol) and stirred at room temperature. The reaction was terminated after 2 h stirring and the mixture was transferred to a separatory funnel. The organic layer was separated, dried over sodium sulfate, and filtered. The in-pot yield was determined by GC using an internal standard. The solution of epoxide in toluene (34.3 g, 64% yield) was used in the next reaction without further manipulation.

A 100 mL 3-neck round bottom flask equipped with a stirring bar, temperature probe, and nitrogen inlet was charged with o-tolylmagnesium chloride (27.4 ml, 27.4 mmol). The reaction flask was stirred at room temperature, at which time solid copper (I) chloride (0.090 g, 0.912 mmol) was added to the flask. After stirring for 30 min, (2S,3S)-2,3-dimethyloxirane (0.885 g, 12.27 mmol) in toluene (~30 ml) was added to the mixture via syringe. The reaction was monitored by GC. After 5 h, an additional 0.5 equiv o-tolylmagnesium chloride (9.1 mL, 9.1 mmol) was added due to incomplete consumption of epoxide. After 21 h, the reaction was cooled to 0° C. and non-saturated ammonium chloride (15.2 ml, 45.6 mmol) was added via syringe. The reaction mixture was stirred for 1.5 h. The contents were transferred to a separatory funnel and the organic layer was separated and washed with brine (100 ml). The organic layer was dried over sodium sulfate, filtered, and concentrated in vacuo. The crude material was dissolved in DCM and loaded onto a silica gel cartridge and purified via silica gel chromatography (EtOAc/hexanes gradient) to afford (2S,3S)-3-(o-tolyl)butan-2-ol as a light yellow oil (2.4 g, 14.6 mmol, 80% yield). Analytical data matched that from Example G1.1; Enantiomeric ratio measured by Chiral HPLC (Chiralcel OD-H; 40° C.; 210 nm; isocratic 2.5% IPA/97.5% hexanes, 1.0 mL/min), er=94:6.

Example G1.5. (2S,3S)- and (2R,3R)-2,3-epoxybutane

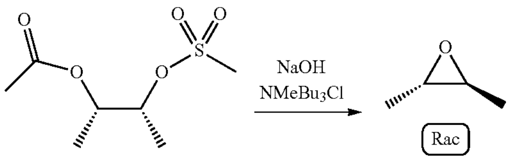

A 250 mL 3-neck round bottom flask equipped with a stir bar, temperature probe, and nitrogen inlet was charged with (2R,3S)- and (2S,3R)-3-((methylsulfonyl)oxy)butan-2-yl acetate (15 g, 71.3 mmol) and toluene (45 mL). Sodium hydroxide (17.84 mL, 214 mmol, 12 N) was added followed by methyl tributyl ammonium chloride (2.33 mL, 7.13 mmol, 75 wt % in water). The biphasic mixture was stirred at room temperature. After 18 h, the reaction mixture was transferred to a separatory funnel and the phases separated. The organic layer was washed with water, then dried over sodium sulfate and filtered to give a toluene solution of (2S,3S)- and (2R,3R)-2,3-dimethyloxirane. Quantitative GC analysis with 2,2,4,4,6,8,8-heptamethylnonane (HMN) as an internal standard showed an in-pot yield of 83%. A short path distillation head was connected to the round bottom flask containing the solution of epoxide in toluene, and the reaction mixture was heated. At a pot temperature of 125° C., a colorless liquid distilled overhead. Two fractions were collected, with NMR analysis indicating that both fractions contained epoxide. The fractions were combined to give 4.60 g of the epoxide as a 30 wt % solution in toluene (1.36 g, 26.5%). Analytical data matched that of G1.1

Example G1.6. (2S,3S)-2,3-epoxybutane

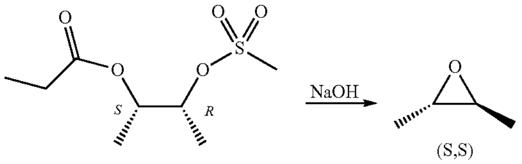

A 1 L 3-neck round bottom flask equipped with a nitrogen inlet, overhead stirring and temperature probe in a water bath was charged with (2S,3R)-3-(tosyloxy)butan-2-yl propionate (50 g, 69 wt %, 155 mmol) and toluene (200 mL). Water (200 mL) followed by sodium hydroxide (50 wt %, 41.2 mL, 780 mmol) was added and the reaction was stirred at room temperature for 7 h. The reaction mixture was allowed to settle and transferred to a separatory funnel. The layers were separated and the organic layer was washed with 5% acetic acid (~150 mL) and then brine (150 mL×2) The organic layer was dried with anhydrous sodium sulfate overnight. The solution of the epoxide in toluene was distilled overhead. Three fractions were collected, with NMR analysis indicating that all fractions contained epoxide and toluene. The fractions were combined to give the title compound (4.8 g, 41% yield) as a solution in toluene. Analytical data matched that of G1.1. Enantiopurity was determined by taking the mixture into the next step, see example D3.2 for details.

Example G1.7. (2S,3S)- and (2R,3R)-2,3-epoxybutane

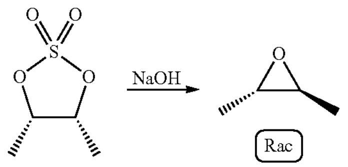

meso-4,5-Dimethyl-1,3,2-dioxathiolane-2,2-dioxide (6.82 g, 44.8 mmol) was placed in a 250 mL 3-neck flask equipped with a thermocouple and magnetic stir bar. Ethylene glycol (90.6 g) was added followed by 1M NaOH (90.32 g, 88 mL). After 3 d, 1H NMR (CDCl3) showed no cyclic sulfate and very clean formation of the trans epoxide. Quantitative GC analysis with 2,2,4,4,6,8,8-heptamethylnonane (HMN) as an internal standard showed an in-pot yield of 103%. A short path distillation head was connected, and the reaction mixture was heated. At a pot temperature of 85° C., a colorless liquid distilled overhead at 59° C. (536 mg, 20% yield). Analytical data matched that of example G1.1.

Example G1.8. (2S,3S)-2,3-epoxybutane

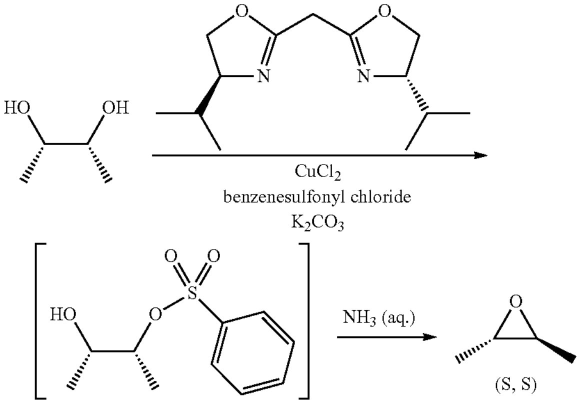

To a 1 liter reactor was added 360 mL 9:1 toluene:tAmOH. Bis((S)-4-isopropyl-4,5-dihydrooxazol-2-yl)methane (3.11 g, 10.43 mmol) was added as a solution in 9:1 toluene:tAmOH (20 mL toluene:tAmOH used) and the reaction mixture was stirred at room temperature. Copper(II) chloride (1.40 g, 10.43 mmol) was added. The jacket temperature was set to 8° C. and the reaction was allowed to stir for 30 min. Potassium carbonate (104 g, 751 mmol) was added and 20 mL of 9:1 toluene:tAmOH was used to rinse residual solid into the reactor. After 20 min, meso-2,3-butanediol (40 g, 417 mmol) was added. Water (3.7 mL, 209 mmol) was added and the reaction mixture was stirred for 30 min. Benzenesulfonyl chloride (64.5 mL, 501 mmol) added in portions by syringe over 28 min. After 18 hours, reaction was sampled and sulfonate was found to be 89% ee by HPLC assay. Added 200 mL aqueous $NH_4OH$ (28% NH3) and 150 mL water. Stirring mixture was warmed to 20° C. and mixture was stirred for 24 hours. After 24 hours, it was found by NMR to be 97% conversion of the sulfonate to the epoxide. The resulting organic layer was separated and stirred with 250 mL saturated aqueous NaCl for 10 min. The resulting organics were isolated. This solution (354.1 g) was found to be 6.5 wt % epoxide which amounts to 76% yield. Analytical data matched that of example G1.1.

Example G1.9. (2S,3S)-2,3-epoxybutane

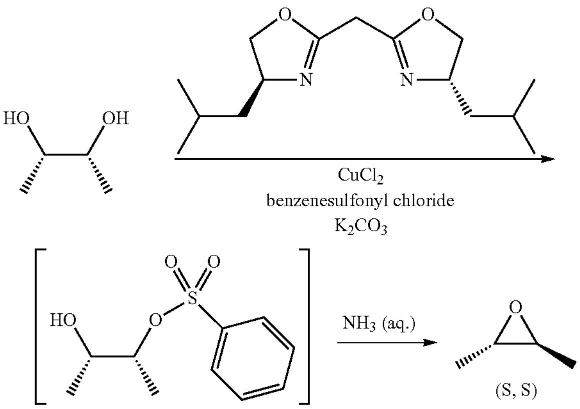

To a 1 liter reactor was added 360 mL 9:1 toluene:tAmOH. Bis((S)-4-isobutyl-4,5-dihydrooxazol-2-yl)methane (1.39 g, 4.17 mmol) was added as a solution in 9:1 toluene:tAmOH (20 mL toluene:tAmOH used) and the reaction mixture was stirred at room temperature. Copper(II) chloride (0.56 g, 4.17 mmol) was added. The jacket temperature was set to 8° C. and the reaction was allowed to stir for 60 minutes. Potassium carbonate (104 g, 751 mmol) was added and 20 mL of 9:1 toluene:tAmOH was used to rinse residual solid into the reactor. After 10 min, meso-2,3-butanediol (40 g, 417 mmol) was added. After 10 min, water (3.7 mL, 209 mmol) was added and the reaction mixture was stirred for 10 min. Benzenesulfonyl chloride (64.5 mL, 501 mmol) added in portions by syringe over 25 min. After 18 hours, reaction was sampled and sulfonate was found to be 94% ee by HPLC assay. Added 200 mL aqueous $NH_4OH$ (28% NH3) and 150 mL water. Stirring mixture was warmed to 20° C. and mixture was stirred for 24 hours. After 24 hours, it was found by NMR to be 97% conversion of the sulfonate to the epoxide. The resulting organic layer was separated and stirred with 250 mL saturated aqueous NaCl for 10 min. The resulting organics were isolated. This solution (352.8 g) was found to be 7.3 wt % epoxide which amounts to 86% yield. Analytical data matched that of example G1.1.

Example G1.10. (2S,3S)-2,3-epoxybutane

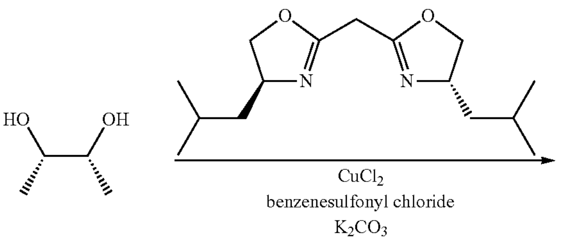

-continued

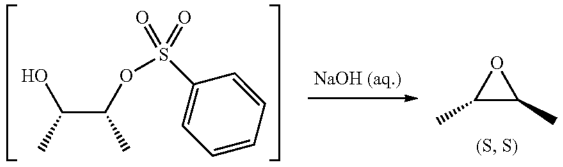

To a 250 mL reactor was added 90 mL 9:1 toluene: tAmOH. Bis((S)-4-isobutyl-4,5-dihydrooxazol-2-yl)methane (0.35 g, 1.04 mmol) was added as a solution in 9:1 toluene:tAmOH (5 mL toluene:tAmOH used) and the reaction mixture was stirred at room temperature. Copper(II) chloride (0.14 g, 1.04 mmol) was added. The jacket temperature was set to 8° C. and the reaction was allowed to stir for 60 min. Potassium carbonate (28 g, 188 mmol) was added and 5 mL of 9:1 toluene:tAmOH was used to rinse residual solid into the reactor. After 10 min, meso-2,3-butanediol (10 g, 104 mmol) was added. After 10 min, water (0.94 mL, 52.3 mmol) was added and the reaction mixture was stirred for 10 min. Benzenesulfonyl chloride (16.1 mL, 125 mmol) added in portions by syringe over 25 min. After 18 hours, reaction was sampled and 100 ml of 3.1 M aqueous NaOH was added to the reaction. Stirring mixture was warmed to 20° C. and mixture was stirred for 20 minutes. After 20 min, it was found by NMR to be >98% conversion of the sulfonate to the epoxide. The aqueous layer was removed. The resulting organic layer was separated and stirred with 62 mL saturated aqueous NaCl for 10 min. The resulting organics were isolated. This solution was analyzed and found to be 6.7 wt % epoxide which amounts to 80% yield. Analytical data matched that of example G1.1.

Example G1.11. Base screening for (2S,3S)-2,3-epoxybutane

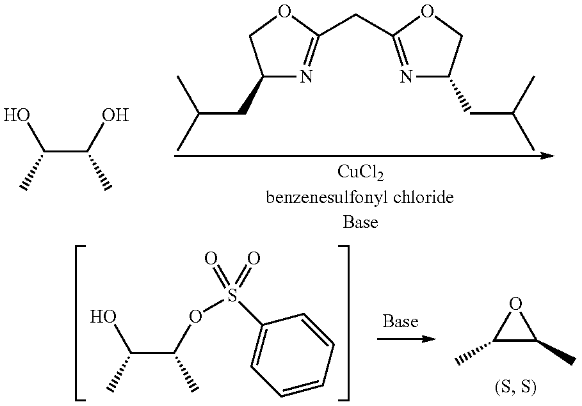

To a 2 dram vial was added bis((S)-4-isobutyl-4,5-dihydrooxazol-2-yl)methane (29.6 mg, 0.111 mmol) followed by toluene (5 mL). Copper(II) chloride (14.9 mg, 0.11 mmol) was added and the mixture was stirred for 10 min. The solution was then split equally into 5 vials with stir bars. Base was added into each vial according to the recipe below and stirred for 10 min.

A: Potassium carbonate (186 mg, 1.2 eq.)

B: Potassium carbonate (464 mg, 3 eq.)

C: Cesium carbonate (723 mg, 2 eq.)

D: Potassium carbonate (186 mg, 1.2 eq.)

E: Potassium carbonate (186 mg, 1.2 eq.)

(2R,3S)-butane-2,3-diol (100 mg, 1.11 mmol) was added to each vial. Benzenesulfonyl chloride (0.172 mL, 1.33 mmol) was then added last to each vial. The mixture was stirred at ambient for 16 h and analyzed by H NMR. Additional base was added to vial A, D and E according to the recipe below.

A: Diisopropylethyl amine (0.776 mL, 4 eq)

D: DBU (335 mL, 2 eq.)

E: Proton Sponge (476 mg, 2 eq.)

Each the reaction mixture was then heated to 50° C. and stirred ~16 h. H NMR analysis indicated conversions of the sulfonate to the epoxide below.

| Run | Initial Base | Additional Base | Conversion |
|---|---|---|---|
| A | Potassium carbonate (186 mg, 1.2 eq.) | Diisopropylethyl amine (0.776 mL, 4 eq) | >95% |
| B | Potassium carbonate (464 mg, 1 eq.) | None | 90% |
| C | Cesium carbonate (723 mg, 2 eq.) | None | 50% |
| D | Potassium carbonate (186 mg, 1.2 eq.) | DBU (335 mL, 2 eq.) | >95% |
| E | Potassium carbonate (186 mg, 1.2 eq.) | Proton Sponge (476 mg, 2 eq.) | 30% |

Example H1.1 (2S,3R)- and (2R,3S)-3-hydroxybutan-2-yl 4-methylbenzenesulfonate

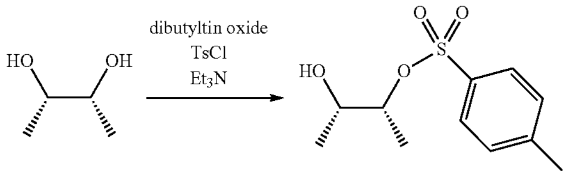

A 1 L jacketed reactor equipped with an overhead stirrer, pH probe, and thermocouple was charged with meso-(2R, 3S)-butane-2,3-diol (25 g, 277 mmol), followed by DCM (200 mL). To this suspension was added p-toluenesulfonyl chloride (55.4 g, 291 mmol) and dibutyltin oxide (0.329 g, 1.321 mmol), followed by triethylamine (47.9 mL, 343 mmol). After 2 hours, 1M HCl (80 mL) was added to the reaction and the mixture was stirred for 15 mins. The layers were separated. The DCM layer was washed first with 1M HCl (20 mL) and finally with brine. The DCM layer was then dried over sodium sulfate and concentrated under vacuum to produce racemic-(2S,3R)-3-hydroxybutan-2-yl 4-methylbenzenesulfonate (74.8 g, 100% yield). 1H NMR (400 MHz, CDCl3) δ 7.83-7.78 (m, 2H), 7.35 (d, J=8.1 Hz, 2H), 4.54 (qd, J=6.5, 3.4 Hz, 1H), 3.87 (qd, J=6.5, 3.4 Hz, 1H), 2.44 (s, 3H), 1.20 (d, J=6.5 Hz, 3H), 1.10 (d, J=6.5 Hz, 3H); 13C NMR (101 MHz, CDCl3) δ 144.85, 134.02, 129.89, 127.73, 83.25, 69.27, 21.62, 17.73, 14.96; IR (thin film): 3419, 3067, 2982, 2839, 1598, 1495, 1448, 1349, 2192, 1211, 1188, 1172, 1098, 1018, 977, 900, 814, 786, 705, 666 cm −1.

Example H1.2 (2R,3S)-3-hydroxybutan-2-yl 4-methylbenzenesulfonate

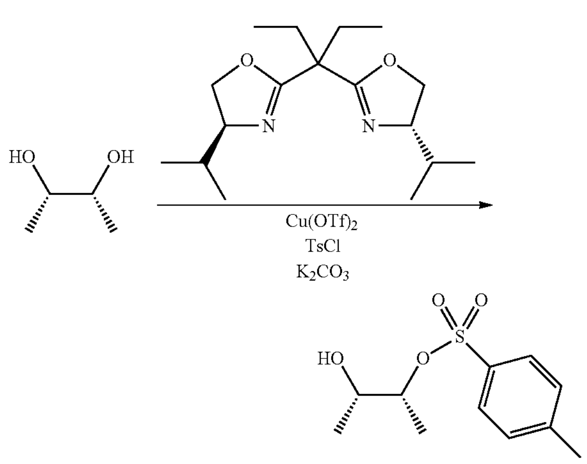

To a 10 ml vial under nitrogen was added (4S,4'S)-(−)-2,2'-(3-Pentylidene)bis(4-isopropyloxazoline) (15.56 mg, 0.053 mmol) followed by DCM (2 mL) and the mixture was homogenized. To this was added copper (II) trifluoromethanesulfonate (19 mg, 0.05 mmol) and the resulting mixture was stirred for 30 min. Solid potassium carbonate (110 mg, 0.79 mmol) was added in one portion followed by dropwise addition of (2R,3S)-butane-2,3-diol (50 mg, 0.56 mmol) which was a 95:5 mixture of the meso-rac forms of the diol. The resulting green colored mixture was stirred for 18 h at rt. The reaction was diluted with DCM and washed with brine. The layers were separated, and the DCM layer was dried over MgSO4 and concentrated under vacuum. The crude material was purified via ISCO column chromatography (4 g SiO2-gold cartridge, 5-60% acetone-hexanes) and the product eluted at ~30% acetone-hexanes. The combined fractions were concentrated under vacuum to provide (2R,3S)-3-hydroxybutan-2-yl 4-methylbenzenesulfonate (110 mg, 0.428 mmol, 81% yield) as a colorless oil. Chiral HPLC analysis showed 95% ee. Enantiomeric ratio measured by Chiral HPLC (Chiralcel® OJ-H; 4.6 mmΦx250 mm; 5 μm particle size; 254 nm; isocratic 5% IPA/95% hexanes, 1.0 mL/min), er=95:5. Analytical data matched that of example H1.1.

Example H1.3 (2R,3S)-3-hydroxybutan-2-yl 4-methylbenzenesulfonate

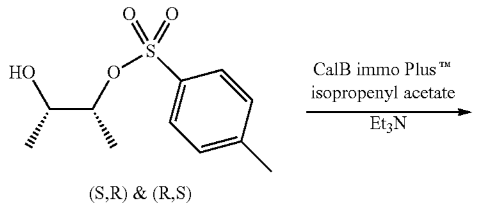

(S,R) & (R,S)

-continued

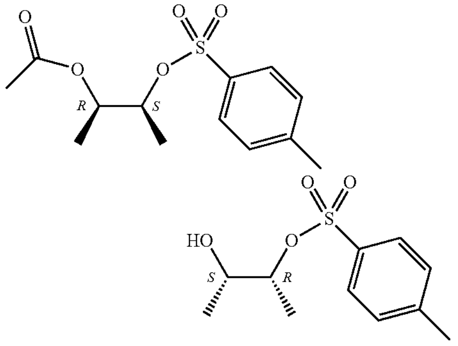

To a 500 mL single neck flask equipped with a stir bar and nitrogen inlet was added racemic (2S,3R)- and (2R,3S)-3-hydroxybutan-2-yl 4-methylbenzenesulfonate (40 g, 164 mmol) and toluene (200 mL). Triethylamine (8.0 mL, 57.3 mmol), isopropenyl acetate (37.4 mL, 344 mmol), and Cal B Immo Plus (8 g, 20 wt %) were added sequentially. After stirring overnight at room temperature, the slurry was filtered, washing the immobilized enzyme with toluene. The filtrate was transferred to a separatory funnel and washed with aqueous ammonium chloride. The organic layer was separated, dried over sodium sulfate, filtered, and concentrated in vacuo. The crude material was dissolved in DCM and loaded onto a silica gel cartridge and purified via silica gel chromatography (EtOAc/hexanes gradient) to afford (2R,3S)-3-hydroxybutan-2-yl 4-methylbenzenesulfonate as a colorless oil (13.6 g, 55.7 mmol, 68% yield). Analytical data for (2R,3S)-3-hydroxybutan-2-yl 4-methylbenzenesulfonate matched that of Example H1.1 Enantiomeric ratio measured by Chiral HPLC (Chiralcel OJ-H; 40° C.; 220 nm; isocratic 5% IPA/95% hexanes, 1.0 mL/min), er=94:6. Analytical data for (2R,3S)-3-(tosyloxy)butan-2-yl acetate: 1H NMR (500 MHz, CDCl3) δ 7.82-7.77 (m, 2H), 7.37-7.32 (m, 2H), 4.81 (qd, J=6.6, 3.1 Hz, 1H), 4.67 (qd, J=6.6, 3.0 Hz, 1H), 2.45 (s, 3H), 1.90 (s, 3H), 1.26 (d, J=6.6 Hz, 3H), 1.18 (d, J=6.6 Hz, 3H); 13C NMR (126 MHz, CDCl3) δ 170.29, 144.69, 134.09, 129.79, 127.86, 79.43, 71.22, 21.63, 20.95, 16.63, 13.92; IR (thin film): 2989, 2944, 2880, 1733, 1598, 1495, 1447, 1354, 1307, 1237, 1189, 1174, 1091, 1022, 982, 951, 911, 869, 833, 815, 782, 706, 668. Enantiomeric ratio measured by Chiral HPLC (Chiralcel OJ-H; 40° C.; 220 nm; isocratic 5% IPA/95% hexanes, 1.0 mL/min), er=93:7.

Example H2.1. (2R,3S)- and (2S,3R)-3-((methylsulfonyl)oxy)butan-2-yl acetate

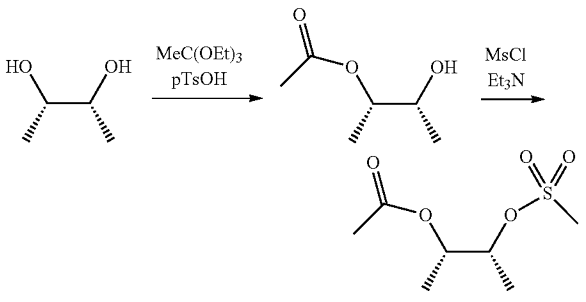

A 1 L reactor equipped with a temperature probe, nitrogen inlet and overhead stirring was charged with meso-2,3-butanediol (90 g, 999 mmol), THF (454 mL) and triethylorthoacetate (239 mL, 1298 mmol). p-Toluenesulfonic acid monohydrate (0.950 g, 4.99 mmol) was added and the reaction was stirred at 21° C. After 4 h, water (32.4 mL, 1798 mmol) was added and the reaction was stirred at 21° C. overnight. The reaction mixture was transferred to a single-neck round bottom flask and concentrated in vacuo to afford (2R,3S)- and (2S,3R)-3-hydroxybutan-2-yl acetate as a colorless oil (136 g, 93% yield). The material was used without further purification.

1H NMR (500 MHz, CDCl3) δ 4.86 (qd, J=6.5, 3.4 Hz, 1H), 3.89 (qd, J=6.5, 3.4 Hz, 1H), 2.08 (s, 3H), 1.21 (d, J=6.5 Hz, 3H), 1.17 (d, J=6.5 Hz, 3H); 13C NMR (126 MHz, CDCl3) δ 170.9, 74.4, 69.4, 21.3, 17.9, 14.1; IR (thin film): 3426, 2983, 2941, 1715, 1372, 1239, 1070, 1045, 1006, 951, 915, 857, 735.

A 1 L reactor equipped with a temperature probe, nitrogen inlet and overhead stirring was charged with solution of (2R,3S)- and (2S,3R)-3-hydroxybutan-2-yl acetate (15 g, 113 mmol) in ethyl acetate (227 mL) and cooled to 0° C. Triethylamine (28.5 mL, 204 mmol) was added via syringe. After stirring for 10 mins, methanesulfonyl chloride (11.9 mL, 153 mmol) was added slowly via syringe resulting in a suspension. After stirring for 1 h, 1 N HCl was added and the biphasic mixture was stirred for 1.5 h. The reaction mixture was transferred to a separatory funnel. The organic layer was separate, dried over sodium sulfate, filtered and concentrated in vacuo to afford the title compound as a waxy off-white solid (21.6 g, 91%). The material was used without further purification.

Analytical data: 1H NMR (500 MHz, CDCl3) δ 4.99 (qd, J=6.6, 2.9 Hz, 1H), 4.88 (qd, J=6.6, 2.9 Hz, 1H), 3.05 (s, 3H), 2.09 (s, 3H), 1.41 (d, J=6.6 Hz, 3H), 1.27 (d, J=6.6 Hz, 3H); 13C NMR (126 MHz, CDCl3) δ 170.2, 79.5, 71.3, 38.7, 21.1, 16.9, 13.9; IR (thin film): 3460, 2991, 2943, 1733, 1448, 1347, 1237, 1170, 1078, 1025, 970, 915, 870, 835, 805, 745.

Example H2.2.1
(2S,3R)-3-((methylsulfonyl)oxy)butan-2-yl propionate

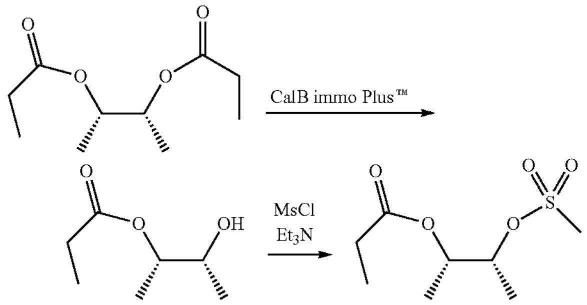

A 100 mL round bottom flask equipped with a stir bar and nitrogen inlet was meso-butane-2,3-diyl dipropionate (10 g, 49.4 mmol), EtOH (20 mL) and Cal B Immo Plus (2.0 g, 20 wt %). The reaction was stirred at 25° C. for 6 days. The reaction was terminated by filtration of the slurry under vacuum. The immobilized enzyme beads were washed with EtOAc. The filtrate was concentrated in vacuo to deliver 6.75 g of the title compound (85% (2S,3R)-3-hydroxybutan-2-yl propionate by GC [DB-624, 30 m×0.25 mm, 1.4-μm film; 1.1 mL/min, 8.56 psi He, 0.2 uL, 250° C., 20:1 split; 40° C. for 5 min., 15° C./min to 260° C., hold 5 min]). 1H NMR (400 MHz, Chloroform-d) δ 4.88 (qd, J=6.5, 3.3 Hz, 1H), 3.89 (qd, J=6.5, 3.3 Hz, 1H), 2.35 (q, J=7.6 Hz, 2H), 2.02 (br s, 1H), 1.21 (d, J=6.5 Hz, 3H), 1.17 (d, J=6.5 Hz, 3H), 1.15 (t, J=7.6 Hz, 3H); 13C NMR (151 MHz, CDCl3) δ 174.37, 74.29, 69.49, 27.88, 18.02, 14.46, 9.16; IR (thin film) 3437, 2980, 2942, 2883, 1715, 1463, 1423, 1371, 1274, 1190, 1084, 1040, 1006, 982, 925, 898, 866, 807, 737. Enantiomeric ratio measured by Chiral HPLC (Chiralcel ID; 40° C.; 210 nm; isocratic 10% IPA/90% hexanes, 1.0 mL/min), er=>99:1.

A 500 mL 3-neck round bottom flask equipped with a nitrogen inlet, stirring bar and temperature probe was charged with a solution of (2S,3R)-3-hydroxybutan-2-yl propionate (3.5 g, 26.5 mmol) (69% (2S,3R)-3-hydroxybutan-2-yl propionate meso-2,3-butanediol and meso-butane-2,3-diyl dipropionate by GC) in toluene (50 mL). The solution was cooled to −10° C. under nitrogen and treated with triethylamine (6.64 mL, 47.7 mmol). After stirring for 10 mins, methanesulfonyl chloride (2.78 mL, 35.7 mmol) was added resulting in a suspension. The resulting mixture was stirred at 0° C. for 2 h. At 0° C., 1 N HCl (47.7 mL, 47.7 mmol) was added and stirred for 1.5 h. The suspension was transferred to a separatory funnel. The organic layer was washed by 50 mL sodium bicarbonate and dried over sodium sulfate. The organic layer was then concentrated to afford 2.8 g of the title compound. The unpurified product was used without further manipulation. Analytical data: 1H NMR (500 MHz, CDCl3) δ 5.00 (qd, J=6.5, 2.9 Hz, 1H), 4.87 (qd, J=6.6, 2.9 Hz, 1H), 3.05 (s, 3H), 2.36 (qd, J=7.5, 1.2 Hz, 2H), 1.41 (d, J=6.7 Hz, 3H), 1.27 (d, J=6.6 Hz, 3H), 1.15 (t, J=7.6 Hz, 3H); 13C NMR (126 MHz, CDCl3) δ 173.61, 79.66, 71.07, 38.64, 27.67, 16.94, 13.97, 8.98; IR (thin film): 2988, 2944, 1732, 1463, 1346, 1275, 1170, 1101, 1075, 1034, 1012, 969, 927, 905, 836, 806, 747 cm −1.

Example H2.2.2
(2S,3R)-3-((methylsulfonyl)oxy)butan-2-yl propionate

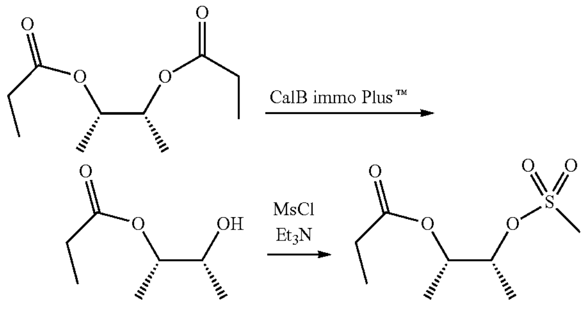

A 400 mL reactor equipped with a mechanical stirrer and nitrogen inlet was meso-butane-2,3-diyl dipropionate (49.5 g, 79 wt %, 193 mmol), EtOH (100 mL) and Cal B Immo Plus (20 g). The reaction was stirred at 25° C. for 70 h. The reaction was terminated by filtration of the slurry under vacuum. The immobilized enzyme were washed with EtOAc. The filtrate was concentrated in vacuo to deliver (2S,3R)-3-hydroxybutan-2-yl propionate (37 g, 69 wt %, 175 mmol, 90% yield). >99:1 dr as measured by GC analysis [DB-624, 30 m×0.25 mm, 1.4-μm film; 1.1 mL/min, 8.56 psi He, 0.2 uL, 250° C., 20:1 split; 40° C. for 5 min., 15° C./min to 260° C., hold 5 min]). Analytical data matched that of example H2.2.1.

A 1 L 3-neck round bottom flask equipped with a nitrogen inlet, overhead stirring and temperature probe was charged with (2S,3R)-3-hydroxybutan-2-yl propionate (36 g, 69 wt %, 170 mmol) and toluene (350 mL). Triethylamine (47.4 mL, 340 mmol) was added and the solution was cooled to 0° C. Methanesulfonyl chloride (16.6 mL, 212 mmol) was added resulting in a suspension. After the completion of the reaction, 1 N HCl (100 mL) was added to the reaction at 0° C. The mixture was transferred to a separatory funnel and the layers were separated. The organic layer was washed by 100 mL of aqueous sodium bicarbonate and dried over sodium sulfate. The organic layer was then concentrated to afford the title compound (50.1 g, 69% purity, 91% yield) as a pale yellow oil. Analytical data matched that of example H2.2.1. Enantiomeric ratio for this reaction sequence was determined by carrying out the subsequent steps, see Example G1.6 and Example D3.2.

Example 11.1. Bis((S)-4-isobutyl-4,5-dihydrooxazol-2-yl)methane

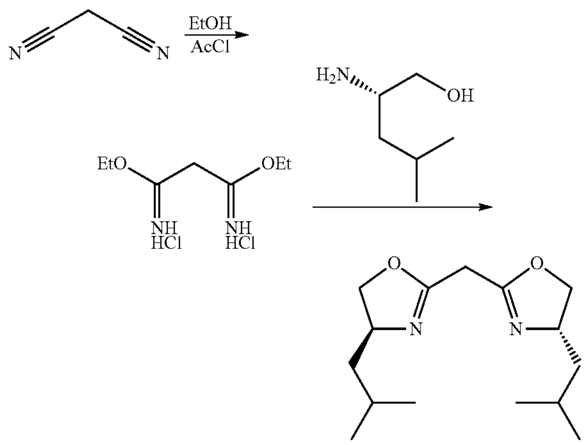

To a 1 L jacketed reactor under nitrogen was added malononitrile (25.0 g, 375 mmol, 1.0 eq.) and ethanol (250 mL). The light yellow solution was cooled to 0° C. Acetyl chloride (173 mL, 2435 mmol, 6.5 eq.) was added at a rate to keep reaction mixture below 10° C. The addition was completed after 3 h leading to a slurry. The mixture was allowed to warm to 22° C. and stirred for 21 h. Heptanes (250 mL) was added slowly to the slurry over 30 min. The resultant slurry was stirred for 30 min, drained and filtered. The wet cake was washed with heptanes (2×150 mL) and dried in vacuum oven for 16 h to afford diethyl malonimidate dihydrochloride product as off-white solid (87.0 g, 95% purity, 95% yield). Analytical data was consistent with reported data. To a 250 mL jacket reactor under N2 was added diethyl malonimidate dihydrochloride (12.0 g, 49.3 mmol, 1.0 eq.) and DCM (118 mL). To the off-white slurry at 23° C. was added a solution of (S)-2-amino-4-methylpentan-1-ol (12.4 g, 104 mmol, 2.1 eq.) in DCM (10 mL) in a dropwise manner via additional funnel while keeping T<25° C. The reaction mixture was stirred at 34° C. for 16 h and cooled down to 20° C. Water (100 mL) was added over 10 min and the mixture was stirred for 20 min. The separated aqueous layer was extracted with DCM (100 mL). The combined organic layers were washed with brine (2×60 mL), dried over anhydrous sodium sulfate, filtered and concentrated to afford bis((S)-4-isobutyl-4,5-dihydrooxazol-2-yl)methane as a light brown oil (11.79 g, 90% yield). 1H NMR (500 MHz, Chloroform-d) δ 4.37 (dd, J=9.4, 8.1 Hz, 2H), 4.22-4.11 (m, 2H), 3.86 (t, J=8.0 Hz, 2H), 3.32 (t, J=1.1 Hz, 2H), 1.74 (dq, J=13.4, 6.7 Hz, 2H), 1.61 (dt, J=13.6, 6.9 Hz, 2H), 1.29 (dt, J=13.4, 7.3 Hz, 2H), 0.99-0.92 (d, J=6.6 Hz, 6H), 0.92 (d, J=6.6 Hz, 6H). 13C NMR (101 MHz, Chloroform-d) δ 161.27, 73.33, 64.55, 45.17, 28.26, 25.16, 22.58, 22.53. LC-MS (ES+): m/z for C15H26N2O2 [M+H]+; observed 267.3, calculated 267.2.

While some aspects have been illustrated and described, a person with ordinary skill in the art, after reading the foregoing specification, can effect changes, substitutions of equivalents and other types of alterations to the compounds of the present technology or salts, agricultural compositions, derivatives, prodrugs, metabolites, tautomers or racemic mixtures thereof as set forth herein. Each aspect and aspect described above can also have included or incorporated therewith such variations or aspects as disclosed in regard to any or all of the other aspects and aspects.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The aspects, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other aspects are set forth in the following claims, along with the full scope of equivalents to which such claims are entitled.

While the invention has been particularly shown and described with reference to a preferred aspect and various alternate aspects, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

We claim:

1. A process for the preparation of the compound of Formula A

A

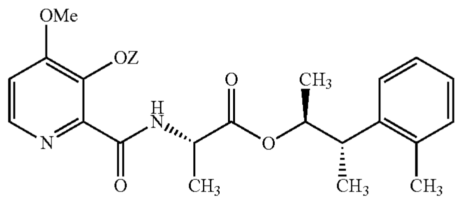

wherein Z is $CH_3CO$, $CH_3CH_2CO$ or $(CH_3)_2CHCO$; from the compound of Formula B

B

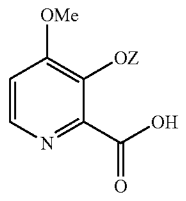

wherein Z is $CH_3CO$, $CH_3CH_2CO$ or $(CH_3)_2CHCO$; which comprises the steps of:

a) creating a first mixture containing the compound of Formula B, wherein Z is $CH_3CO$, $CH_3CH_2CO$ or $(CH_3)_2CHCO$, a coupling reagent, and a base;

b) adding at least one of the compounds of Formula C and Formula C1

C

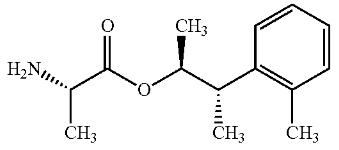

C1

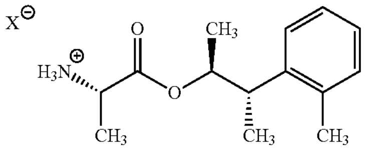

wherein X is CI, Br, $HSO_4$, $H_2PO_4$ or $CH_3SO_3$; to the first mixture to form a second mixture; and c) isolating the compound of Formula A from the second mixture.

2. The process of claim 1 wherein the coupling reagent is an alkyl chloroformate of the Formula $ClCO_2R$, wherein R is a C1-C4 alkyl or benzyl, or an acid chloride of the Formula RCOCl, wherein R is a C1-C4 alkyl.

3. The process of claim 1 wherein the base may be selected from the group including triethylamine (TEA), diisopropylethylamine (DIPEA), pyridine, potassium carbonate, and mixtures thereof.

4. The process of claim 1 wherein the first mixture further comprises a solvent selected from the group including dichloromethane (DCM), 1,2-dichloroethane (DCE), isopropyl acetate, tetrahydrofuran (THF), 2-MeTHF, acetonitrile (ACN), and mixtures thereof.

5. The process of claim 1 wherein Z is $CH_3CH_2CO$.

6. The process of claim 1 wherein Z is $CH_3CO$.

7. The process of claim 1 wherein Z is $(CH_3)_2CHCO$.

8. The process of claim 1 wherein X is Cl.

9. The process of claim 1 wherein X is Br.

10. A process for the preparation of the compound of Formula C1:

C1

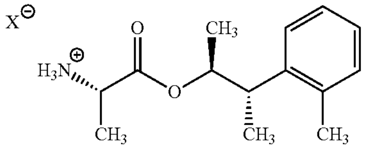

wherein X is CI, Br, $HSO_4$, $H_2PO_4$ or $CH_3SO_3$; comprising:

a) creating a first mixture containing the compound of Formula G2 as predominantly a single enantiomer

G2

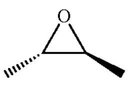

o-tolylmagnesium halide, and a copper catalyst;

b) isolating the compound of Formula D2

D2

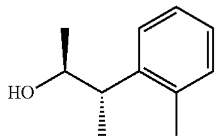

from the first mixture;

c) creating a second mixture containing the compound of Formula D2,

D2

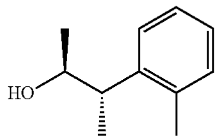

N-(tert-butoxycarbonyl)-L-alanine, an acylating agent, a catalyst and optionally a base;

d) isolating the compound of Formula F

F

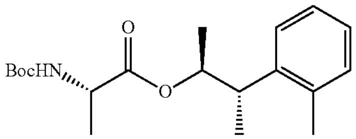

from the second mixture;

e) creating a third mixture containing the compound of Formula F and a strong acid;

wherein the strong acid is HCl, HBr, HI, $H_2SO_4$, $H_3PO_4$, $CF_3COOH$, or $CH_3SO_3H$; and f) isolating the compound of Formula C1, wherein X is CI, Br, $HSO_4$, $H_2PO_4$ or $CH_3SO_3$, from the third mixture.

11. A process for the preparation of a compound of Formula B

B

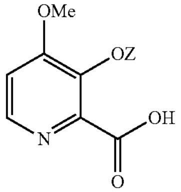

wherein Z is $CH_3CH_2CO$;

comprising the steps of:

a) reacting a compound of Formula B, wherein Z is H with an acylating reagent, and a base; and b) isolating the compound of Formula B, wherein Z is $CH_3CH_2CO$, from the mixture.

12. The process of claim 11 wherein the acylating agent is selected from one of propionic anhydride and propionyl chloride or mixtures thereof.

13. The compound of Formula B,

B

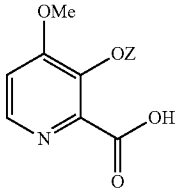

wherein Z is $CH_3CH_2CO$.

* * * * *